US010335401B2

(12) United States Patent
Nishiura et al.

(10) Patent No.: US 10,335,401 B2
(45) Date of Patent: Jul. 2, 2019

(54) NON-AROMATIC HETEROCYCLIC DERIVATIVE HAVING MGAT2 INHIBITORY ACTIVITY

(71) Applicant: Shionogi & Co., Ltd., Osaka (JP)

(72) Inventors: Yuji Nishiura, Osaka (JP); Kana Kurahashi, Osaka (JP); Naoki Ohyabu, Osaka (JP); Yoshikazu Sasaki, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 16/061,155

(22) PCT Filed: Dec. 21, 2016

(86) PCT No.: PCT/JP2016/088024
§ 371 (c)(1),
(2) Date: Jun. 11, 2018

(87) PCT Pub. No.: WO2017/110841
PCT Pub. Date: Jun. 29, 2017

(65) Prior Publication Data
US 2018/0353492 A1    Dec. 13, 2018

(30) Foreign Application Priority Data

Dec. 21, 2015  (JP) ................................. 2015-248306

(51) Int. Cl.

| A61K 31/444 | (2006.01) |
|---|---|
| C07D 405/14 | (2006.01) |
| C07D 413/14 | (2006.01) |
| A61K 31/435 | (2006.01) |
| C07D 401/04 | (2006.01) |
| C07D 409/14 | (2006.01) |
| C07D 211/86 | (2006.01) |
| A61P 9/10 | (2006.01) |
| A61P 3/04 | (2006.01) |
| A61P 3/06 | (2006.01) |
| A61P 3/10 | (2006.01) |
| A61K 31/4439 | (2006.01) |
| A61K 31/5377 | (2006.01) |

(52) U.S. Cl.
CPC .......... *A61K 31/444* (2013.01); *A61K 31/435* (2013.01); *A61K 31/4439* (2013.01); *A61K 31/5377* (2013.01); *A61P 3/04* (2018.01); *A61P 3/06* (2018.01); *A61P 3/10* (2018.01); *A61P 9/10* (2018.01); *C07D 211/86* (2013.01); *C07D 401/04* (2013.01); *C07D 405/14* (2013.01); *C07D 409/14* (2013.01); *C07D 413/14* (2013.01)

(58) Field of Classification Search
CPC ........................... A61K 31/444; C07D 405/14
See application file for complete search history.

(56) References Cited

U.S. PATENT DOCUMENTS

2015/0368242 A1   12/2015   Suzuki et al.

FOREIGN PATENT DOCUMENTS

| EP | 2 687 507 | 1/2014 |
|---|---|---|
| JP | 2014-5245 | 1/2014 |
| JP | 2014-9165 | 1/2014 |
| WO | 2008/038768 | 4/2008 |
| WO | 2010/095767 | 8/2010 |
| WO | 2012/091010 | 7/2012 |
| WO | 2013/082345 | 6/2013 |

(Continued)

OTHER PUBLICATIONS

International Preliminary Report on Patentability dated Jun. 26, 2018 in International (PCT) Application No. PCT/JP2016/088024.
International Search Report dated Feb. 28, 2017 in International Application No. PCT/JP2016/0880024.
Jingsong Cao et al., "A Predominant Role of Acyl-CoA:monoacylglycerol Acyltransferase-2 in Dietary Fat Absorption Implicated by Tissue Distribution, Sebcellular Localization, and Up-regulation by High Fat Diet*", Journal of Biological Chemistry (2004), 279, 18878-18886.
Chi-Liang Eric Yen et al., "Deficiency of the intestinal enzyme acyl CoA:monoacylglycerol acyltransferase-2 protects mice from metabolic disorders induced by high-fat feeding", Nature Medicine (2009), 15, 4, 442-446.

(Continued)

*Primary Examiner* — Golam M Shameem
(74) *Attorney, Agent, or Firm* — Wenderoth, Lind & Ponack, L.L.P.

(57) ABSTRACT

The present invention relates to a compound represented by Formula (I):

(I)

wherein X is, for example, C(=O); Z is, for example, C(=O); L is, for example, a single bond; A is, for example, aromatic carbocycle; R is, for example, $R^6$ or B; $R^2$ is, for example, hydrogen; $R^3$ is, for example, substituted or unsubstituted alkyl; $R^{4a}$ is, for example, hydrogen; $R^{4b}$ is, for example, hydrogen; $R^5$ is, for example, halogen; $R^6$ is, for example, halogen; $R^{7a}$ is, for example, hydrogen; $R^{7b}$ is, for example, hydrogen; $R^8$ is, for example, hydrogen; $R^9$ is, for example, hydrogen; m is 0 to 5; n is 0 to 5; and p is 1 to 6, or a pharmaceutically acceptable salt thereof, and a pharmaceutical composition comprising the same.

14 Claims, No Drawings

(56) References Cited

FOREIGN PATENT DOCUMENTS

| WO | 2013/112323 | 8/2013 |
|---|---|---|
| WO | 2013/116065 | 8/2013 |
| WO | 2014/074365 | 5/2014 |
| WO | 2014/193884 | 12/2014 |
| WO | 2015/112465 | 7/2015 |
| WO | 2015/129845 | 9/2015 |
| WO | 2015/134699 | 9/2015 |
| WO | 2015/134701 | 9/2015 |
| WO | 2015/191681 | 12/2015 |
| WO | 2016/024598 | 2/2016 |
| WO | 2016/121782 | 8/2016 |

OTHER PUBLICATIONS

Jonas G. Barlind et al., "Identification and design of a novel series of MGAT2 inhibitors", Bioorganic & Medicinal Chemistry Letters (2013), 23, 2721-2726.

James S. Scott et al., "Achieving improved permeability by hydrogen bond donor modulation in a series of MGAT2 inhibitors", Med. Chem. Commun (2013), 4, 1305-1311.

Tsuyoshi Busujima et al., "Identification of 2-[2-(4-tert-butylphenyl]-N-(4-fluorophenyl)-1,2,3,4-tetraphydroisoquinoline-6-sulfonamide (29) as an orally available MGAT2 inhibitor", Bioorganic & Medicinal Chemistry Letter (2015), 23, 5922-5931.

Kenjiro Sato et al., "Optimization of a novel series of N-phenylindoline-5-sulfonamide-based acyl CoA:monoacylglycerol acyltransferase-2 inhibitors: Mitigation of CYP3A4 time-dependent inhibition and phototoxic liabilities", Bioorganic & Medicinal Chemistry Letter (2015), 23, 4544-4560.

Joelle M. Onorato et al., "Cell-based assay of MGAT2—driven diacylglycerol synthesis for profiling inhibitors: use of a stable isotope-labeled substrate and high-resolution LC/MS", Journal of Lipid Research 2015, 56, 747-753.

Chihiro Okuma et al., "JTP-103237, a novel monoacylglycerol acyltransferase inhibitor, modulates fat absorption and prevents diet-induced obesity", European Journal of Pharmacology, 2015, 758, 72-81.

Kenjuro Sato et al., "Discovery of a Novel Series of N-Phenylindoline-5-sulfonamide Derivatives as Potent, Selective, and Orally Bioavailable Acyl CoA:Monoacylglycerol Acyltransferase-2 Inhibitors", Journal of Medicinal Chemistry (2015), 58, 3892-3909.

Tsuyoshi Busujima et al., "An Efficient and Convenient Synthesis of Acyl CoA:Monoacylglycerol Acyltransferase 2 Inhibitor, 2-[2(4-tert-Butylphenyl)Ethyl]-N-[4-(3-Cyclopentyl-Propyl)-2-Fluorophenyl]-1,2,3,4-Tetrahydroisoquino-Line-6-Sulfonamide", Heterocycles 2016, 92, 470-484.

Tsuyoshi Busujima et al., "Identification of 2-[2-(4-tert-Butylphenyl)ethyl]-N-[4-(3-cyclopentylpropyl)-2-fluorophenyl]-1,2,3,4-tetrahydroisoquinoline-6-sulfonamide as an Orally Active MGAT2 Inhibitor", Chemical and Pharmaceutical Bulletin, 2016, 64, 228-238.

Ryutaro Adachi et al., "Pharmacological characterization of a series of aryl-sulfonamide derivatives that potently and selectively inhibit monoacylglycerol acyltransferase 2", European Journal of Pharmacology, 2016, 791, 569-577.

Zhengping Ma et al., "Characterization of monoacylglycerol acyltransferase 2 inhibitors by a novel probe in binding assays", Analytical Biochemistry, 2016, 501, 48-55.

Kazumi Take et al., "Pharmacological Inhibition of Monoacylglycerol O-Acyltransferase 2 Improves Hyperlipidemia, Obesity, and Diabetes by Change in Intestinal Fat Utilization", PLOS ONE (DOI:10.1371/journal.pone.0150976).

Jenson Qi et al., "Novel LC/MS/MS and High-Throughput Mass Spectrometric Assays for Monoacylglycerol Acyltransferase Inhibitors", SLAS Discovery, 2017, 22, 433-439.

Jensen Qi et al., "Metabolic tracing of monoacylglycerol acyltransferase-2 activity in vitro and in vivo", Analytical Biochemistry, 2017, 524, 68-75.

Ryutaro Adachi et al., "Discovery of Human Intestinal MGAT Inhibitors Using High-Throughput Mass Spectrometry", SLAS Discovery, 2017, 22, 360-365.

NON-AROMATIC HETEROCYCLIC DERIVATIVE HAVING MGAT2 INHIBITORY ACTIVITY

TECHNICAL FIELD

The present invention relates to a compound having monoacylglycerol acyltransferase 2 (hereinafter, also referred to as "MGAT2") inhibitory activity or its pharmaceutically acceptable salt, and a pharmaceutical composition including thereof.

BACKGROUND ART

Obesity is increasingly becoming prevalent in recent years, and diet therapy, exercise therapy, drug therapy, and so on are performed for treatment of obesity. In the drug therapy, drugs including orlistat, mazindol, and sibutramine are used. However, they are not satisfactory in both aspects of efficacy and side effects.

One of the causes for obesity is excessive intake of neutral fat. Neutral fat (triglycerol) taken in meals is decomposed into 2-monoacylglycerol and free fatty acids by the action of pancreatic lipase in the digestive tract, and they are absorbed by small intestinal epithelial cells. An acyl group is transferred from the free fatty acids to the 2-monoacylglycerol by the action of monoacylglycerol acyltransferase (MGAT). The diacylglycerol formed is further converted into neutral fat by the action of diacylglycerol acyltransferase (DGAT).

Three isoforms of MGAT, namely, MGAT1, MGAT2, and MGAT3 have been identified. Among them, MGAT2 and MGAT3 are highly expressed in the small intestine, and believed to be involved in fat absorption in the small intestine.

It has been reported that an experiment with MGAT2 knock-out mice has demonstrated that high-fat diet promotes expression of MGAT2 in the small intestine to increase the MGAT activity (Non-patent Document 1). In addition, reduction of weight gain caused by high-fat diet, suppression of induction of insulin resistance, reduction of increase of blood cholesterol, prevention of fatty liver formation or the like, and promotion of energy consumption have been found for MGAT2 knock-out mice (Non-patent Document 2).

Although compounds having MGAT2 inhibitory activity have been previously reported (Patent Documents 1 to 15, Non-patent Documents 3 to 13), compounds of the present invention as described below have not been disclosed.

PRIOR ART REFERENCES

Patent Document

[Patent Document 1] International Publication WO 2010/095767A
[Patent Document 2] International Publication WO 2012/091010A
[Patent Document 3] International Publication WO 2012/124744A
[Patent Document 4] International Publication WO 2013/082345A
[Patent Document 5] International Publication WO 2013/112323A
[Patent Document 6] International Publication WO 2013/116065A
[Patent Document 7] International Publication WO 2013/116075A
[Patent Document 8] International Publication WO 2014/074365A
[Patent Document 9] International Publication WO 2014/133134A
[Patent Document 10] International Publication WO 2014/193884A
[Patent Document 11] Japanese Patent Laid-Open No. 2014-5245
[Patent Document 12] Japanese Patent Laid-Open No. 2014-9165
[Patent Document 13] International Publication WO 2015/129845A
[Patent Document 14] International Publication WO 2015/134699A
[Patent Document 15] International Publication WO 2015/134701A

Non-Patent Document

[Non-patent Document 1] Journal of Biological Chemistry (2004), 279, 18878-18886
[Non-patent Document 2] Nature Medicine (2009), 15, 4, 442-446
[Non-patent Document 3] Bioorganic & Medicinal Chemistry Letter (2013), 23, 2721-2726
[Non-patent Document 4] Med. Chem. Commun (2013), 4, 1305-1311
[Non-patent Document 5] Bioorganic & Medicinal Chemistry Letter (2015), 23, 5922-5931
[Non-patent Document 6] Bioorganic & Medicinal Chemistry Letter (2015), 23, 4544-4560
[Non-patent Document 7] Journal of Lipid Research 2015, 56, 747-753
[Non-patent Document 8] European Journal of Pharmacology, 2015, 758, 72-81
[Non-patent Document 9] Journal of Medicinal Chemistry (2015), 58, 3892-3909
[Non-patent Document 10] HETEROCYCLES 2016, 92, 470-484
[Non-patent Document 11] Chemical and Pharmaceutical Bulletin, 2016, 64, 228-238
[Non-patent Document 12] European Journal of Pharmacology, 2016, 791, 569-577
[Non-patent Document 13] Analytical Biochemistry, 2016, 501, 48-55

SUMMARY OF THE INVENTION

Problems to be Solved by the Invention

An object of the present invention is to provide a compound having MGAT2 inhibitory activity or its pharmaceutically acceptable salt, and a pharmaceutical composition including thereof.

Means for Solving the Problem

The present inventors have diligently studied, and succeeded in synthesizing superior compounds having MGAT2 inhibitory activity. Specifically, the present invention relates to the followings.

[1] A compound represented by Formula (I):

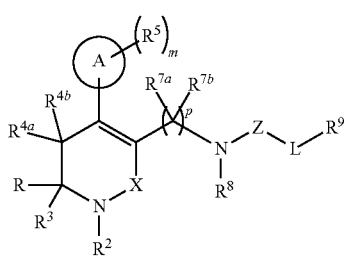

wherein
X is C(=O), C(=S), or SO$_2$;
Z is C(=O), C(=S), C(=N—R$^N$), or SO$_2$;
L is a single bond, —O—, —S—, or —NR$^N$—;
R is R$^6$ or a group represented by the following formula:

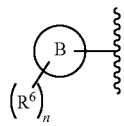

A is aromatic carbocycle, non-aromatic carbocycle, aromatic heterocycle, or non-aromatic heterocycle;
B is aromatic carbocycle, non-aromatic carbocycle, aromatic heterocycle, or non-aromatic heterocycle;
R$^2$ is hydrogen, substituted or unsubstituted alkyl, substituted or unsubstituted alkylcarbonyl, substituted or unsubstituted alkyloxycarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;
R$^3$ is hydrogen, cyano, substituted or unsubstituted carbamoyl, substituted or unsubstituted alkyl, substituted or unsubstituted alkenyl, substituted or unsubstituted alkynyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;
R$^{4a}$ and R$^{4b}$ are each independently hydrogen, halogen, hydroxy, cyano, substituted or unsubstituted alkyl, substituted or unsubstituted non-aromatic carbocyclyl, or substituted or unsubstituted non-aromatic heterocyclyl,
or, optionally, R$^{4a}$ and R$^{4b}$ are taken together with the adjacent carbon atom to form substituted or unsubstituted non-aromatic carbocycle or substituted or unsubstituted non-aromatic heterocycle;
R$^5$ is each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyloxy, substituted or unsubstituted alkenylcarbonyloxy, substituted or unsubstituted alkynylcarbonyloxy, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by the formula: -L$^1$-N=S(=O)(—R$^{S1}$)—R$^{S2}$, a group represented by the formula: -L$^1$—S(=O)(=N—R$^N$)—R$^{S1}$, a group represented by the formula: —N=S(=N—R$^N$)(—R$^{S1}$)—R$^{S2}$, or a group represented by the formula: —S(=N—R$^N$)$_2$—R$^{S1}$;

R$^6$ is each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyloxy, substituted or unsubstituted alkenylcarbonyloxy, substituted or unsubstituted alkynylcarbonyloxy, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by the formula: -L$^1$-N=S(=O)(—R$^{S1}$)—R$^{S2}$, a group represented by the formula: -L$^1$-S(=O)(=N—R$^N$)—R$^{S1}$, a group represented by the formula: —N=S(=N—R$^N$)(—R$^{S1}$)—R$^{S2}$, or a group represented by the formula: —S(=N—R$^N$)$_2$—R$^{S1}$;

R$^{7a}$ is each independently hydrogen, halogen, hydroxy, cyano, substituted or unsubstituted amino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, and R$^{7b}$ is each independently hydrogen, halogen, hydroxy, cyano, substituted or unsubstituted amino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, or, optionally, R$^{7a}$ and R$^{7b}$ attached to the same carbon atom are taken together with the adjacent carbon atom to form substituted or unsubstituted non-aromatic carbocycle or substituted or unsubstituted non-aromatic heterocycle;

R$^8$ is hydrogen or substituted or unsubstituted alkyl;

R$^9$ is hydrogen, substituted or unsubstituted amino, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;

$L^1$ is each independently a single bond, alkylene, or C(=O);

$R^{S1}$ and $R^{S2}$ are each independently hydrogen, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or, optionally, $R^{S1}$ and $R^{S2}$ bonding to the same sulfur atom are taken together with the sulfur atom to form substituted or unsubstituted non-aromatic heterocycle;

$R^N$ is each independently hydrogen, cyano, substituted or unsubstituted carbamoyl, substituted or unsubstituted alkyl, substituted or unsubstituted alkylcarbonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl;

m is an integer of 0 to 5;
n is an integer of 0 to 5; and
p is an integer of 1 to 6,
or its pharmaceutically acceptable salt.

[2] The compound or its pharmaceutically acceptable salt according to [1], wherein $R^{7a}$ and $R^{7b}$ are each hydrogen.

[3] The compound or its pharmaceutically acceptable salt according to [1] or [2], wherein p is 1.

[4] The compound or its pharmaceutically acceptable salt according to any one of [1] to [3], wherein Z is C(=O) or $SO_2$.

[5] The compound or its pharmaceutically acceptable salt according to any one of [1] to [4], wherein A is aromatic carbocycle or aromatic heterocycle.

[6] The compound or its pharmaceutically acceptable salt according to any one of [1] to [5], wherein B is aromatic carbocycle or aromatic heterocycle.

[7] The compound or its pharmaceutically acceptable salt according to any one of [1] to [6], wherein $R^5$ is each independently halogen, substituted or unsubstituted alkyl, substituted or unsubstituted alkenyl, substituted or unsubstituted alkyloxy, substituted or unsubstituted alkylcarbonyl, or substituted or unsubstituted non-aromatic carbocyclyl.

[8] The compound or its pharmaceutically acceptable salt according to any one of [1] to [7], wherein $R^6$ is each independently halogen, substituted or unsubstituted alkyl, substituted or unsubstituted alkenyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

[9] The compound or its pharmaceutically acceptable salt according to [1], wherein the compound is selected from the group consisting of Example Compounds I-1, I-4, I-8, I-9, I-10, I-12, I-13, I-14, I-15, I-17, I-20, I-24, I-26, I-27, I-29, I-30, I-35, I-37, I-38, and I-42.

[10] The compound or its pharmaceutically acceptable salt according to [1], wherein the compound is selected from the group consisting of Example Compounds I-1, I-7, I-13, I-17, I-47, I-56, I-57, I-58, I-59, I-62, I-69, I-75, I-88, I-90, I-97, I-98, I-101, I-106, I-108, and I-114.

[11] A pharmaceutical composition comprising the compound or its pharmaceutically acceptable salt according to any one of [1] to [10].

[12] The pharmaceutical composition according to [11], having MGAT2 inhibitory activity.

[13] The pharmaceutical composition according to [11] or [12], for use in preventing or treating an MGAT2-related disease.

[14] The pharmaceutical composition according to [13], for use in preventing or treating obesity, metabolic syndrome, hyperlipidemia, hypertriglyceridemia, hyper-VLDL-triglyceridemia, hyperfattyacidemia, diabetes mellitus, or arteriosclerosis.

[15] An MGAT2 inhibitor comprising the compound or its pharmaceutically acceptable salt according to any one of [1] to [10].

[16] A method for treating or preventing an MGAT2-associated disease, comprising administering the compound or its pharmaceutically acceptable salt according to any one of [1] to [10].

[17] A compound or its pharmaceutically acceptable salt according to any one of [1] to [10] for use in treating or preventing an MGAT2-associated disease.

Effect of the Invention

The compounds of the present invention have MGAT2 inhibitory activity, and are useful as a prophylactic agent and/or therapeutic agent for, for example, obesity, metabolic syndrome, hyperlipidemia, hypertriglyceridemia, hyper-VLDL-triglyceridemia, hyperfattyacidemia, diabetes mellitus, or arteriosclerosis.

MODE FOR CARRYING OUT THE INVENTION

The meanings of terms used in this description are described below. Unless otherwise stated, a term when being used singly and the term when being used in combination with another term have the same meaning.

The term "consist of" means having only a constituent element.

The term "comprise" means that an unmentioned factor is not excluded with no limitation to a constituent.

"Halogen" includes a fluorine atom, a chlorine atom, a bromine atom, and an iodine atom. In particular, a fluorine atom and a chlorine atom are preferable.

"Alkyl" includes a C1 to C15, preferably C1 to C10, more preferably C1 to C6, and further preferably C1 to C4 linear or branched hydrocarbon group. For example, it includes methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.

A preferred embodiment of "alkyl" is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

"Alkenyl" includes a C2 to C15, preferably C2 to C10, more preferably C2 to C6 and further preferably C2 to C4 linear or branched hydrocarbon group having one or more double bond(s) at any position(s). For example, it includes vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

A preferred embodiment of "alkenyl" is vinyl, allyl, propenyl, isopropenyl or butenyl.

"Alkynyl" includes a C2 to C10, preferably C2 to C8, more preferably C2 to C6 and further preferably C2 to C4 linear or branched hydrocarbon group having one or more triple bond(s) at any position(s). Furthermore, it may have double bond(s) at any position(s). For example, it includes ethynyl, propynyl, butynyl, pentynyl, hexynyl, heptynyl, octynyl, nonynyl, decynyl and the like.

A preferred embodiment of "alkynyl" is ethynyl, propynyl, butynyl or pentynyl.

"Alkylene" includes a C1 to C15, preferably C1 to C10, more preferably C1 to C6 and further preferably C1 to C4 linear or branched divalent hydrocarbon group. For example, it includes methylene, ethylene, trimethylene, propylene, tetramethylene, pentamethylene, hexamethylene and the like.

"Aromatic carbocyclyl" means a cyclic aromatic hydrocarbon group which is monocyclic or polycyclic having two or more rings. For example, it includes phenyl, naphthyl, anthryl, phenanthryl and the like.

A preferred embodiment of "aromatic carbocyclyl" is phenyl.

"Non-aromatic carbocyclyl" means a cyclic saturated hydrocarbon group or a cyclic unsaturated non-aromatic hydrocarbon group, which is monocyclic or polycyclic having two or more rings. "Non-aromatic carbocyclyl", which is polycyclic having two or more rings, includes a fused ring group wherein a non-aromatic carbocycle, which is monocyclic or polycyclic having two or more rings, is fused with a ring of the above "aromatic carbocyclyl".

In addition, the "non-aromatic carbocyclyl" also includes a group having a bridge or a group to form a spiro ring as follows:

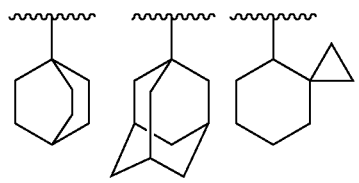

A non-aromatic carbocyclyl which is monocyclic is preferably C3 to C16, more preferably C3 to C12 and further preferably C4 to C8 carbocyclyl. For example, it includes cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, cyclohexadienyl and the like.

A non-aromatic carbocyclyl which is polycyclic having two or more rings is preferably C8 to C20, and more preferably C8 to C16 carbocyclyl. For example, it includes indanyl, indenyl, acenaphthyl, tetrahydronaphthyl, fluorenyl and the like.

"Aromatic heterocyclyl" means an aromatic cyclyl, which is monocyclic or polycyclic having two or more rings, containing one or more and the same or different heteroatom(s) selected independently from O, S and N. An aromatic heterocyclyl, which is polycyclic having two or more rings, includes a fused ring group wherein an aromatic heterocyclyl, which is monocyclic or polycyclic having two or more rings, is fused with a ring of the above "aromatic carbocyclyl".

An aromatic heterocyclyl which is monocyclic is preferably a 5- to 8-membered and more preferably 5- or 6-membered ring. For example, it includes pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, thiadiazolyl and the like.

An aromatic heterocyclyl which is bicyclic is preferably a 8- to 10-membered and more preferably 9- or 10-membered ring. For example, it includes indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl and the like.

An aromatic heterocyclyl which is polycyclic having three or more rings includes, for example, carbazolyl, acridinyl, xanthenyl, phenothiazinyl, phenoxathiinyl, phenoxazinyl, dibenzofuryl and the like.

"Non-aromatic heterocyclyl" means a non-aromatic cyclyl, which is monocyclic or polycyclic having two or more rings, containing one or more and the same or different heteroatom(s) selected independently from O, S and N. "Non-aromatic heterocyclyl", which is polycyclic having two or more rings, includes a fused ring group wherein a non-aromatic heterocycle, which is monocyclic or polycyclic having two or more ring(s), is fused with a ring of the above "aromatic carbocyclyl", "non-aromatic carbocyclyl" and/or "aromatic heterocyclyl", and includes a fused ring group wherein a ring of the above "aromatic heterocyclyl" is fused with the above "non-aromatic carbocyclyl", which is monocyclic or polycyclic having two or more ring(s).

In addition, the "non-aromatic heterocyclyl" also includes a group having a bridge or a group to form a spiro ring as follows:

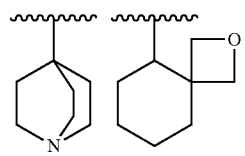

A non-aromatic heterocyclyl which is monocyclic is preferably a 3- to 8-membered and more preferably 5- or 6-membered ring. For example, it includes dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl, thiazinyl and the like.

A non-aromatic heterocyclyl which is polycyclic having two or more rings is preferably an 8- to 20-membered and more preferably 8- to 10-membered ring. For example, it includes indolinyl, isoindolinyl, chromanyl, isochromanyl and the like.

The substituents of "substituted carbamoyl", "substituted thiocarbamoyl", "substituted amidino", "substituted amino", "substituted ureido", "substituted guanidino", "substituted sulfamoyl", "substituted alkyl", "substituted alkenyl", "substituted alkynyl", "substituted alkyloxy", "substituted alkenyloxy", "substituted alkynyloxy", "substituted alkylcarbonyloxy", "substituted alkenylcarbonyloxy", "substituted alkynylcarbonyloxy", "substituted alkylcarbonyl", "substituted alkenylcarbonyl", "substituted alkynylcarbonyl", "substituted alkyloxycarbonyl", "substituted alkenyloxycarbonyl", "substituted alkynyloxycarbonyl", "substituted alkylsulfanyl", "substituted alkenylsulfanyl", "substituted alkynylsulfanyl", "substituted alkylsulfinyl", "substituted alkenylsulfinyl", "substituted alkynylsulfinyl", "substituted alkylsulfonyl", "substituted alkenylsulfonyl", and "substituted alkynylsulfonyl" include the substituents given below. A carbon atom or nitrogen atom at any position(s) may be bonded to one or more group(s) selected from the following substituents.

The substituents: halogen, hydroxy, cyano, formyl, formyloxy, thioformyl, carboxy, thiocarboxy, dithiocarboxy, carbamoyl, thiocarbamoyl, amidino, amino, hydroxyamino, imino, hydroxyimino, nitro, nitroso, azido, hydrazino, ureido, guanidino, pentafluorothio, thiol, sulfino, sulfo, sulfamoyl, trialkylsilyl, alkyl, alkenyl, alkynyl, alkyloxy, alkenyloxy, alkynyloxy, alkylcarbonyloxy, alkenylcarbonyloxy, alkynylcarbonyloxy, alkylcarbonyl, alkenylcarbonyl, alkynylcarbonyl, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, alkylsulfonyl, alkenylsulfonyl, alkynylsulfonyl, monoalkylaminosulfonyl, monoalkenylaminosulfonyl, monoalkynylaminosulfonyl, dialkylaminosulfonyl, dialkenylaminosulfonyl, dialkynylaminosulfonyl, monoalkylamino, monoalkenylamino, monoalkynylamino, dialkylamino, dialkenylamino, dialkynylamino, monoalkylcarbonylamino, monoalkenylcarbonylamino, monoalkynylcarbonylamino, dialkylcarbonylamino, dialkenylcarbonylamino, dialkynylcarbonylamino, monoalkyloxycarbonylamino, monoalkenyloxycarbonylamino, monoalkynyloxycarbonylamino, dialkyloxycarbonylamino, dialkenyloxycarbonylamino, dialkynyloxycarbonylamino, monoalkylsulfonylamino, monoalkenylsulfonylamino, monoalkynylsulfonylamino, dialkylsulfonylamino, dialkenylsulfonylamino, dialkynylsulfonylamino, alkylimino, alkenylimino, alkynylimino, alkyloxyimino, alkenyloxyimino, alkynyloxyimino, monoalkylcarbamoyl, monoalkenylcarbamoyl, monoalkynylcarbamoyl, dialkylcarbamoyl, dialkenylcarbamoyl, dialkynylcarbamoyl, monoalkyloxycarbamoyl, monoalkenyloxycarbamoyl, monoalkynyloxycarbamoyl, dialkyloxycarbamoyl, dialkenyloxycarbamoyl, dialkynyloxycarbamoyl, monoalkylcarbonylcarbamoyl, monoalkenylcarbonylcarbamoyl, monoalkynylcarbonylcarbamoyl, monoalkyloxycarbonylcarbamoyl, monoalkenyloxycarbonylcarbamoyl, monoalkynyloxycarbonylcarbamoyl, monoalkylsulfonylcarba moyl, monoalkenylsulfonylcarbamoyl, monoalkynylsulfonylcarbamoyl, monoalkylsulfamoyl, monoalkenylsulfamoyl, monoalkynylsulfamoyl, dialkylsulfamoyl, dialkenylsulfamoyl, dialkynylsulfamoyl, monoalkyloxysulfamoyl, monoalkenyloxysulfamoyl, monoalkynyloxysulfamoyl, dialkyloxysulfamoyl, dialkenyloxysulfamoyl, dialkynyloxysulfamoyl, monoalkylcarbonylsulfamoyl, monoalkenylcarbonylsulfamoyl, monoalkynylcarbonylsulfamoyl, monoalkyloxycarbonylsulfamoyl, monoalkenyloxycarbonylsulfamoyl, monoalkynyloxycarbonylsulfamoyl, monoalkylsulfonylsulfamoyl, monoalkenylsulfonylsulfamoyl, monoalkynylsulfonylsulfamoyl, aromatic carbocyclyl, non-aromatic carbocyclyl, aromatic heterocyclyl, non-aromatic heterocyclyl, aromatic carbocycloxy, non-aromatic carbocyclyloxy, aromatic heterocyclyloxy, non-aromatic heterocyclyloxy, aromatic carbocyclylcarbonyloxy, non-aromatic carbocyclylcarbonyloxy, aromatic heterocyclylcarbonyloxy, non-aromatic heterocyclylcarbonyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylsulfanyl, non-aromatic carbocyclylsulfanyl, aromatic heterocyclylsulfanyl, non-aromatic heterocyclylsulfanyl, aromatic carbocyclylsulfinyl, non-aromatic carbocyclylsulfinyl, aromatic heterocyclylsulfinyl, non-aromatic heterocyclylsulfinyl, aromatic carbocyclylsulfonyl, non-aromatic carbocyclylsulfonyl, aromatic heterocyclylsulfonyl, non-aromatic heterocyclylsulfonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkylcarbonyl, non-aromatic carbocyclylalkylcarbonyl, aromatic heterocyclylalkylcarbonyl, non-aromatic heterocyclylalkylcarbonyl, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylsulfanyl, non-aromatic carbocyclylalkylsulfanyl, aromatic heterocyclylalkylsulfanyl, non-aromatic heterocyclylalkylsulfanyl, aromatic carbocyclylalkylsulfinyl, non-aromatic carbocyclylalkylsulfinyl, aromatic heterocyclylalkylsulfinyl, non-aromatic heterocyclylalkylsulfinyl, aromatic carbocyclylalkylsulfonyl, non-aromatic carbocyclylalkylsulfonyl, aromatic heterocyclylalkylsulfonyl, non-aromatic heterocyclylalkylsulfonyl, aromatic carbocyclylalkylamino, non-aromatic carbocyclylalkylamino, aromatic heterocyclylalkylamino, non-aromatic heterocyclylalkylamino, aromatic carbocyclylalkylcarbonylamino, non-aromatic carbocyclylalkylcarbonylamino, aromatic heterocyclylalkylcarbonylamino, non-aromatic heterocyclylalkylcarbonylamino, aromatic carbocyclylalkyloxycarbonylamino, non-aromatic carbocyclylalkyloxycarbonylamino, aromatic heterocyclylalkyloxycarbonylamino, non-aromatic heterocyclylalkyloxycarbonylamino, aromatic carbocyclylalkylsulfonylamino, non-aromatic carbocyclylalkylsulfonylamino, aromatic heterocyclylalkylsulfonylamino, non-aromatic heterocyclylalkylsulfonylamino, aromatic carbocyclyloxyalkylamino, non-aromatic carbocyclyloxyalkylamino, aromatic heterocyclyloxyalkylamino, non-aromatic heterocyclyloxyalkylamino, aromatic carbocyclyl substituted with aromatic carbocyclyl, non-aromatic carbocyclyl substituted with aromatic carbocyclyl, aromatic heterocyclyl substituted with aromatic carbocyclyl, non-aromatic heterocyclyl substituted with aromatic carbocyclyl, aromatic carbocyclyl substituted with non-aromatic carbocyclyl, non-aromatic carbocyclyl substituted with non-aromatic carbocyclyl, aromatic heterocyclyl substituted with non-aromatic carbocyclyl, non-aromatic heterocyclyl substituted with non-aromatic carbocyclyl, aromatic carbocyclyl substituted with aromatic heterocyclyl, non-aromatic carbocyclyl substituted with aromatic heterocyclyl, aromatic heterocyclyl substituted with aromatic heterocyclyl, non-aromatic heterocyclyl substituted with aromatic heterocyclyl, aromatic carbocyclyl substituted with non-aromatic heterocyclyl, non-aromatic carbocyclyl substituted with non-aromatic heterocyclyl, aromatic heterocyclyl substituted with non-aromatic heterocyclyl, and non-aromatic heterocyclyl substituted with non-aromatic heterocyclyl.

The substituents on the ring of "aromatic carbocycle", "non-aromatic carbocycle", "aromatic heterocycle", or "non-aromatic heterocycle" of "substituted aromatic carbocyclyl", "substituted non-aromatic carbocyclyl", "substituted aromatic heterocyclyl", "substituted non-aromatic heterocyclyl", "substituted aromatic carbocyclyloxy", "substituted non-aromatic carbocyclyloxy", "substituted aromatic heterocyclyloxy", "substituted non-aromatic heterocyclyloxy", "substituted aromatic carbocyclylcarbonyloxy", "substituted non-aromatic carbocyclylcarbonyloxy", "substituted aromatic heterocyclylcarbonyloxy", "substituted non-aromatic heterocyclylcarbonyloxy", "substituted aromatic carbocyclylcarbonyl", "substituted non-aromatic carbocyclylcarbonyl", "substituted aromatic heterocyclylcarbonyl", "substituted non-aromatic heterocyclylcarbonyl", "substituted aromatic carbocyclyloxycarbonyl", "substituted non-aromatic carbocyclyloxycarbonyl", "substituted aromatic heterocyclyloxycarbonyl", "substituted non-aromatic heterocyclyloxycarbonyl", "substituted aromatic carbocyclylsulfanyl", "substituted non-aromatic carbocyclylsulfanyl", "substituted aromatic heterocyclylsulfanyl", "substituted non-aromatic heterocyclylsulfanyl", "substituted aromatic carbocyclylsulfinyl", "substituted non-aromatic carbocyclylsulfinyl", "substituted aromatic heterocyclylsulfinyl", "substituted non-aromatic heterocyclylsulfinyl", "substituted aromatic carbocyclylsulfonyl", "substituted non-aromatic carbocyclylsulfonyl", "substituted aromatic heterocyclylsulfonyl", and "substituted non-aromatic heterocyclylsulfonyl" include the substituents given below. An atom at any position(s) on the ring may be bonded to one or more group(s) selected from the following substituents.

The substituents: halogen, hydroxy, cyano, formyl, formyloxy, thioformyl, carboxy, thiocarboxy, dithiocarboxy, carbamoyl, thiocarbamoyl, amidino, amino, hydroxyamino, imino, hydroxyimino, nitro, nitroso, azido, hydrazino, ureido, guanidino, pentafluorothio, thiol, sulfino, sulfo, sulfamoyl, trialkylsilyl, alkyl, alkenyl, alkynyl, alkyloxy, alkenyloxy, alkynyloxy, alkylcarbonyloxy, alkenylcarbonyloxy, alkynylcarbonyloxy, alkylcarbonyl, alkenylcarbonyl, alkynylcarbonyl, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, alkylsulfonyl, alkenylsulfonyl, alkynylsulfonyl, monoalkylaminosulfonyl, monoalkenylaminosulfonyl, monoalkynylaminosulfonyl, dialkylaminosulfonyl, dialkenylaminosulfonyl, dialkynylaminosulfonyl, monoalkylamino, monoalkenylamino, monoalkynylamino, dialkylamino, dialkenylamino, dialkynylamino, monoalkylcarbonylamino, monoalkenylcarbonylamino, monoalkynylcarbonylamino, dialkylcarbonylamino, dialkenylcarbonylamino, dialkynylcarbonylamino, monoalkyloxycarbonylamino, monoalkenyloxycarbonylamino, monoalkynyloxycarbonylamino, dialkyloxycarbonylamino, dialkenyloxycarbonylamino, dialkynyloxycarbonylamino, monoalkylsulfonylamino, monoalkenylsulfonylamino, monoalkynylsulfonylamino, dialkylsulfonylamino, dialkenylsulfonylamino, dialkynylsulfonylamino, alkylimino, alkenylimino, alkynylimino, alkyloxyimino, alkenyloxyimino, alkynyloxyimino, monoalkylcarbamoyl, monoalkenylcarbamoyl, monoalkynylcarbamoyl, dialkylcarbamoyl, dialkenylcarbamoyl, dialkynylcarbamoyl, monoalkyloxycarbamoyl, monoalkenyloxycarbamoyl, monoalkynyloxycarbamoyl, dialkyloxycarbamoyl, dialkenyloxycarbamoyl, dialkynyloxycarbamoyl, monoalkylcarbonylcarbamoyl, monoalkenylcarbonylcarbamoyl, monoalkynylcarbonylcarbamoyl, monoalkyloxycarbonylcarbamoyl, monoalkenyloxycarbonylcarbamoyl, monoalkynyloxycarbonylcarbamoyl, monoalkylsulfonylcarbamoyl, monoalkenylsulfonylcarbamoyl, monoalkynylsulfonylcarbamoyl, monoalkylsulfamoyl, monoalkenylsulfamoyl, monoalkynylsulfamoyl, dialkylsulfamoyl, dialkenylsulfamoyl, dialkynylsulfamoyl, monoalkyloxysulfamoyl, monoalkenyloxysulfamoyl, monoalkynyloxysulfamoyl, dialkyloxysulfamoyl, dialkenyloxysulfamoyl, dialkynyloxysulfamoyl, monoalkylcarbonylsulfamoyl, monoalkenylcarbonylsulfamoyl, monoalkynylcarbonylsulfamoyl, monoalkyloxycarbonylsulfamoyl, monoalkenyloxycarbonylsulfamoyl, monoalkynyloxycarbonylsulfamoyl, monoalkylsulfonylsulfamoyl, monoalkenylsulfonylsulfamoyl, monoalkynylsulfonylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyloxy, non-aromatic carbocyclylcarbonyloxy, aromatic heterocyclylcarbonyloxy, non-aromatic heterocyclylcarbonyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylsulfanyl, non-aromatic carbocyclylsulfanyl, aromatic heterocyclylsulfanyl, non-aromatic heterocyclylsulfanyl, aromatic carbocyclylsulfinyl, non-aromatic carbocyclylsulfinyl, aromatic heterocyclylsulfinyl, non-aromatic heterocyclylsulfinyl, aromatic carbocyclylsulfonyl, non-aromatic carbocyclylsulfonyl, aromatic heterocyclylsulfonyl, non-aromatic heterocyclylsulfonyl, aromatic carbocyclylalkyl, non-aromatic carbocyclylalkyl, aromatic heterocyclylalkyl, non-aromatic heterocyclylalkyl, aromatic carbocyclylalkyloxy, non-aromatic carbocyclylalkyloxy, aromatic heterocyclylalkyloxy, non-aromatic heterocyclylalkyloxy, aromatic carbocyclylalkylcarbonyl, non-aromatic carbocyclylalkylcarbonyl, aromatic heterocyclylalkylcarbonyl, non-aromatic heterocyclylalkylcarbonyl, aromatic carbocyclylalkyloxycarbonyl, non-aromatic carbocyclylalkyloxycarbonyl, aromatic heterocyclylalkyloxycarbonyl, non-aromatic heterocyclylalkyloxycarbonyl, aromatic carbocyclylalkylsulfanyl, non-aromatic carbocyclylalkylsulfanyl, aromatic heterocyclylalkylsulfanyl, non-aromatic heterocyclylalkylsulfanyl, aromatic carbocyclylalkylsulfinyl, non-aromatic carbocyclylalkylsulfinyl, aromatic heterocyclylalkylsulfinyl, non-aromatic heterocyclylalkylsulfinyl, aromatic carbocyclylalkylsulfonyl, non-aromatic carbocyclylalkylsulfonyl, aromatic heterocyclylalkylsulfonyl, non-aromatic heterocyclylalkylsulfonyl, aromatic carbocyclylalkylamino, non-aromatic carbocyclylalkylamino, aromatic heterocyclylalkylamino, non-aromatic heterocyclylalkylamino, aromatic carbocyclylalkylcarbonylamino, non-aromatic carbocyclylalkylcarbonylamino, aromatic heterocyclylalkylcarbonylamino, non-aromatic heterocyclylalkylcarbonylamino, aromatic carbocyclylalkyloxycarbonylamino, non-aromatic carbocyclylalkyloxycarbonylamino, aromatic heterocyclylalkyloxycarbonylamino, non-aromatic heterocyclylalkyloxycarbonylamino, aromatic carbocyclylalkylsulfonylamino, non-aromatic carbocyclylalkylsulfonylamino, aromatic heterocyclylalkylsulfonylamino, non-aromatic heterocyclylalkylsulfonylamino, aromatic carbocyclyloxyalkylamino, non-aromatic carbocyclyloxyalkylamino, aromatic heterocyclyloxyalkylamino, non-aromatic heterocyclyloxyalkylamino, aromatic carbocyclyl substituted with aromatic carbocyclyl, non-aromatic carbocyclyl substituted with aromatic carbocyclyl, aromatic heterocyclyl substituted with aromatic carbocyclyl, non-aromatic heterocyclyl substituted with aromatic carbocyclyl, aromatic carbocyclyl substituted with non-aromatic carbocyclyl, non-aromatic carbocyclyl substituted with non-aromatic carbocyclyl, aromatic heterocyclyl substituted with non-aromatic carbocyclyl, non-aromatic heterocyclyl substituted with non-aromatic carbocyclyl, aromatic carbocyclyl substituted with aromatic heterocyclyl, non-aromatic carbocyclyl substituted with aromatic heterocyclyl, aromatic heterocyclyl substituted with aromatic heterocyclyl, non-aromatic heterocyclyl substituted with aromatic heterocyclyl, aromatic carbocyclyl substituted with non-aromatic heterocyclyl, non-aromatic carbocyclyl substituted with non-aromatic heterocyclyl, aromatic heterocyclyl substituted with non-aromatic heterocyclyl, and non-aromatic heterocyclyl substituted with non-aromatic heterocyclyl.

"Substituted or unsubstituted non-aromatic carbocyclyl" and "substituted or unsubstituted non-aromatic heterocyclyl" may be substituted with "oxo". This case means a group wherein two hydrogen atoms on a carbon atom are replaced with oxo as below.

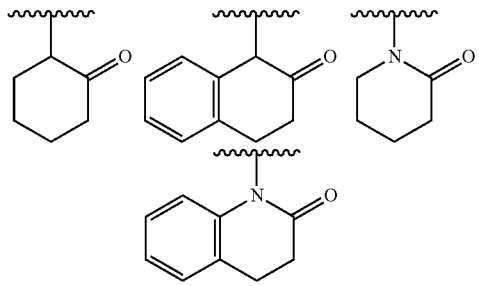

The non-aromatic carbocycle or non-aromatic heterocycle parts of the above "substituted or unsubstituted non-aromatic carbocyclyloxy", "substituted or unsubstituted non-aromatic heterocyclyloxy", "substituted or unsubstituted non-aromatic carbocyclylcarbonyloxy", "substituted or unsubstituted non-aromatic heterocyclylcarbonyloxy", "substituted or unsubstituted non-aromatic carbocyclylcarbonyl", "substituted or unsubstituted non-aromatic heterocyclylcarbonyl", "substituted or unsubstituted non-aromatic carbocyclyloxycarbonyl", "substituted or unsubstituted non-aromatic heterocyclyloxycarbonyl", "substituted or unsubstituted non-aromatic carbocyclylsulfanyl", "substituted or unsubstituted non-aromatic heterocyclylsulfanyl", "substituted or unsubstituted non-aromatic carbocyclylsulfinyl", "substituted or unsubstituted non-aromatic heterocyclylsulfinyl", "substituted or unsubstituted non-aromatic carbocyclylsulfonyl", and "substituted or unsubstituted non-aromatic heterocyclylsulfonyl" may be substituted with "oxo" as above.

Preferred embodiments of X, Z, L, A, B, R, $R^2$, $R^3$, $R^{4a}$, $R^{4b}$, $R^5$, $R^6$, $R^{7a}$, $R^{7b}$, $R^8$, $R^9$, $R^{S1}$, $R^{S2}$, $R^N$, $L^1$, m, n, and p in the compound represented by Formula (I) are described below. A compound having a possible combination of those described below is preferable.

X includes C(=O), C(=S), and $SO_2$.
A preferred embodiment of X includes C(=O) or C(=S).
A more preferred embodiment of X includes C(=O).
Z includes C(=O), C(=S), C(=N—$R^N$), and $SO_2$.
A preferred embodiment of Z includes C(=O) or $SO_2$.
L includes a single bond, —O—, —S—, and —$NR^N$—.
A preferred embodiment of L includes a single bond, —O—, or —$NR^N$—.

R is $R^6$ or a group represented by the following formula:

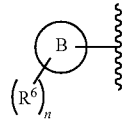

A is aromatic carbocycle, non-aromatic carbocycle, aromatic heterocycle, or non-aromatic heterocycle.
A preferred embodiment of A is aromatic carbocycle or aromatic heterocycle.
A more preferred embodiment of A includes phenyl, naphthyl, indanyl, pyridyl, pyrimidyl, pyrazolyl, piperidyl, piperazinyl, benzodioxolyl, benzothiophenyl, or thiazolyl.
B is aromatic carbocycle, non-aromatic carbocycle, aromatic heterocycle, non-aromatic heterocycle, or a single bond.
A preferred embodiment of B is aromatic carbocycle or aromatic heterocycle.
A more preferred embodiment of B includes phenyl, naphthyl, pyridyl, or pyrazolyl.
$R^2$ includes hydrogen, substituted or unsubstituted alkyl, substituted or unsubstituted alkylcarbonyl, substituted or unsubstituted alkyloxycarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyl, substituted or unsubstituted non-aromatic carbocyclylsulfonyl, substituted or unsubstituted aromatic heterocyclylsulfonyl, and substituted or unsubstituted non-aromatic heterocyclylsulfonyl.
A preferred embodiment of $R^2$ is hydrogen.
In the case that the substituent(s) of $R^2$ additionally have substituent(s), preferred substituent(s) of the substituent(s) of $R^2$ are halogen, hydroxy, amino, alkyl, monoalkylamino, dialkylamino, aromatic carbocyclyl, non-aromatic carbocyclyl, aromatic heterocyclyl, or non-aromatic heterocyclyl.
$R^3$ includes hydrogen, cyano, substituted or unsubstituted carbamoyl, substituted or unsubstituted alkyl, substituted or unsubstituted alkenyl, substituted or unsubstituted alkynyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylsulfonyl, substituted or unsubstituted non-aromatic carbocyclylsulfonyl, substituted or unsubstituted aromatic heterocyclylsulfonyl, and substituted or unsubstituted non-aromatic heterocyclylsulfonyl.
A preferred embodiment of $R^3$ includes substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

A more preferred embodiment of $R^3$ is substituted or unsubstituted alkyl.

In the case that the substituent(s) of $R^3$ additionally have substituent(s), preferred substituent(s) of the substituent(s) of $R^3$ are halogen, hydroxy, amino, alkyl, monoalkylamino, dialkylamino, aromatic carbocyclyl, non-aromatic carbocyclyl, aromatic heterocyclyl, or non-aromatic heterocyclyl.

A more preferred embodiment of $R^3$ includes trifluoromethyl.

$R^{4a}$ includes hydrogen, halogen, hydroxy, cyano, substituted or unsubstituted alkyl, substituted or unsubstituted non-aromatic carbocyclyl, and substituted or unsubstituted non-aromatic heterocyclyl.

A preferred embodiment of $R^{4a}$ includes hydrogen.

In the case that the substituent(s) of $R^{4a}$ additionally have substituent(s), preferred substituent(s) of the substituent(s) of $R^{4a}$ are halogen, hydroxy, amino, alkyl, monoalkylamino, dialkylamino, aromatic carbocyclyl, non-aromatic carbocyclyl, aromatic heterocyclyl, or non-aromatic heterocyclyl.

$R^{4b}$ includes hydrogen, halogen, hydroxy, cyano, substituted or unsubstituted alkyl, substituted or unsubstituted non-aromatic carbocyclyl, and substituted or unsubstituted non-aromatic heterocyclyl.

A preferred embodiment of $R^{4b}$ includes hydrogen.

In the case that the substituent(s) of $R^{4b}$ additionally have substituent(s), preferred substituent(s) of the substituent(s) of $R^{4b}$ are halogen, hydroxy, amino, alkyl, monoalkylamino, dialkylamino, aromatic carbocyclyl, non-aromatic carbocyclyl, aromatic heterocyclyl, or non-aromatic heterocyclyl.

$R^{4a}$ and $R^{4b}$ may be taken together with the adjacent carbon atom to form substituted or unsubstituted non-aromatic carbocycle or substituted or unsubstituted non-aromatic heterocycle, preferably to form cyclopropane, cyclobutane, cyclopentane, or cyclopropane.

The groups $R^5$ include each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyloxy, substituted or unsubstituted alkenylcarbonyloxy, substituted or unsubstituted alkynylcarbonyloxy, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by the formula: $-L^1-N=S(=O)(-R^{S1})-R^{S2}$, a group represented by the formula: $-L^1-S(=O)(=N-R^N)-R^{S1}$, a group represented by the formula: $-N=S(=N-R^N)(-R^{S1})-R^{S2}$, or a group represented by the formula: $-S(=N-R^N)_2-R^{S1}$.

In a preferred embodiment, $R^5$ includes each independently halogen, carboxy, cyano, substituted or unsubstituted carbamoyl, substituted or unsubstituted amino, substituted or unsubstituted ureido, substituted or unsubstituted sulfamoyl, substituted or unsubstituted alkyl, substituted or unsubstituted alkenyl, substituted or unsubstituted alkyloxy, substituted or unsubstituted alkylcarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, or substituted or unsubstituted alkylcarbonylamino.

In a more preferred embodiment, $R^5$ includes each independently halogen, cyano, substituted or unsubstituted carbamoyl, substituted or unsubstituted amino, substituted or unsubstituted sulfamoyl, substituted or unsubstituted alkyl, substituted or unsubstituted alkenyl, substituted or unsubstituted alkyloxy, substituted or unsubstituted alkylcarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted non-aromatic carbocyclyloxy, or substituted or unsubstituted non-aromatic heterocyclyloxy.

In the case that the substituent(s) of $R^5$ additionally have substituent(s), preferred substituent(s) of the substituent(s) of $R^5$ are halogen, cyano, hydroxy, carboxy, amino, ureido, alkyl, alkenyl, alkyloxy, alkylcarbonyl, alkylsulfonyl, monoalkylaminosulfonyl, monoalkylamino, dialkylamino, monoalkylcarbonylamino, monoalkyloxycarbonylamino, monoalkylsulfonylamino, monoalkylcarbamoyl, dialkylcarbamoyl, monoalkylsulfamoyl, dialkylsulfamoyl, aromatic carbocyclyl, non-aromatic carbocyclyl, aromatic heterocyclyl, or non-aromatic heterocyclyl.

In a more preferred specific embodiment, the groups $R^5$ include each independently a fluorine atom, a chlorine atom, cyano, methyl, ethyl, propyl, difluoromethyl, trifluoromethyl, hydroxymethyl, hydroxypropyl, methyloxy, difluoromethyloxy, ethyloxy, cyclopropylethyloxy, methylsulfonyl, carbamoyl, methylsulfonylamino, methylcarbonylamino, dimethylamino, cyclopropyl, cyclopentyl, phenyl, or benzyl.

The bonding position of $R^5$ is preferably the p-position of A.

The groups $R^6$ include each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyloxy, substituted or unsubstituted alkenylcarbonyloxy, substituted or unsubstituted alkynylcarbonyloxy, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by the formula: $-L^1-N=S(=O)(-R^{S1})-R^{S2}$, a group represented by the formula: $-L^1-S(=O)(=N-R^N)-R^{S1}$, a group represented by the formula: $-N=S(=N-R^N)(-R^{S1})-R^{S2}$, or a group represented by the formula: $-S(=N-R^N)_2-R^{S1}$.

In a preferred embodiment, $R^6$ includes each independently halogen, hydroxy, cyano, carboxy, substituted or unsubstituted carbamoyl, substituted or unsubstituted amino, substituted or unsubstituted ureido, substituted or unsubstituted sulfamoyl, substituted or unsubstituted alkyl, substituted or unsubstituted alkenyl, substituted or unsubstituted alkyloxy, substituted or unsubstituted alkylcarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl.

A more preferred embodiment of $R^6$ includes substituted or unsubstituted amino, substituted or unsubstituted alkyl, substituted or unsubstituted alkenyl, substituted or unsubstituted alkyloxy, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, or substituted or unsubstituted non-aromatic heterocyclyloxy.

In the case that the substituent(s) of $R^6$ additionally have substituent(s), preferred substituent(s) of the substituent(s) of $R^6$ are halogen, cyano, carboxy, amino, ureido, alkyl, alkenyl, alkyloxy, alkylsulfonyl, monoalkylaminosulfonyl, monoalkylamino, dialkylamino, monoalkylcarbonylamino, monoalkyloxycarbonylamino, monoalkylsulfonylamino, monoalkylcarbamoyl, dialkylcarbamoyl, monoalkylsulfamoyl, dialkylsulfamoyl, aromatic carbocyclyl, non-aromatic carbocyclyl, aromatic heterocyclyl, or non-aromatic heterocyclyl.

A more preferred specific embodiment of $R^6$ includes trifluoromethyl, trifluoromethyloxy, trifluoroethyloxy, trifluorobutyl, trifluorobutyloxy, trifluoropropyl, cyclopropyl, or phenyl.

The groups $R^{7a}$ include each independently hydrogen, halogen, hydroxy, cyano, substituted or unsubstituted amino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl.

A preferred embodiment of $R^{7a}$ is hydrogen.

In the case that the substituent(s) of $R^{7a}$ additionally have substituent(s), preferred substituent(s) of the substituent(s) of $R^{7a}$ include halogen, hydroxy, amino, alkyl, monoalkylamino, dialkylamino, aromatic carbocyclyl, non-aromatic carbocyclyl, aromatic heterocyclyl, or non-aromatic heterocyclyl.

The groups $R^{7b}$ include each independently hydrogen, halogen, hydroxy, cyano, substituted or unsubstituted amino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl.

A preferred embodiment of $R^{7b}$ is hydrogen.

In the case that the substituent(s) of $R^{7b}$ additionally have substituent(s), preferred substituent(s) of the substituent(s) of $R^{7b}$ include halogen, hydroxy, amino, alkyl, monoalkylamino, dialkylamino, aromatic carbocyclyl, non-aromatic carbocyclyl, aromatic heterocyclyl, or non-aromatic heterocyclyl.

$R^{7a}$ and $R^{7b}$ attached to the same carbon atom may be taken together with the adjacent carbon atom to form substituted or unsubstituted non-aromatic carbocycle or substituted or unsubstituted non-aromatic heterocycle.

$R^8$ includes hydrogen and substituted or unsubstituted alkyl.

A preferred embodiment of $R^8$ is hydrogen.

In the case that the substituent(s) of $R^8$ additionally have substituent(s), preferred substituent(s) of the substituent(s) of $R^8$ include halogen, hydroxy, amino, alkyl, monoalkylamino, dialkylamino, aromatic carbocyclyl, non-aromatic carbocyclyl, aromatic heterocyclyl, or non-aromatic heterocyclyl.

A more preferred embodiment of $R^8$ includes hydrogen or methyl.

$R^9$ includes hydrogen, substituted or unsubstituted amino, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyl, substituted or unsubstituted non-aromatic carbocyclylsulfonyl, substituted or unsubstituted aromatic heterocyclylsulfonyl, and substituted or unsubstituted non-aromatic heterocyclylsulfonyl.

A preferred embodiment of $R^9$ includes hydrogen, substituted or unsubstituted amino, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

In the case that the substituent(s) of $R^9$ additionally have substituent(s), preferred substituent(s) of the substituent(s) of $R^9$ include halogen, hydroxy, cyano, carboxy, amino, monoalkylamino, dialkylamino, alkyl, alkylsulfonyl, alkyloxycarbonyl, aromatic carbocyclyl, non-aromatic carbocyclyl, aromatic heterocyclyl, or non-aromatic heterocyclyl.

A more preferred embodiment of $R^9$ includes methyl, propyl, tert-butyl, pentyl, trifluoroethyl, amino, methylsulfonylmethyl, phenyl, cyclopropyl, cyclobutyl, cyclohexyl, tetrahydrofuryl, or isoxazolyl.

$R^{S1}$ and $R^{S2}$ include each independently hydrogen, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or, $R^{S1}$ and $R^{S2}$ bonding to the same sulfur atom may be taken together with the sulfur atom to form substituted or unsubstituted non-aromatic heterocycle.

In a preferred embodiment, $R^{S1}$ and $R^{S2}$ include each independently hydrogen or substituted or unsubstituted alkyl.

In a more preferred embodiment, $R^{S1}$ and $R^{S2}$ include each independently hydrogen.

In the case that each of the substituents of $R^{S1}$ and $R^{S2}$ additionally has a substituent, preferred substituents of the substituents of $R^{S1}$ and $R^{S2}$ include each independently halogen, hydroxy, amino, alkyl, alkyloxy, monoalkylamino, dialkylamino, aromatic carbocyclyl, non-aromatic carbocyclyl, aromatic heterocyclyl, or non-aromatic heterocyclyl.

$R^N$ includes each independently hydrogen, cyano, substituted or unsubstituted carbamoyl, substituted or unsubstituted alkyl, substituted or unsubstituted alkylcarbonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl.

In a preferred embodiment, $R^N$ includes each independently hydrogen or substituted or unsubstituted alkyl.

A more preferred embodiment of $R^N$ includes substituted or unsubstituted alkyl.

In the case that the substituent(s) of $R^N$ additionally have substituent(s), preferred substituent(s) of the substituent(s) of $R^N$ are halogen, hydroxy, amino, alkyl, alkyloxy, monoalkylamino, dialkylamino, aromatic carbocyclyl, non-aromatic carbocyclyl, aromatic heterocyclyl, or non-aromatic heterocyclyl.

The groups $L^1$ include each independently a single bond, alkylene, or C(=O).

In a preferred embodiment, $L^1$ includes each independently a single bond or alkylene.

A more preferred embodiment of $L^1$ includes a single bond.

m is an integer of 0 to 5.
A preferred embodiment of m is an integer of 0 to 3.
A more preferred embodiment of m is an integer of 0 to 2.
A particularly preferred embodiment of m is 0 or 1.
n is an integer of 0 to 5.
A preferred embodiment of n is an integer of 1 to 4.
A more preferred embodiment of n is an integer of 1 to 3.
A more preferred embodiment of n is 1 or 2.
A particularly preferred embodiment of n is 1.
p is an integer of 1 to 6.
A preferred embodiment of p is an integer of 1 to 3.
A more preferred embodiment of p is 1 or 2.
A particularly preferred embodiment of p is 1.

As particularly preferred compounds among the compounds represented by Formula (I), compounds selected from the group consisting of Example Compounds I-1, I-4, I-8, I-9, I-10, I-12, I-13, I-14, I-15, I-17, I-20, I-24, I-26, I-27, I-29, I-30, I-35, I-37, I-38, and I-42 are exemplified.

As particularly preferred compounds among the compounds represented by Formula (I), compounds selected from the group consisting of Example Compounds I-1, I-7, I-13, I-17, I-47, I-56, I-57, I-58, I-59, I-62, I-69, I-75, I-88, I-90, I-97, I-98, I-101, I-106, I-108, and I-114 are exemplified.

The compounds of the present invention are characterized by having MGAT2 inhibitory activity due to the configuration in which p in Formula (I) is an integer of 1 to 6, and substituted or unsubstituted alkylene (in particular, methylene) is formed.

One or more hydrogen, carbon and/or other atoms in the compounds represented by Formula (I) may be replaced with isotopes of hydrogen, carbon and/or other atoms respectively. Examples of isotopes include hydrogen, carbon, nitrogen, oxygen, phosphorus, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$ respectively. The compounds represented by Formula (I) include the compounds replaced with these isotopes. The compounds replaced with the above isotopes are useful as medicines and include all of radiolabeled compounds of the compound represented by Formula (I). A "method of radiolabeling" in the manufacture of the "radiolabeled compounds" is encompassed by the present invention, and is useful for studies on metabolized drug pharmacokinetics, studies on binding assay and/or diagnostic tools.

A radiolabeled compound of the compounds represented by Formula (I) can be prepared using well-known methods in the art. For example, a tritium-labeled compound represented by Formula (I) can be prepared by introducing a tritium into a certain compound represented by Formula (I), through a catalytic dehalogenation reaction using a tritium. This method comprises reacting an appropriately-halogenated precursor of the compound represented by Formula (I) with tritium gas in the presence of an appropriate catalyst, such as Pd/C, and in the presence or absence of a base. The other appropriate method of preparing a tritium-labeled compound can be referred to "Isotopes in the Physical and Biomedical Sciences, Vol. 1, Labeled Compounds (Part A), Chapter 6 (1987)". A $^{14}C$-labeled compound can be prepared by using a raw material having $^{14}C$.

The pharmaceutically acceptable salts of the compounds represented by Formula (I) include, for example, salts with alkaline metal (e.g., lithium, sodium, potassium or the like), alkaline earth metal (e.g., calcium, barium or the like), magnesium, transition metal (e.g., zinc, iron or the like), ammonia, organic bases (e.g., trimethylamine, triethylamine, dicyclohexylamine, ethanolamine, diethanolamine, triethanolamine, meglumine, ethylenediamine, pyridine, picoline, quinoline or the like) or amino acids, or salts with inorganic acids (e.g., hydrochloric acid, sulfuric acid, nitric acid, carbonic acid, hydrobromic acid, phosphoric acid, hydroiodic acid or the like) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Especially, salts with hydrochloric acid, sulfuric acid, phosphoric acid, tartaric acid, methanesulfonic acid and the like are included. These salts can be formed by the usual methods.

The compounds represented by Formula (I) or pharmaceutically acceptable salts thereof according to the present invention may form solvates (e.g., hydrates or the like), cocrystals and/or crystal polymorphs. The present invention encompasses those various solvates, cocrystals and crystal polymorphs. "Solvates" may be those wherein any numbers of solvent molecules (e.g., water molecules or the like) are coordinated with the compounds represented by Formula (I). When the compounds represented by Formula (I) or pharmaceutically acceptable salts thereof are allowed to stand in the atmosphere, the compounds may absorb water, resulting in attachment of adsorbed water or formation of hydrates. Recrystallization of the compounds represented by Formula (I) or pharmaceutically acceptable salts thereof may produce crystal polymorphs. "Cocrystal" means that the compound represented by Formula (I) or salt thereof and a counter molecule are present in the same crystal lattice, and a cocrystal with any number of counter molecules may be formed.

The compounds represented by Formula (I) or pharmaceutically acceptable salts thereof may form prodrugs. The present invention also encompasses such various prodrugs. Prodrugs are derivatives of the compounds of the present invention that have chemically or metabolically degradable groups, and compounds that are converted to the pharmaceutically active compounds of the present invention through solvolysis or under physiological conditions and in vivo. Prodrugs include compounds that are converted to the compounds represented by Formula (I) through enzymatic oxidation, reduction, hydrolysis or the like under physiological conditions and in vivo, compounds that are converted to the compounds represented by Formula (I) through hydrolysis by gastric acid etc., and the like. Methods for selecting and preparing suitable prodrug derivatives are described in, for example, "Design of Prodrugs, Elsevier, Amsterdam, 1985". Prodrugs themselves may have some activity.

When the compounds represented by Formula (I) or pharmaceutically acceptable salts thereof have hydroxy group(s), prodrugs include acyloxy derivatives and sulfonyloxy derivatives that are prepared by, for example, reacting compounds having hydroxy group(s) with suitable acyl halide, suitable acid anhydride, suitable sulfonyl chloride, suitable sulfonyl anhydride and mixed anhydride, or with a condensing agent. For example, they include $CH_3COO-$, $C_2H_5COO-$, tert-BuCOO—, $C_{15}H_{31}COO-$, PhCOO—, (m-NaOOCPh)COO—, $NaOOCCH_2CH_2COO-$, $CH_3CH(NH_2)COO-$, $CH_2N(CH_3)_2COO-$, $CH_3SO_3-$, $CH_3CH_2SO_3-$, $CF_3SO_3-$, $CH_2FSO_3-$, $CF_3CH_2SO_3-$, p-$CH_3O$-$PhSO_3-$, $PhSO_3-$ and p-$CH_3PhSO_3-$.

(General Procedure 1)

The compound of the present invention which is represented by Formula (I) (a12 below) can be produced, for example, through the following production method. In extraction, purification, and other operations, any process commonly performed therefor in organic chemistry experiments can be employed.

The compound of the present invention can be synthesized in accordance with a method known in the art.

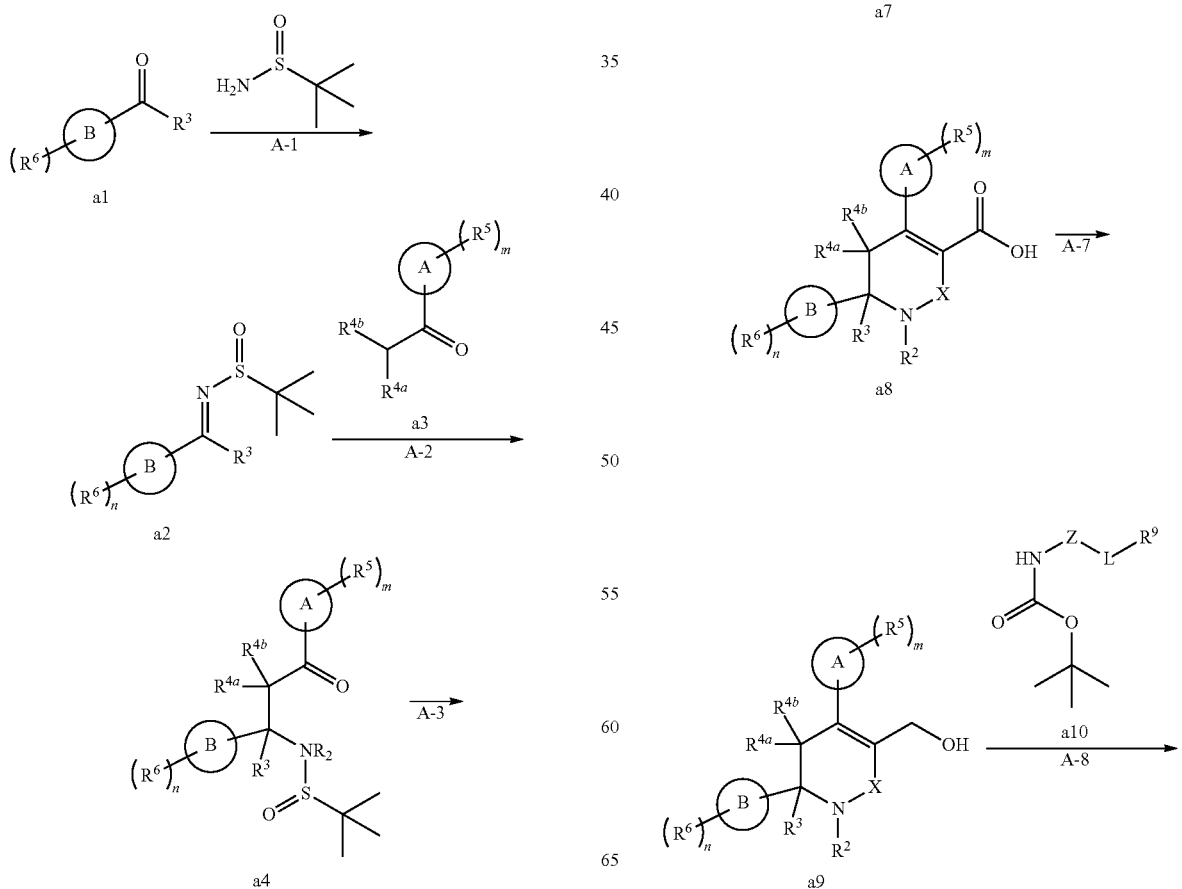

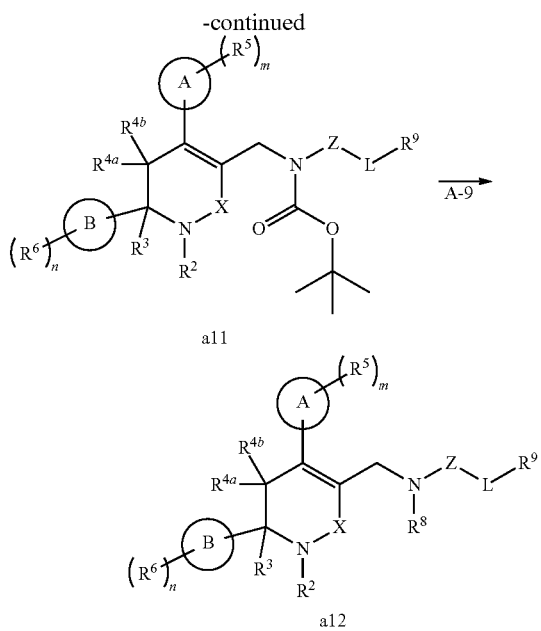

[Step A-1]

Compound a2 can be obtained by reacting Compound a1 and tert-butylsulfinamide with tetraisopropoxytitanium, tetraethoxytitanium, or the like.

The reaction temperature is 20° C. to 120° C., and preferably 50° C. to 80° C.

The reaction time is 1 hour to 12 hours, and preferably 3 hours to 6 hours.

As the reaction solvent, tetrahydrofuran, 2 methyltetrahydrofuran, toluene, dioxane and 1,2-dimethoxyethane are exemplified.

[Step A-2]

Compound a4 can be obtained by reacting a base such as lithium diisopropylamide and lithium hexamethyl disilazide and Ketone a3 followed by reacting the resultant with Compound a2.

The reaction temperature is −78° C. to −20° C. during the reaction between a base such as lithium diisopropylamide and lithium hexamethyl disilazide and Ketone a3 and the subsequent reaction with Compound a2.

The reaction time is 30 minutes to 2 hours during the reaction between a base and Ketone a3, and 1 to 5 hours during the subsequent reaction with Compound a2.

As the reaction solvent, tetrahydrofuran and diethyl ether are exemplified.

A compound in which $R^2$ is alkyl or the like can be synthesized by sequentially performing a reaction of alkylation or the like.

[Step A-3]

Compound a5 can be obtained by reacting Compound a4 and an acid or Lewis acid.

As the acid, hydrochloric acid-ethyl acetate, hydrochloric acid-methanol, hydrochloric acid-dioxane, sulfuric acid, formic acid, and trifluoroacetic acid are exemplified. As the Lewis acid, trimethylsilyl iodide, $BBr_3$, $AlCl_3$, and $BF_3.(Et_2O)$ are exemplified. 1 to 10 molar equivalents of the acid or Lewis acid with respect to Compound a4 can be used.

The reaction temperature is 0° C. to 60° C., and preferably 0° C. to 20° C.

The reaction time is 0.5 hour to 12 hours, and preferably 1 hour to 6 hours.

As the reaction solvent, methanol, ethanol, water, acetone, acetonitrile, and DMF are exemplified, and these reaction solvents can be used alone or in combination.

[Step A-4]

Compound a6 can be obtained by reacting Compound a5 and a carboxylic acid chloride, sulfonic acid chloride, thiocarboxylic acid chloride or the like in the presence of a base.

As the base, pyridine, DIEA, potassium carbonate, sodium hydrogen carbonate, sodium hydride, and sodium hydroxide are exemplified.

The reaction temperature is 0° C. to 150° C., and preferably 20° C. to 100° C.

The reaction time is 0.5 hour to 120 hours, and preferably 1 hour to 72 hours.

As the reaction solvent, acetonitrile, tetrahydrofuran, toluene, and dichloromethane are exemplified.

Step A-4' can be employed as an alternative method to Step A-4.

[Step A-4']

Compound a6 can be obtained by reacting Compound a5 and a carboxylic acid or the like in the presence of a condensing agent, under the action of a base, as necessary.

As the condensing agent, dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, and HATU are exemplified. 1 to 5 molar equivalents of the condensing agent with respect to Compound a5 can be used.

As the base, triethylamine and diisopropylethylamine are exemplified.

The reaction temperature is −20° C. to 60° C., and preferably 0° C. to 30° C.

The reaction time is 0.1 hour to 24 hours, and preferably 1 hour to 12 hours.

As the reaction solvent, DMF, DMA, NMP, tetrahydrofuran, dioxane, dichloromethane, and acetonitrile are exemplified, and these reaction solvents can be used alone or in combination.

[Step A-5]

Compound a7 can be obtained by reacting Compound a6 and a base.

As the base, piperidine, pyrrolidine, triethylamine, diisopropylethylamine, sodium methoxide, and sodium ethoxide are exemplified.

The reaction temperature is 0° C. to 150° C.

The reaction time is 1 hour to 72 hours.

As the reaction solvent, methanol, ethanol, and tetrahydrofuran are exemplified.

[Step A-6]

Compound a8 can be obtained by reacting Compound a7 and an acid or Lewis acid. As the acid, hydrochloric acid-ethyl acetate, hydrochloric acid-methanol, hydrochloric acid-dioxane, sulfuric acid, formic acid, and trifluoroacetic acid are exemplified. As the Lewis acid, trimethylsilyl iodide, $BBr_3$, $AlCl_3$, and $BF_3.(Et_2O)$ are exemplified.

The reaction temperature is 0° C. to 60° C., and preferably 0° C. to 20° C.

The reaction time is 0.5 hour to 12 hours, and preferably 1 hour to 6 hours.

As the reaction solvent, methanol, ethanol, water, acetone, acetonitrile, DMF, and dichloromethane are exemplified, and these reaction solvents can be used alone or in combination.

[Step A-7]

Compound a9 can be obtained by reacting Compound a8 with a base and a chloroformate followed by reacting the resultant with a reducing agent.

As the base, triethylamine, pyridine, DIEA, potassium carbonate, sodium hydrogen carbonate, sodium hydride, and sodium hydroxide are exemplified.

As the reducing agent, sodium borohydride, lithium borohydride, and aluminum hydride are exemplified. 1 to 10 molar equivalents of the reducing agent with respect to Compound a8 can be used.

The reaction temperature is 0° C. to 60° C., and preferably 0° C. to 20° C.

The reaction time is 0.5 hour to 24 hours, and preferably 1 hour to 20 hours.

As the reaction solvent, acetonitrile, tetrahydrofuran, toluene, dichloromethane, methanol, ethanol, water, acetonitrile, and DMF are exemplified, and these reaction solvents can be used alone or in combination.

[Step A-8]

Compound a11 can be obtained by reacting Compound a9 and Compound a10 in the presence of triphenylphosphine or the like and a condensing agent.

As the condensing agent, DEAD and DIAD are exemplified. 1 to 5 molar equivalents of the condensing agent with respect to Compound a9 can be used.

The reaction temperature is 0° C. to 60° C., and preferably 10° C. to 40° C.

The reaction time is 0.5 hour to 12 hours, and preferably 1 hour to 6 hours.

As the reaction solvent, tetrahydrofuran, dioxane, ethyl acetate, toluene, and acetonitrile are exemplified, and these reaction solvents can be used alone or in combination.

[Step A-9]

Compound a12 can be obtained by reacting Compound a11 and an acid or Lewis acid.

As the acid, hydrochloric acid-ethyl acetate, hydrochloric acid-methanol, hydrochloric acid-dioxane, sulfuric acid, formic acid, and trifluoroacetic acid are exemplified. As the Lewis acid, trimethylsilyl iodide, $BBr_3$, $AlCl_3$, and $BF_3 \cdot (Et_2O)$ are exemplified. 1 to 10 molar equivalents of the acid or Lewis acid with respect to Compound a11 can be used.

The reaction temperature is 0° C. to 60° C., and preferably 0° C. to 20° C.

The reaction time is 0.5 hour to 24 hours, and preferably 1 hour to 20 hours.

As the reaction solvent, methanol, ethanol, water, acetone, acetonitrile, DMF, and dichloromethane are exemplified, and these reaction solvents can be used alone or in combination.

A compound in which $R^8$ is alkyl or the like can be synthesized by sequentially performing a reaction of alkylation or the like.

(General Procedure 2)

The compound of the present invention which is represented by Formula (I) (a18 below) can be produced, for example, through the following production method. In extraction, purification, and other operations, any process commonly performed therefor in organic chemistry experiments can be employed.

The compound of the present invention can be synthesized in accordance with a method known in the art.

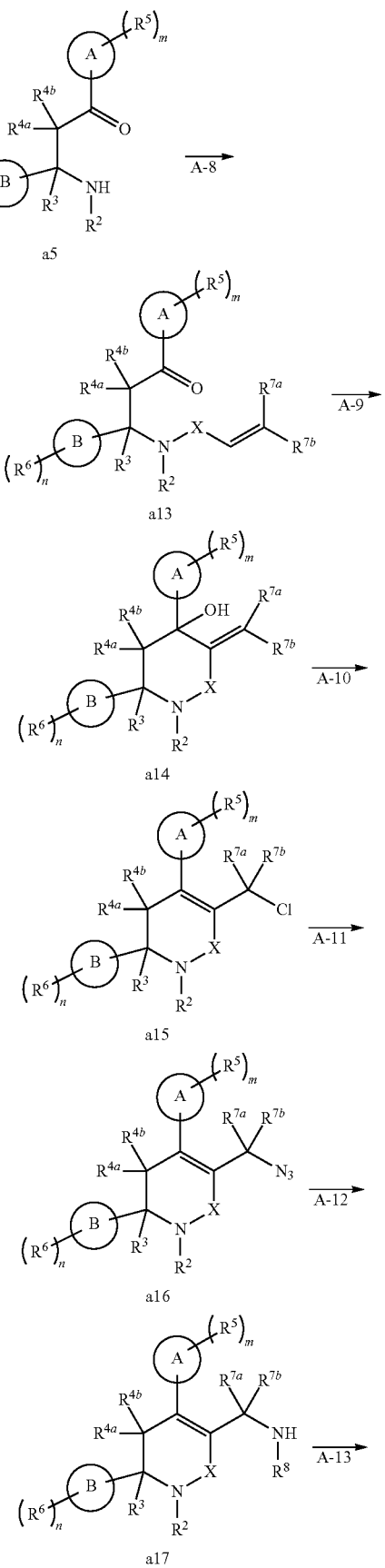

-continued

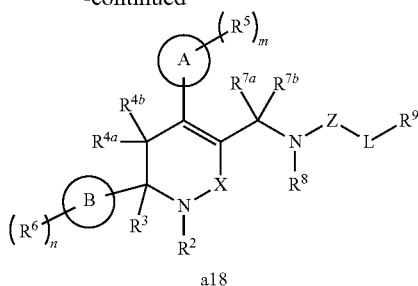

a18

[Step A-8]
Compound a13 can be obtained by reacting Compound a5 and a carboxylic acid chloride, sulfonic acid chloride, thiocarboxylic acid chloride or the like in the presence of a base.

As the base, pyridine, DIEA, potassium carbonate, sodium hydrogen carbonate, sodium hydride, and sodium hydroxide are exemplified.

The reaction temperature is 0° C. to 150° C., and preferably 20° C. to 100° C.

The reaction time is 0.5 hour to 48 hours, and preferably 1 hour to 24 hours.

As the reaction solvent, acetonitrile, tetrahydrofuran, toluene, and dichloromethane are exemplified.

Step A-8' can be employed as an alternative method to Step A-8.

[Step A-8']
Compound a13 can be obtained by reacting Compound a5 and a carboxylic acid or the like in the presence of a condensing agent, under the action of a base, as necessary.

As the condensing agent, dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, and HATU are exemplified. 1 to 5 molar equivalents of the condensing agent with respect to Compound a5 can be used.

As the base, triethylamine, and diisopropylethylamine are exemplified.

The reaction temperature is −20° C. to 60° C., and preferably 0° C. to 30° C.

The reaction time is 0.1 hour to 24 hours, and preferably 1 hour to 12 hours.

As the reaction solvent, DMF, DMA, NMP, tetrahydrofuran, dioxane, dichloromethane, and acetonitrile are exemplified, and these reaction solvents can be used alone or in combination.

[Step A-9]
Compound a14 can be obtained by reacting Compound a13 and a cyclic amine or the like.

As the cyclic amine, 4-diazabicyclo[2,2,2]octane, quinuclidine, N,N-dimethyl-4-aminopyridine, and diazabicycloundecene are exemplified.

The reaction temperature is 20° C. to 150° C., and preferably 20° C. to 100° C.

The reaction time is 1 hour to 168 hours, and preferably 1 hour to 96 hours.

As the reaction solvent, dioxane, acetonitrile, tetrahydrofuran, toluene, dichloromethane, water, and DMSO are exemplified.

[Step A-10]
Compound a15 can be obtained by reacting Compound a14, a halogenating agent, and, as necessary, a base.

A compound in which $X^2$ is a chlorine atom can be obtained by using oxalyl dichloride, thionyl chloride, phosphorus oxychloride or the like as the halogenating agent. 1 to 5 molar equivalents of the halogenating agent with respect to Compound a8 can be used. Alternatively, a compound in which $X^2$ is a bromine atom can be obtained under the action of a brominating agent such as phosphorus tribromide.

As the base, triethylamine, diisopropylethylamine, pyridine, and 2,6-lutidine are exemplified.

The reaction temperature is 0° C. to 60° C., and preferably 0° C. to 40° C.

The reaction time is 0.5 hour to 24 hours, and preferably 1 hour to 12 hours.

As the reaction solvent, acetonitrile, tetrahydrofuran, toluene, dichloromethane, and DMF are exemplified, and these reaction solvents can be used alone or in combination.

[Step A-11]
Compound a16 can be obtained by reacting Compound a15 and sodium azide.

The reaction temperature is 0° C. to 60° C., and preferably 0° C. to 40° C.

The reaction time is 0.5 hour to 24 hours, and preferably 1 hour to 8 hours.

As the reaction solvent, acetonitrile, DMSO, and DMF are exemplified.

[Step A-12]
Compound a17 can be obtained by reacting Compound a16, a trivalent phosphorus compound, and water.

As the trivalent phosphorus compound, triphenylphosphine, and trimethylphosphine are exemplified. 1 to 10 molar equivalents of the trivalent phosphorus compound with respect to Compound a16 can be used.

The reaction time is 0.1 hour to 48 hours, and preferably 0.5 hour to 24 hours.

As the reaction solvent, tetrahydrofuran, diethyl ether, dichloroethane, and acetonitrile are exemplified.

A compound in which $R^8$ is alkyl or the like can be synthesized by sequentially performing a reaction of alkylation or the like.

[Step A-13]
Compound a18 can be obtained by reacting Compound a17 and a carboxylic anhydride, or by reacting Compound a17 and carboxylic acid chloride, sulfonic acid chloride, thiocarboxylic acid chloride or the like in the presence of a base.

As the base, pyridine, DIEA, potassium carbonate, sodium hydrogen carbonate, sodium hydride, and sodium hydroxide are exemplified.

The reaction temperature is 0° C. to 60° C., and preferably 0° C. to 40° C.

The reaction time is 0.5 hour to 10 hours, and preferably 1 hour to 5 hours.

As the reaction solvent, methanol, acetonitrile, tetrahydrofuran, toluene, and dichloromethane are exemplified.

Step A-13' can be employed as an alternative method to Step A-13.

[Step A-13']
Compound a18 can be obtained by reacting Compound a17 and a carboxylic acid or the like in the presence of a condensing agent, under the action of a base, as necessary.

As the condensing agent, dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, and HATU are exemplified. 1 to 5 molar equivalents of the condensing agent with respect to Compound a17 can be used.

As the base, triethylamine, and diisopropylethylamine are exemplified.

The reaction temperature is −20° C. to 60° C., and preferably 0° C. to 30° C.

The reaction time is 0.1 hour to 24 hours, and preferably 1 hour to 12 hours.

As the reaction solvent, DMF, DMA, NMP, tetrahydrofuran, dioxane, dichloromethane, and acetonitrile are exemplified, and these reaction solvents can be used alone or in combination.

(General Procedure 3)

The compound of the present invention which is represented by Formula (I) in which p is 2 to 6 (a20 below) can be produced, for example, through the following production method. In extraction, purification, and other operations, any process commonly performed therefor in organic chemistry experiments can be employed.

The compound of the present invention can be synthesized in accordance with a method known in the art.

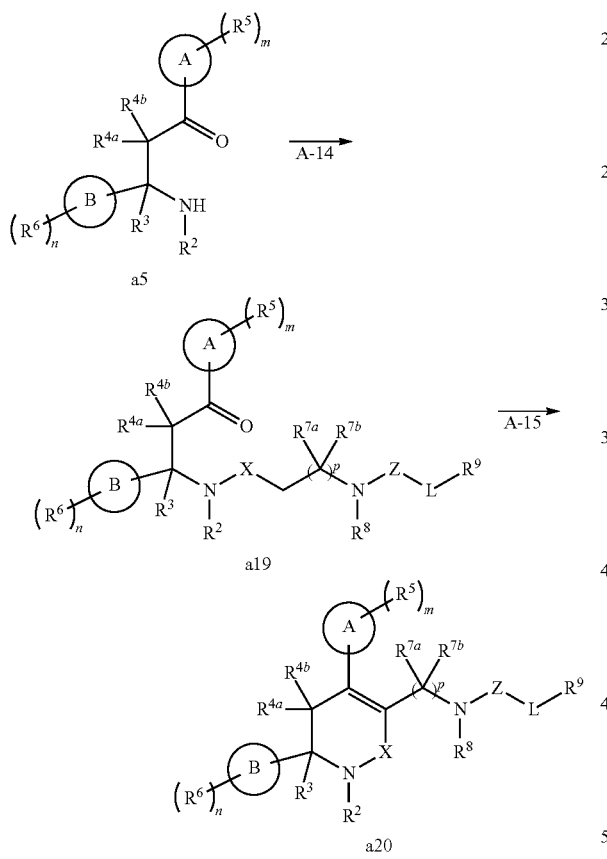

[Step A-14']

Compound a19 can be obtained by reacting Compound a5 and a carboxylic acid or the like in the presence of a condensing agent, under the action of a base, as necessary.

As the condensing agent, dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, and HATU are exemplified. 1 to 5 molar equivalents of the condensing agent with respect to Compound a5 can be used.

As the base, triethylamine, and diisopropylethylamine are exemplified.

The reaction temperature is −20° C. to 60° C., and preferably 0° C. to 30° C.

The reaction time is 0.1 hour to 24 hours, and preferably 1 hour to 12 hours.

As the reaction solvent, DMF, DMA, NMP, tetrahydrofuran, dioxane, dichloromethane, and acetonitrile are exemplified, and these reaction solvents can be used alone or in combination.

[Step A-15]

Compound a20 can be obtained by reacting Compound a19 and a base.

As the base, piperidine, pyrrolidine, triethylamine, diisopropylethylamine, sodium methoxide, and sodium ethoxide are exemplified.

The reaction temperature is 0° C. to 150° C.

The reaction time is 1 hour to 72 hours.

As the reaction solvent, methanol, ethanol, and tetrahydrofuran are exemplified.

(General Procedure 4)

The compound of the present invention which is represented by Formula (I) (a11 below) can be produced, for example, through the following production method.

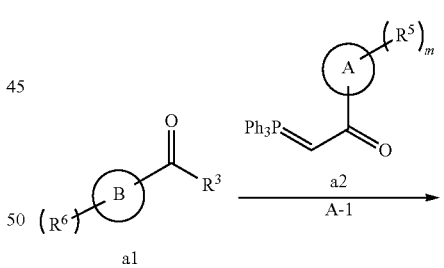

[Step A-14]

Compound a19 can be obtained by reacting Compound a5 and a carboxylic acid chloride, sulfonic acid chloride, thiocarboxylic acid chloride or the like in the presence of a base.

As the base, pyridine, DIEA, potassium carbonate, sodium hydrogen carbonate, sodium hydride, and sodium hydroxide are exemplified.

The reaction temperature is 0° C. to 150° C., and preferably 20° C. to 100° C.

The reaction time is 0.5 hour to 120 hours, and preferably 1 hour to 72 hours.

As the reaction solvent, acetonitrile, tetrahydrofuran, toluene, and dichloromethane are exemplified.

Step A-14' can be employed as an alternative method to Step A-14.

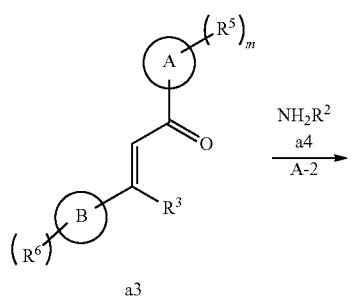

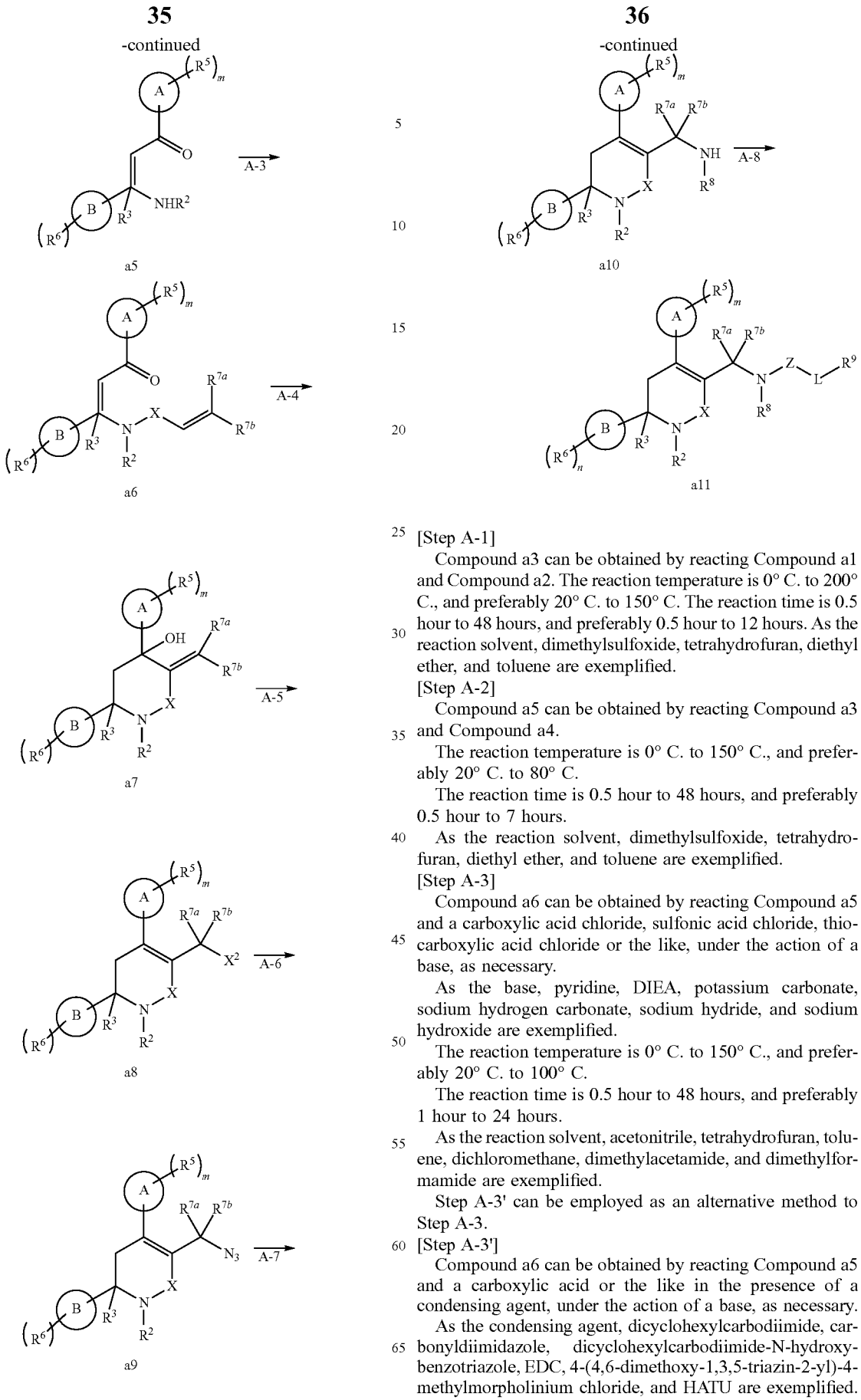

[Step A-1]

Compound a3 can be obtained by reacting Compound a1 and Compound a2. The reaction temperature is 0° C. to 200° C., and preferably 20° C. to 150° C. The reaction time is 0.5 hour to 48 hours, and preferably 0.5 hour to 12 hours. As the reaction solvent, dimethylsulfoxide, tetrahydrofuran, diethyl ether, and toluene are exemplified.

[Step A-2]

Compound a5 can be obtained by reacting Compound a3 and Compound a4.

The reaction temperature is 0° C. to 150° C., and preferably 20° C. to 80° C.

The reaction time is 0.5 hour to 48 hours, and preferably 0.5 hour to 7 hours.

As the reaction solvent, dimethylsulfoxide, tetrahydrofuran, diethyl ether, and toluene are exemplified.

[Step A-3]

Compound a6 can be obtained by reacting Compound a5 and a carboxylic acid chloride, sulfonic acid chloride, thiocarboxylic acid chloride or the like, under the action of a base, as necessary.

As the base, pyridine, DIEA, potassium carbonate, sodium hydrogen carbonate, sodium hydride, and sodium hydroxide are exemplified.

The reaction temperature is 0° C. to 150° C., and preferably 20° C. to 100° C.

The reaction time is 0.5 hour to 48 hours, and preferably 1 hour to 24 hours.

As the reaction solvent, acetonitrile, tetrahydrofuran, toluene, dichloromethane, dimethylacetamide, and dimethylformamide are exemplified.

Step A-3' can be employed as an alternative method to Step A-3.

[Step A-3']

Compound a6 can be obtained by reacting Compound a5 and a carboxylic acid or the like in the presence of a condensing agent, under the action of a base, as necessary.

As the condensing agent, dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, and HATU are exemplified.

1 to 5 molar equivalents of the condensing agent with respect to Compound a5 can be used.

As the base, triethylamine, and diisopropylethylamine are exemplified.

The reaction temperature is −20° C. to 60° C., and preferably 0° C. to 30° C.

The reaction time is 0.1 hour to 24 hours, and preferably 1 hour to 12 hours.

As the reaction solvent, DMF, DMA, NMP, tetrahydrofuran, dioxane, dichloromethane, and acetonitrile are exemplified, and these reaction solvents can be used alone or in combination.

[Step A-4]

Compound a7 can be obtained by reacting Compound a6 and a cyclic amine or the like.

As the cyclic amine, 4-diazabicyclo[2,2,2]octane, quinuclidine, N,N-dimethyl-4-aminopyridine, and diazabicycloundecene are exemplified.

The reaction temperature is 20° C. to 150° C., and preferably 20° C. to 100° C.

The reaction time is 1 hour to 150 hours, and preferably 1 hour to 24 hours.

As the reaction solvent, dioxane, acetonitrile, tetrahydrofuran, toluene, dichloromethane, water, and DMSO are exemplified.

[Step A-5]

Compound a8 can be obtained by reacting Compound a7, a halogenating agent, and, as necessary, a base.

A compound in which $X^2$ is a chlorine atom can be obtained by using oxalyl dichloride, thionyl chloride, phosphorus oxychloride or the like as the halogenating agent. 1 to 5 molar equivalents of the halogenating agent with respect to Compound a8 can be used. Alternatively, a compound in which $X^2$ is a bromine atom can be obtained under the action of a brominating agent such as phosphorus tribromide.

As the base, triethylamine, diisopropylethylamine, pyridine, and 2,6-lutidine are exemplified.

The reaction temperature is 0° C. to 60° C., and preferably 0° C. to 40° C.

The reaction time is 0.5 hour to 24 hours, and preferably 1 hour to 12 hours.

As the reaction solvent, acetonitrile, tetrahydrofuran, toluene, dichloromethane, and DMF are exemplified, and these reaction solvents can be used alone or in combination.

[Step A-6]

Compound a9 can be obtained by reacting Compound a8 and sodium azide.

The reaction temperature is 0° C. to 60° C., and preferably 0° C. to 40° C.

The reaction time is 0.5 hour to 24 hours, and preferably 1 hour to 8 hours.

As the reaction solvent, acetonitrile, DMSO, and DMF are exemplified.

[Step A-7]

Compound a10 can be obtained by reacting Compound a9, a trivalent phosphorus compound, and water.

As the trivalent phosphorus compound, triphenylphosphine, and trimethylphosphine are exemplified. 1 to 10 molar equivalents of the trivalent phosphorus compound with respect to Compound a9 can be used.

The reaction time is 0.1 hour to 48 hours, and preferably 0.5 hour to 24 hours.

As the reaction solvent, tetrahydrofuran, diethyl ether, dichloroethane, and acetonitrile are exemplified.

A compound in which $R^8$ is alkyl or the like can be synthesized by sequentially performing a reaction of alkylation or the like.

[Step A-8]

Compound a11 can be obtained by reacting Compound a10 and a carboxylic anhydride, or by reacting Compound a10 and carboxylic acid chloride, sulfonic acid chloride, thiocarboxylic acid chloride or the like in the presence of a base.

As the base, pyridine, DIEA, potassium carbonate, sodium hydrogen carbonate, sodium hydride, and sodium hydroxide are exemplified.

The reaction temperature is 0° C. to 60° C., and preferably 0° C. to 40° C.

The reaction time is 0.5 hour to 10 hours, and preferably 1 hour to 5 hours.

As the reaction solvent, methanol, acetonitrile, tetrahydrofuran, toluene, and dichloromethane are exemplified.

Step A-8' can be employed as an alternative method to Step A-8.

[Step A-8']

Compound a11 can be obtained by reacting Compound a10 and a carboxylic acid or the like in the presence of a condensing agent, under the action of a base, as necessary.

As the condensing agent, dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, and HATU are exemplified. 1 to 5 molar equivalents of the condensing agent with respect to Compound a10 can be used.

As the base, triethylamine, and diisopropylethylamine are exemplified.

The reaction temperature is −20° C. to 60° C., and preferably 0° C. to 30° C.

The reaction time is 0.1 hour to 24 hours, and preferably 1 hour to 12 hours.

As the reaction solvent, DMF, DMA, NMP, tetrahydrofuran, dioxane, dichloromethane, and acetonitrile are exemplified, and these reaction solvents can be used alone or in combination.

The compounds of the present invention have MGAT2 inhibitory activity, and are useful as a prophylactic agent and/or therapeutic agent for, for example, obesity, metabolic syndrome, hyperlipidemia, hypertriglyceridemia, hyper-VLDL-triglyceridemia, hyperfattyacidemia, diabetes mellitus, or arteriosclerosis.

The compounds of the present invention have not only MGAT2 inhibitory activity but also usefulness as a medicine, and have any or all of the following superior features:
a) having high metabolic stability,
b) exhibiting high solubility,
c) having less risk of phototoxicity,
d) having less risk of hepatotoxicity,
e) having less risk of kidney toxicity,
f) having less risk of gastrointestinal disorders,
g) having less risk of drug interaction,
h) having high oral absorbability,
i) having small clearance,
j) having high distribution to a targeted tissue,
k) having intense enzymatic activity,
l) causing less induction of drug-metabolizing enzyme,
m) having intense efficacy, and
n) having high selectivity of MGAT2 inhibitory activity.

The pharmaceutical composition of the present invention can be administered by using either an oral method or a parenteral method. As the method for parenteral administration, for example, dermal, subcutaneous, intravenous, intraarterial, intramuscular, intraperitoneal, transmucosal, inhalation, transnasal, ophthalmic, inner ear, and vaginal administrations are exemplified.

In the case of oral administration, any usual dosage form such as a solid formulation for internal application (e.g., a tablet, powder, granule, capsule, pill, film etc.) and a liquid formulation for internal application (e.g., a suspension, emulsion, elixir, syrup, lemonade, spirit, aromatic water, extract, decoction, tincture etc.) can be prepared for administration in accordance with a conventional method. The tablet may be a sugar-coated tablet, film-coated tablet, enteric-coated tablet, sustained-release tablet, troche tablet, sublingual tablet, buccal tablet, chewable tablet, or orally dispersing tablet; the powder or granule may be a dry syrup; and the capsule may be a soft capsule, micro capsule or sustained-release capsule.

In the case of parenteral administration, any usual dosage form such as an injection, infusion, and formulation for external application (e.g., an eye drop, nose drop, ear drop, aerosol, inhalation, lotion, impregnation, liniment, mouthwash, enema, ointment, plaster, jelly, cream, patch, cataplasm, external powder or suppository etc.) can be suitably administered. The injection may be an emulsion of, for example, O/W, W/O, O/W/O, or W/O/W type.

A pharmaceutical composition can be prepared by mixing an effective amount of the compound of the present invention with various pharmaceutical additives including excipients, binders, disintegrators, and lubricants suitable for the dosage form, as necessary. In addition, a pharmaceutical composition for a pediatric patient, for a geriatric patient, for a patient with severe condition, or for surgery can be prepared through appropriate modification of the effective amount, dosage form, and/or various pharmaceutical additives for the compound of the present invention. The pharmaceutical composition for a pediatric patient is preferably administered to a patient younger than 12 or 15 years old. The pharmaceutical composition for a pediatric patient may be administered to a patient younger than 27 days old, at the age of 28 days to 23 months, at the age of 2 years to 11 years, or at the age of 12 years to 16 years or 18 years. The pharmaceutical composition for a geriatric patient is preferably administered to a patient aged 65 years or older.

It is desirable to set the dosage of the pharmaceutical composition of the present invention in consideration of, for example, the age and body weight of a patient, the type and degree of the disease, and the route of administration. In the case of oral administration, the dosage is usually 0.05 to 100 mg/kg/day, and preferably in the range of 0.1 to 10 mg/kg/day. In the case of parenteral administration, the dosage is usually 0.005 to 10 mg/kg/day, and preferably in the range of 0.01 to 1 mg/kg/day, though the dosage largely varies depending on the route of administration. The dosage can be administered in one to several divided portions per day.

The dosage of a pharmaceutical agent to be combined can be appropriately selected on the basis of doses used in clinical practices. The blend ratio between the compound of the present invention and a pharmaceutical agent to be combined can be appropriately selected, for example, in accordance with the subject for administration, route of administration, disease of interest, symptoms, and combination. In the case that the subject for administration is a human, for example, 0.01 to 100 parts by weight of a pharmaceutical agent with respect to 1 part by weight of the compound of the present invention can be combined for use.

In this description, meanings of each abbreviation are as follows:
DIAD: Diisopropyl azodicarboxylate
DIEA: N,N-diisopropylethylamine
DMA: Dimethylacetamide
DMF: N,N-dimethylformamide
DMSO: Dimethylsulfoxide
DTT: Dithiothreitol
Et: Ethyl
HATU: O-(7-Azabenzotriazol-1-yl)-1,1,3,3-tetramethyluronium hexafluorophosphate
NMP: N-Methylpyrrolidone

EXAMPLES

The present invention will be described in more detail with reference to, but not limited to, the following Examples and Reference Examples, and Test Examples.

NMR analysis of each Example was performed by 300 MHz using DMSO-$d_6$ or CDCl$_3$.

Example 1 Synthesis of Compound I-1

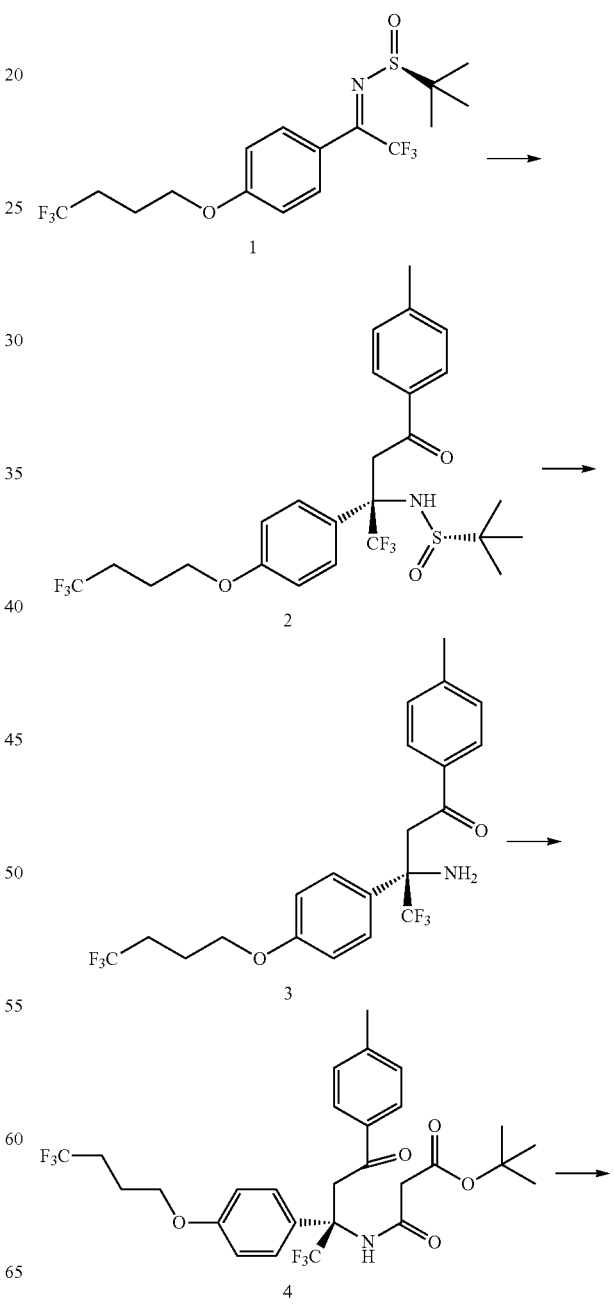

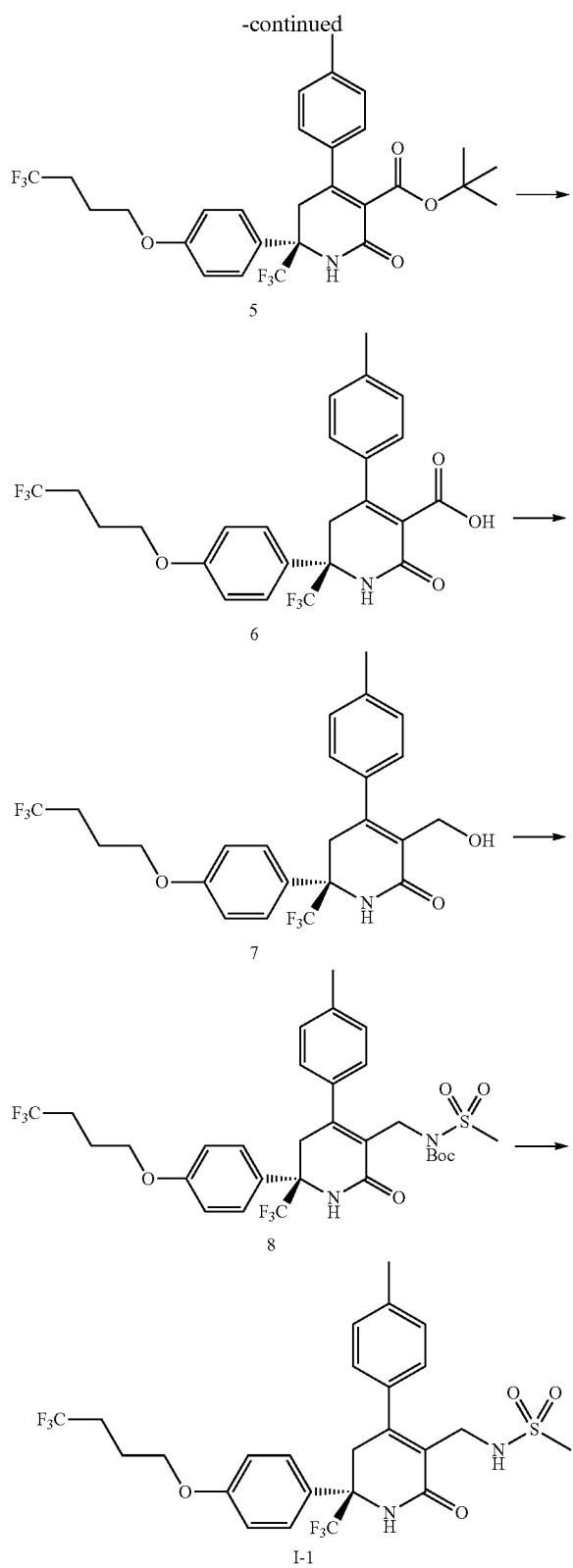

was added dropwise thereto, and the mixture was warmed from −78° C. to −30° C. with stirring over 1 hour. Thereto, 1-(4-methylphenyl)ethanone (3.06 mL, 22.96 mmol) was added dropwise at −78° C., and the mixture was then stirred for 30 minutes. A solution of Compound 1 (described in WO2014/193884) (4.63 g, 11.48 mmol) in tetrahydrofuran (46 mL) was added, and the mixture was stirred at −78° C. for 2 hours. An aqueous solution of ammonium chloride was added, and the mixture was warmed to room temperature. Water was added, extraction was performed with ethyl acetate, and the organic layer was dried over anhydrous magnesium sulfate. The solvent was evaporated under reduced pressure, and the obtained residue was purified by silica gel column chromatography (hexane-ethyl acetate) to afford Compound 2 (2.01 g, yield 33%). 1H-NMR (CDCl3) δ: 1.56 (s, 9H), 2.03-2.10 (m, 2H), 2.27-2.37 (m, 2H), 2.42 (s, 3H), 3.78 (d, J=16.8 Hz, 1H), 3.97 (d, J=16.8 Hz, 1H), 4.04 (t, J=5.9 Hz, 2H), 6.61 (s, 1H), 6.92 (d, J=8.6 Hz, 2H), 7.27 (d, J=8.8 Hz, 6H), 7.59 (d, J=8.8 Hz, 2H), 7.84 (d, J=8.6 Hz, 2H).

Step 2 Synthesis of Compound 3

Compound 2 (2.01 g, 3.73 mmol) was dissolved in dioxane (12 mL), and a 4 mol/L solution of hydrochloric acid-dioxane (4.67 mL, 18.67 mmol) was added, and the mixture was stirred at room temperature for 18 hours. The solvent was evaporated under reduced pressure, and the obtained residue was added to a saturated aqueous solution of sodium bicarbonate, and extracted with ethyl acetate, and the organic layer was dried over anhydrous magnesium sulfate. The solvent was evaporated under reduced pressure, and the resultant was then used directly in the next reaction.

Step 3 Synthesis of Compound 4

Under nitrogen atmosphere, triphenylphosphine (1.66 g, 6.35 mmol) was added to a solution of mono-tert-butyl malonate (0.533 mL, 3.46 mmol) in dichloromethane (5 mL), and 2,2,2-trichloroacetonitrile (0.405 mL, 4.04 mmol) was added dropwise thereto under ice cooling, and the mixture was stirred at 28° C. for 1 hour. The reaction solution was cooled in ice, and a solution of Compound 3 (500 mg, 1.15 mmol) in dichloromethane (10 mL) and pyridine (0.933 mL, 11.54 mmol) were added dropwise thereto, and the mixture was stirred at room temperature for 16 hours. The solvent was evaporated under reduced pressure, and the obtained residue was purified by silica gel column chromatography (hexane-ethyl acetate) to afford Compound 4 (535 mg, yield in two steps 81%).

1H-NMR (CDCl3) δ: 1.52 (s, 9H), 2.00-2.09 (m, 2H), 2.24-2.35 (m, 2H), 2.40 (s, 3H), 3.27 (s, 2H), 3.83 (d, J=17.1 Hz, 1H), 4.01 (t, J=5.9 Hz, 2H), 4.73 (d, J=17.1 Hz, 1H), 6.90 (d, J=8.9 Hz, 2H), 7.24 (d, J=8.2 Hz, 2H), 7.46 (d, J=8.9 Hz, 2H), 7.81 (d, J=8.2 Hz, 2H), 8.45 (s, 1H).

Step 4 Synthesis of Compound 5

Compound 4 (0.809 g, 1.41 mmol) was dissolved in methanol (32 mL), and a 1 mol/L methanol solution of sodium methoxide (2.81 mL, 2.81 mmol) was added under ice cooling, and the mixture was stirred under ice cooling for 9 minutes. A 1 mol/L aqueous solution of hydrochloric acid was added, and extraction was performed with ethyl acetate. The organic layer was washed by brine, and dried over anhydrous magnesium sulfate. The solvent was evaporated under reduced pressure, and the obtained crude product was then dissolved in acetonitrile (18 mL), and a 2 mol/L aqueous solution of hydrochloric acid (2 mL) was added dropwise under ice cooling, and the mixture was stirred at room temperature for 15 hours. The solvent was evaporated under reduced pressure, and the obtained residue was puri- Step 1 Synthesis of Compound 2

Under nitrogen atmosphere, a solution of diisopropylamine (3.23 mL, 22.96 mmol) in tetrahydrofuran (46.3 mL) was cooled to −78° C. with dry ice-acetone. A 1.63 mol/L solution of n-butyllithium-hexane (14.08 mL, 22.96 mmol)

fied by silica gel column chromatography (hexane-ethyl acetate) to afford Compound 5 (655 mg, yield 84%).

1H-NMR (CDCl3) δ: 1.30 (s, 9H), 2.02-2.10 (m, 2H), 2.27-2.36 (m, 5H), 3.23 (d, J=17.3 Hz, 1H), 3.52 (d, J=17.3 Hz, 1H), 4.02 (t, J=5.9 Hz, 2H), 6.16 (s, 1H), 6.90 (d, J=8.8 Hz, 2H), 7.11-7.17 (m, 4H), 7.40 (d, J=8.8 Hz, 2H).

Step 5 Synthesis of Compound 6

Compound 5 (650 mg, 1.17 mmol) was dissolved in dichloromethane (4 mL), and trifluoroacetic acid (2.0 mL, 26.0 mmol) was added dropwise under ice cooling, and the mixture was stirred at room temperature for 2 hours. The solvent was evaporated under reduced pressure, and the obtained residue was purified by silica gel column chromatography (hexane-ethyl acetate) to afford Compound 6 (554 mg, yield 95%).

[M+H]=502.00, measurement condition: C, retention time: 2.35 min

Step 6 Synthesis of Compound 7

Compound 6 (100 mg, 0.189 mmol) was dissolved in tetrahydrofuran (2 mL), and triethylamine (0.036 mL, 0.259 mmol) was added under ice cooling, and the mixture was stirred at room temperature for 1 hour. Insoluble matter in the reaction solution was removed by filtration, and an aqueous solution (0.3 mL) of sodium borohydride (11.3 mg, 0.299 mmol) was added dropwise thereto, and the mixture was stirred at room temperature for 18 hours. A saturated aqueous solution of ammonium chloride was added, and extraction was performed with ethyl acetate, and the organic layer was dried over anhydrous magnesium sulfate. The solvent was evaporated under reduced pressure, and the obtained residue was purified by silica gel column chromatography (hexane-ethyl acetate) to afford Compound 7 (15 mg, yield 15%).

1H-NMR (CDCl3) δ: 2.03-2.10 (m, 2H), 2.27-2.38 (m, 5H), 3.13 (t, J=7.0 Hz, 1H), 3.26 (d, J=17.4 Hz, 1H), 3.45 (d, J=17.4 Hz, 1H), 4.03 (t, J=6.0 Hz, 2H), 4.17 (d, J=7.0 Hz, 2H), 6.27 (s, 1H), 6.93 (d, J=8.7 Hz, 2H), 7.08 (d, J=8.0 Hz, 2H), 7.19 (d, J=8.0 Hz, 2H), 7.43 (d, J=8.7 Hz, 2H).

Step 7 Synthesis of Compound 8

Compound 7 (13.7 mg, 0.028 mmol), tert-butyl methylsulfonylcarbamate (18.12 mg, 0.093 mmol), and triphenylphosphine (24.33 mg, 0.093 mmol) were dissolved in tetrahydrofuran (0.5 mL), and a 1 mol/L toluene solution of diisopropyl azodicarboxylate (0.048 mL, 0.093 mmol) was added dropwise, and the mixture was stirred at room temperature for 6 hours. Water was added, extraction was performed with ethyl acetate, and the organic layer was dried over anhydrous magnesium sulfate. The solvent was evaporated under reduced pressure, and the obtained residue was purified by silica gel column chromatography (hexane-ethyl acetate), and the resulting mixture of Compound 8 and impurities was used directly in the next reaction.

[M+H]=665.25, measurement condition: C, retention time: 2.78 min

Step 8 Synthesis of Compound I-1

The mixture of Compound 8 and impurities was dissolved in dichloromethane (0.6 mL), and a 4 mol/L dioxane solution of hydrochloric acid (0.4 mL, 1.60 mmol) was added at room temperature, and the resultant was then stirred for 19 hours. The solvent was evaporated under reduced pressure, and the obtained residue was purified by silica gel column chromatography (hexane-ethyl acetate) to afford Compound I-1 (6.3 mg, yield 41%).

1H-NMR (CDCl3) δ: 2.02-2.10 (m, 2H), 2.25-2.39 (m, 5H), 2.71 (s, 3H), 3.28 (d, J=17.6 Hz, 1H), 3.47 (d, J=17.6 Hz, 1H), 3.83 (dd, J=13.6, 6.6 Hz, 1H), 3.91 (dd, J=13.6, 6.6 Hz, 1H), 4.03 (t, J=5.9 Hz, 2H), 5.46 (t, J=6.6 Hz, 1H), 6.58 (s, 1H), 6.94 (d, J=8.8 Hz, 2H), 7.07 (d, J=8.2 Hz, 2H), 7.23 (d, J=8.2 Hz, 2H), 7.43 (d, J=8.8 Hz, 2H).

Example 2 Synthesis of Compound I-4

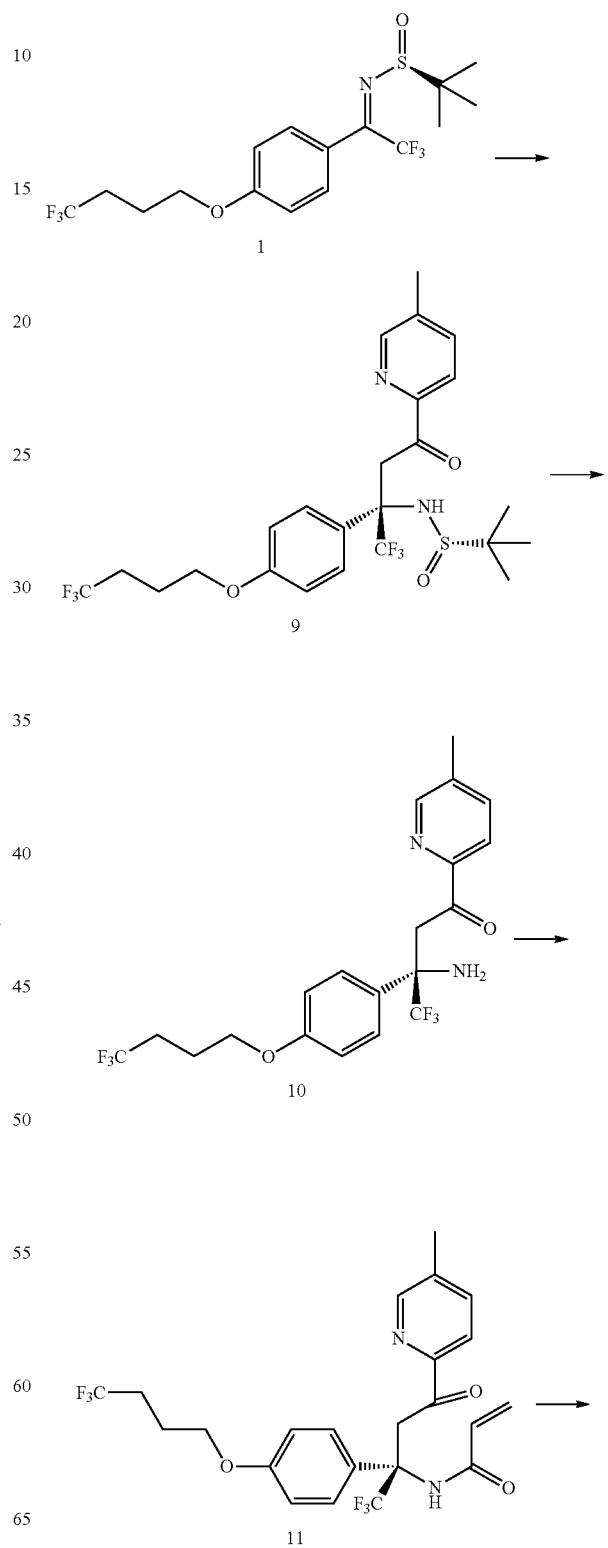

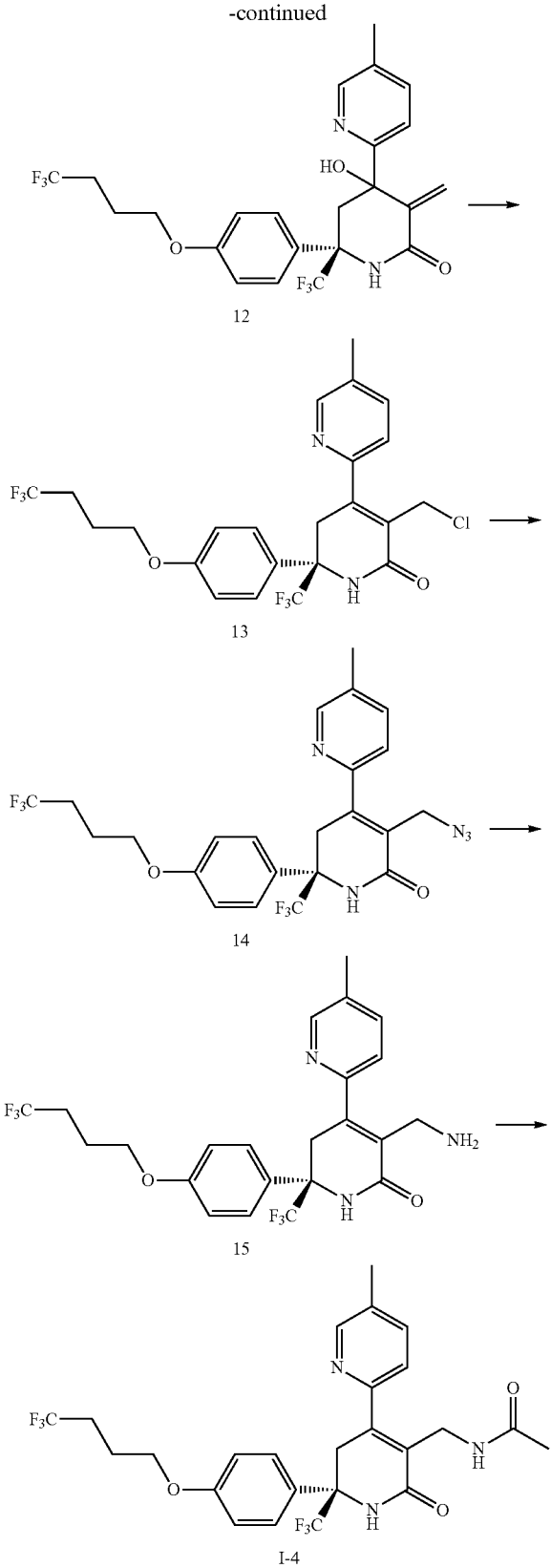

Step 1 Synthesis of Compound 9

Under nitrogen atmosphere, a solution of diisopropylamine (3.27 mL, 23.3 mmol) in tetrahydrofuran (40 mL) was cooled to −78° C. with dry ice-acetone. A 1.63 mol/L solution of n-butyllithium-hexane (15 mL, 23.3 mmol) was added dropwise thereto, and the mixture was warmed from −78° C. to −30° C. with stirring over 1 hour. A solution of 1-(5-methylpyridin-2-yl)ethanone (3.14 g, 23.3 mmol) in tetrahydrofuran (6 mL) was added dropwise at −78° C., and the mixture was then stirred for 30 minutes. A solution of Compound 1 (described in WO2014/193884) (4.69 g, 11.63 mmol) in tetrahydrofuran (40 mL) was added, and the mixture was stirred at −78° C. for 1 hour 15 minutes. An aqueous solution of ammonium chloride was added, and the mixture was warmed to room temperature. Water was added, extraction was performed with ethyl acetate, and the organic layer was dried over anhydrous magnesium sulfate. The solvent was evaporated under reduced pressure, and the obtained residue was purified by silica gel column chromatography (hexane-ethyl acetate) to afford Compound 9 (3.08 g, yield 49%).

1H-NMR (CDCl3) δ: 1.30 (s, 9H), 2.01-2.09 (m, 2H), 2.25-2.38 (m, 2H), 2.43 (s, 3H), 3.98-4.05 (m, 3H), 4.49 (d, J=17.3 Hz, 1H), 6.61 (s, 1H), 6.90 (d, J=8.3 Hz, 2H), 7.59-7.66 (m, 3H), 7.96 (d, J=8.0 Hz, 1H), 8.50 (s, 1H).

Step 2 Synthesis of Compound 10

Compound 9 (2.04 g, 3.79 mmol) was dissolved in dioxane (15 mL), and a 4 mol/L solution of hydrochloric acid-dioxane (19.0 mL, 76.0 mmol) was added thereto, and the mixture was stirred at room temperature for 24 hours. The solvent was evaporated under reduced pressure, and the obtained residue was added to a saturated aqueous solution of sodium bicarbonate, and extracted with ethyl acetate, and the organic layer was dried over anhydrous magnesium sulfate. The solvent was evaporated under reduced pressure, and the resultant was then used directly in the next reaction.

Step 3 Synthesis of Compound 11

Compound 10 (1.60 g, 3.68 mmol) was dissolved in dichloromethane (32 mL), pyridine (2.98 mL, 36.8 mmol) was added, subsequently acryloyl chloride (2.091 mL, 25.8 mmol) was added dropwise, and the mixture was stirred at room temperature for 18 hours. Water and a 1 mol/L aqueous solution of hydrochloric acid were added, extraction was performed with dichloromethane, and the organic layer was dried over anhydrous magnesium sulfate. The solvent was evaporated under reduced pressure, and the obtained residue was purified by silica gel column chromatography (hexane-ethyl acetate) to afford Compound 11 (1.21 g, yield 67%).

1H-NMR (CDCl3) δ: 1.99-2.08 (m, 2H), 2.23-2.37 (m, 2H), 2.44 (s, 3H), 3.91 (d, J=16.1 Hz, 1H), 4.00 (t, J=5.8 Hz, 2H), 4.72 (d, J=16.1 Hz, 1H), 5.71 (d, J=9.0 Hz, 1H), 6.21-6.34 (m, 2H), 6.87 (d, J=8.4 Hz, 2H), 7.35 (s, 1H), 7.43 (d, J=8.4 Hz, 2H), 7.64 (d, J=7.9 Hz, 1H), 7.91 (d, J=7.9 Hz, 1H), 8.52 (s, 1H).

Step 4 Synthesis of Compound 12

Compound 11 (1.21 g, 2.477 mmol) was dissolved in dioxane (10 mL), 1,4-diazabicyclo[2,2,2]octane (2.78 g, 24.77 mmol) was added, and the mixture was stirred at 85° C. for 43 hours. The temperature was lowered to room temperature, the solvent was evaporated under reduced pressure, and the obtained residue was purified by silica gel column chromatography (hexane-ethyl acetate) to afford Compound 12 (1.06 g, yield 88%) as a diastereomer mixture.

1H-NMR (CDCl3) δ: 2.01-2.10 (m, 2H), 2.26-2.39 (m, 5H), 2.75 (d, J=13.9 Hz, 1H), 2.99 (d, J=13.9 Hz, 1H), 4.03 (t, J=5.6 Hz, 2H), 5.00 (s, 1H), 6.44 (s, 1H), 6.56 (brs, 1H), 6.92 (d, J=8.3 Hz, 2H), 7.31 (d, J=8.1 Hz, 1H), 7.47 (d, J=8.3 Hz, 2H), 7.59 (d, J=8.1 Hz, 1H), 8.36 (s, 1H).

1H-NMR (CDCl3) δ: 1.97-2.06 (m, 2H), 2.11 (s, 3H), 2.22-2.34 (m, 2H), 2.80 (d, J=13.3 Hz, 1H), 3.20 (d, J=13.3 Hz, 1H), 3.89 (t, J=5.9 Hz, 2H), 6.14 (s, 1H), 6.49-6.55 (m, 3H), 6.76 (s, 1H), 6.86 (s, 1H), 6.91-6.97 (m, 3H), 8.05 (s, 1H).

Step 5 Synthesis of Compound 13

Compound 12 (200 mg, 0.409 mmol) was dissolved in dichloromethane (4 mL), thionyl chloride (0.149 mL, 2.047 mmol) and a drop of dimethylformamide were added dropwise under ice cooling, and the resultant was then stirred for 6.5 hours. Water was added, extraction was performed with dichloromethane, and the organic layer was dried over anhydrous magnesium sulfate. The solvent was evaporated under reduced pressure, and the obtained residue was used in the next reaction without being purified.

Step 6 Synthesis of Compound 14

Compound 13 was dissolved in dimethylsulfoxide (4 mL), sodium azide (106 mg, 1.634 mmol) was added under ice cooling, and the mixture was stirred at room temperature for 2 hours. Water was added, extraction was performed with ethyl acetate, and the organic layer was dried over anhydrous magnesium sulfate. The solvent was evaporated under reduced pressure, and the obtained residue was purified by silica gel column chromatography (hexane-ethyl acetate) to afford Compound 14 (122 mg, yield in two steps 58%).

[M+H]=514.05, measurement condition: C, retention time: 2.53 min

Step 7 Synthesis of Compound 15

Compound 14 (122 mg, 0.238 mmol) was dissolved in tetrahydrofuran (3 mL) and water (1 mL), triphenylphosphine (68.6 mg, 0.261 mmol) was added, and the mixture was stirred at room temperature for 17.5 hours. The solvent was evaporated under reduced pressure, and the obtained residue was purified by silica gel column chromatography (hexane-ethyl acetate) to afford Compound 15 (59.5 mg, yield 51%).

[M+H]=488.10, measurement condition: C, retention time: 1.70 min

Step 8 Synthesis of Compound I-4

Compound 15 (9.0 mg, 0.018 mmol) was dissolved in methanol (0.5 mL), acetic anhydride (0.010 mL, 0.106 mmol) was added, and the mixture was stirred at room temperature for 3.5 hours. The solvent was evaporated under reduced pressure, and the obtained residue was purified by silica gel column chromatography (chloroform-methanol) to afford Compound I-4 (6.5 mg, yield 66.5%).

1H-NMR (CDCl3) δ: 1.90 (s, 3H), 2.01-2.09 (m, 2H), 2.26-2.38 (m, 5H), 3.48 (d, J=17.6 Hz, 1H), 3.67 (d, J=17.6 Hz, 1H), 3.93-4.04 (m, 3H), 4.23 (dd, J=14.3, 7.0 Hz, 1H), 6.35 (s, 1H), 6.43 (brs, 1H), 6.90 (d, J=8.4 Hz, 2H), 7.39 (d, J=8.0 Hz, 1H), 7.47 (d, J=8.4 Hz, 2H), 7.56 (d, J=8.0 Hz, 1H), 8.49 (s, 1H).

Example 3 Synthesis of Compound I-75

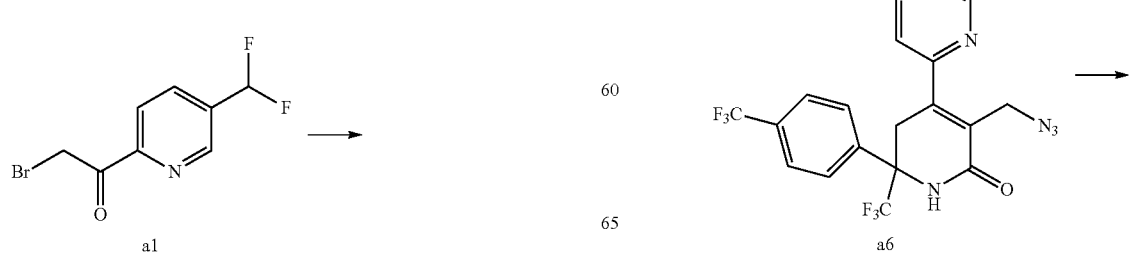

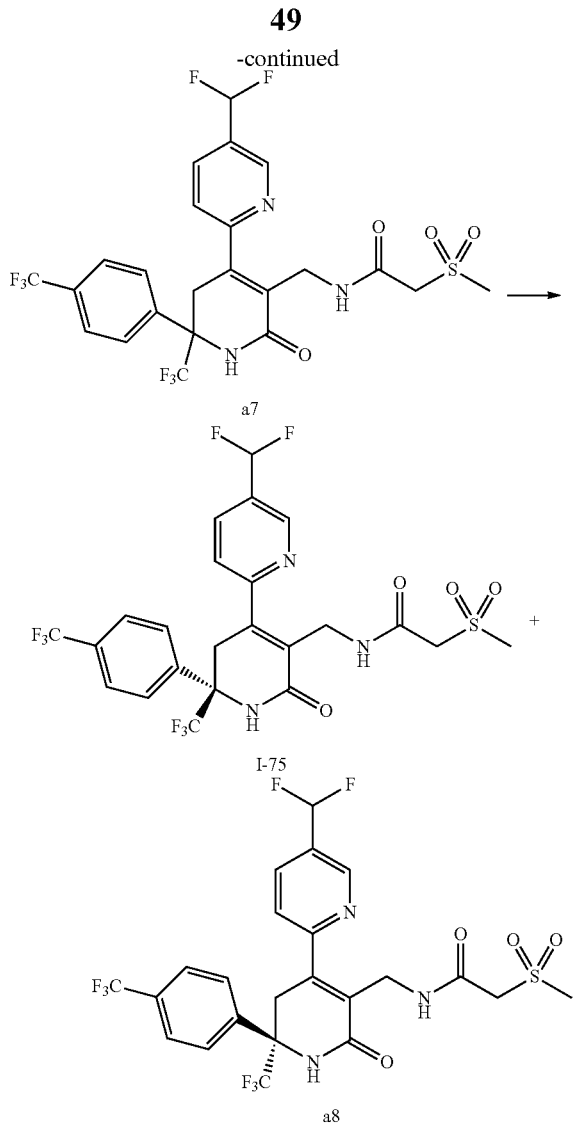

Step 1 Synthesis of Compound a2

Triphenylphosphine (15.8 g, 60.2 mmol) was dissolved in tetrahydrofuran (150 mL), a solution of Compound a1 (15.6 g, 60.2 mmol; WO2016/106331) in tetrahydrofuran (50 mL) was added dropwise under warming to 75° C., and the mixture was further stirred for 2 hours. The temperature of the reaction solution was returned to room temperature, and the precipitated crystals were collected by filtration. The obtained crystals were dissolved in methanol (100 mL) and water (50 mL), a 2 mol/L solution of sodium hydroxide (150 mL) was added, and the mixture was stirred at room temperature for 30 minutes. Water was added to the reaction solution, and extraction was performed with chloroform. The organic layer was washed by brine, and dried over anhydrous sodium sulfate. The solvent was evaporated under reduced pressure to afford Compound a2 (22.8 g, yield 88%). 1H-NMR (CDCl3) δ: 5.31 (d, JH-P=25.6 Hz, 1H), 6.74 (t, JH-F=56.0 Hz, 1H), 7.46-7.51 (m, 6H), 7.56-7.60 (m, 3H), 7.71-7.76 (m, 6H), 7.88 (d, J=8.0 Hz, 1H), 8.23 (d, J=8.0 Hz, 1H), 8.70 (s, 1H).

Step 2 Synthesis of Compound a3

Compound a2 (1.8 g, 4.17 mmol) was dissolved in dimethylsulfoxide (9 mL), 4-(trifluoromethyl)trifluoroacetophenone (1.01 g, 4.17 mmol) was added, and the mixture was then stirred under microwave irradiation at 150° C. for 30 minutes. Aqueous ammonia (7.13 mL) was added to the reaction solution, and the reaction solution was stirred at room temperature for 5 hours. Water was added to the reaction solution, and extraction was performed with ethyl acetate. The organic layer was washed by brine, and dried over anhydrous sodium sulfate. The solvent was evaporated under reduced pressure, and the obtained residue was purified by silica gel column chromatography (hexane-ethyl acetate) to afford Compound a3 (1.62 g, yield 94%).

1H-NMR (CDCl3) δ: 2.45 (br.s, 2H), 3.84 (d, J=17.2 Hz, 1H), 4.48 (d, J=17.2 Hz, 1H), 6.78 (t, JH-F=55.2 Hz, 1H), 7.60 (d, J=8.4 Hz, 2H), 7.76 (d, J=8.4 Hz, 2H), 7.97 (s, 2H), 8.83 (s, 1H).

Step 3 Synthesis of Compound a4

Compound a3 (1.61 g, 3.91 mmol) was dissolved in dimethylacetamide (16 mL), acryloyl chloride (530 mg, 5.86 mmol) was added under ice cooling, and the mixture was then stirred at room temperature for 2 hours. A saturated aqueous solution of sodium bicarbonate was added to the reaction solution, and extraction was performed with methylene chloride. The organic layer was washed by water and brine, and dried over anhydrous sodium sulfate. The solvent was evaporated under reduced pressure to afford Compound a4 (1.74 g).

1H-NMR (CDCl3) δ: 4.00 (d, J=16.8 Hz, 1H), 4.92 (d, J=16.8 Hz, 1H), 5.75 (dd, J=2.8, 8.4 Hz, 1H), 6.22-6.33 (m, 2H), 6.79 (t, JH-F=55.2 Hz, 1H), 6.81 (br.s, 1H), 7.43 (d, J=8.4 Hz, 2H), 7.52 (d, J=8.4 Hz, 2H), 7.99 (d, J=8.0 Hz, 1H), 8.08 (d, J=8.0 Hz, 1H), 8.83 (s, 1H).

Step 4 Synthesis of Compound a5

Compound a4 (1.74 g, 3.91 mmol) was dissolved in dioxane (8 mL), 1,4-diazabicyclo[2,2,2]octane (2.19 g, 19.5 mmol) was added, and the mixture was then stirred at 90° C. for 8 hours. Water was added to the reaction solution, and extraction was performed with ethyl acetate. The organic layer was washed by brine, and dried over anhydrous sodium sulfate. The solvent was evaporated under reduced pressure, and the obtained residue was purified by silica gel column chromatography (hexane-ethyl acetate) to afford Compound a5 (1.52 g, yield 84%).

1H-NMR (CDCl3) δ: 2.82 (d, J=14.4 Hz, 1H), 3.08 (d, J=14.4 Hz, 1H), 4.65 (s, 1H), 4.99 (s, 1H), 6.52 (s, 1H), 6.47 (br.s, 1H), 6.77 (t, JH-F=55.6 Hz, 1H), 7.57 (d, J=8.4 Hz, 1H), 7.64-7.77 (m, 4H), 7.97 (d, J=8.4 Hz, 2H), 8.71 (s, 1H).

Step 5 Synthesis of Compound a6

Compound a5 (1.52 g, 3.26 mmol) was dissolved in methylene chloride (23 mL), thionyl chloride (1.94 g, 16.3 mmol) and several drops of dimethylformamide were added under ice cooling, and the mixture was then stirred at room temperature for 3 hours. The reaction solution was subjected to evaporation under reduced pressure, dimethylsulfoxide (16 mL) was added to the obtained residue, sodium azide (636 mg, 9.78 mmol) was added, and the mixture was stirred at room temperature for 2 hours. Water was added to the reaction solution, and extraction was performed with ethyl acetate. The organic layer was washed by brine, and dried over anhydrous sodium sulfate. The solvent was evaporated under reduced pressure, and the obtained residue was purified by silica gel column chromatography (hexane-ethyl acetate) to afford Compound a6 (964 mg, yield 60%).

1H-NMR (CDCl3) δ:3.61 (d, J=17.2 Hz, 1H), 3.86 (d, J=17.2 Hz, 1H), 3.89 (d, J=12.8 Hz, 1H), 4.02 (d, J=12.8 Hz, 1H), 6.76 (d, JH-F=55.6 Hz, 1H), 7.08 (s, 1H), 7.61 (d, J=8.0 Hz, 1H), 7.70 (d, J=8.4 Hz, 2H), 7.78 (d, J=8.4 Hz, 2H), 7.92 (d, J=8.0 Hz, 1H), 8.85 (s, 1H).

Step 6 Synthesis of Compound I-75

Compound a6 (148 mg, 0.301 mmol) was dissolved in tetrahydrofuran (6 mL) and water (1.5 mL), triphenylphosphine (95 mg, 0.361 mmol) was added at room temperature, and the mixture was then stirred at 40° C. for 2 hours. Water was added to the reaction solution, and extraction was performed with ethyl acetate. The organic layer was washed by brine, and dried over anhydrous sodium sulfate. The solvent was evaporated under reduced pressure to afford a crude product. The obtained crude product was dissolved in methylene chloride (3 mL), 2-methylsulfonylacetic acid (62 mg, 0.452 mmol) and N,N'-dicyclohexylcarbodiimide (93.5 mg, 0.452 mmol) were added, and the mixture was then stirred at room temperature for 1 hour. The precipitated crystals were removed by filtration, the solvent was evaporated under reduced pressure, and the obtained residue was purified by silica gel column chromatography (chloroform-methanol) to afford Compound a7 (104 mg, yield 59%) as a racemic mixture. Compound a7 was purified by supercritical chromatography (ethanol) to afford Compound I-75 (30 mg, yield 17%) and Compound a8 (29 mg, yield 17%).

1H-NMR (CDCl3) δ: 3.19 (s, 3H), 3.36 (d, J=17.6 Hz, 1H), 3.89 (d, J=13.6 Hz, 1H), 3.95 (d, J=13.6 Hz, 1H), 3.97 (d, J=17.6 Hz, 1H), 4.27 (d, J=13.6 Hz, 1H), 4.33 (dd, J=8.0, 13.6 Hz, 1H), 6.76 (d, JH-F=55.6 Hz, 1H), 6.90 (d, J=8.0 Hz, 1H), 7.00 (d, J=8.0 Hz, 2H), 7.77 (s, 1H), 7.83 (d, J=8.0 Hz, 2H), 7.89 (d, J=8.0 Hz, 1H), 8.00 (br.d, J=6.0 Hz, 1H), 8.85 (s, 1H).

TABLE 1

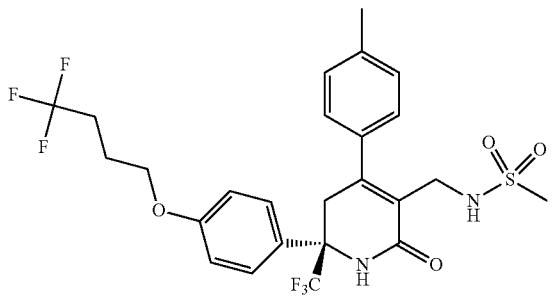 [SMILES: Cc1ccc(C2=C(CNS(C)(=O)=O)C(=O)N[C@@](c3ccc(OCCCC(F)(F)F)cc3)(C(F)(F)F)C2)cc1]

I-1

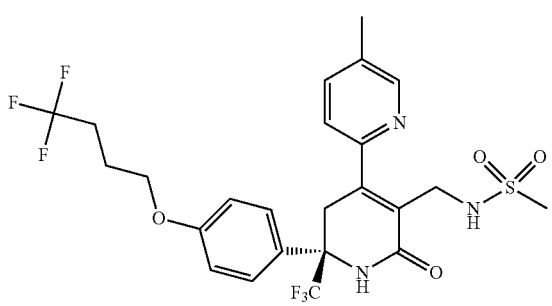 [SMILES: Cc1ccc(C2=C(CNS(C)(=O)=O)C(=O)N[C@@](c3ccc(OCCCC(F)(F)F)cc3)(C(F)(F)F)C2)nc1]

I-3

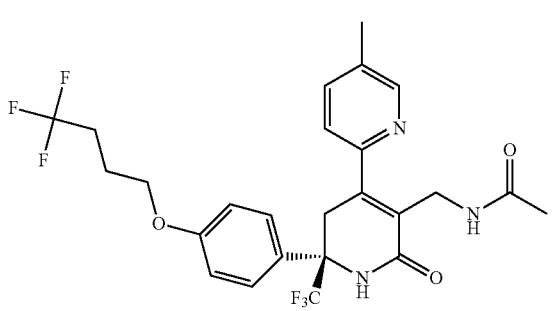 [SMILES: CC(=O)NCC1=C(c2ccc(C)cn2)C[C@](c2ccc(OCCCC(F)(F)F)cc2)(C(F)(F)F)NC1=O]

I-4

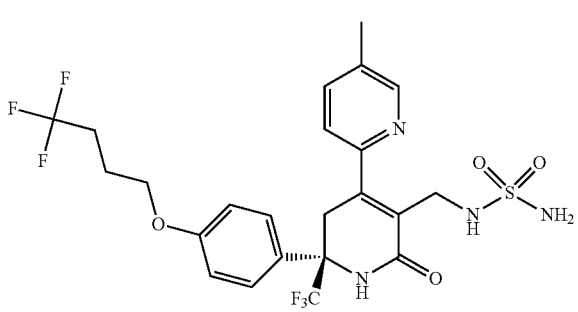 [SMILES: Cc1ccc(C2=C(CNS(N)(=O)=O)C(=O)N[C@@](c3ccc(OCCCC(F)(F)F)cc3)(C(F)(F)F)C2)nc1]

I-5

TABLE 1-continued
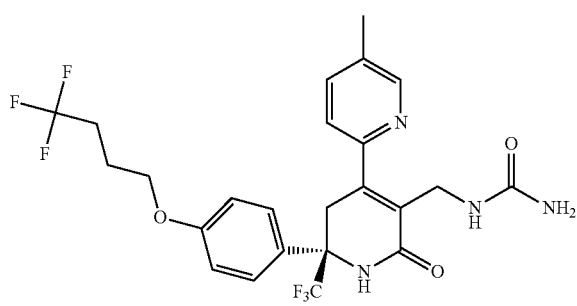 [SMILES: Cc1ccc(C2=C(CNC(N)=O)C(=O)N[C@@](c3ccc(OCCCC(F)(F)F)cc3)(C(F)(F)F)C2)nc1]
I-6
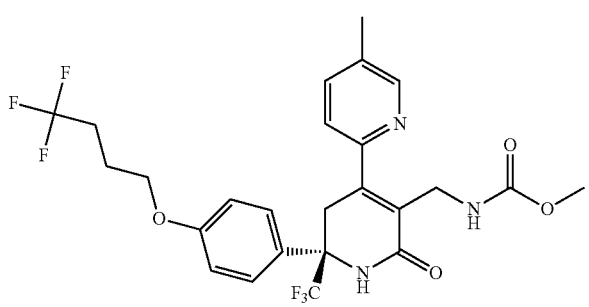 [SMILES: COC(=O)NCC1=C(c2ccc(C)cn2)C[C@](c2ccc(OCCCC(F)(F)F)cc2)(C(F)(F)F)NC1=O]
I-7
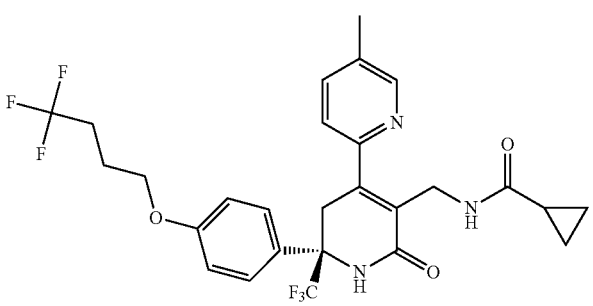 [SMILES: Cc1ccc(C2=C(CNC(=O)C3CC3)C(=O)N[C@@](c3ccc(OCCCC(F)(F)F)cc3)(C(F)(F)F)C2)nc1]
I-8
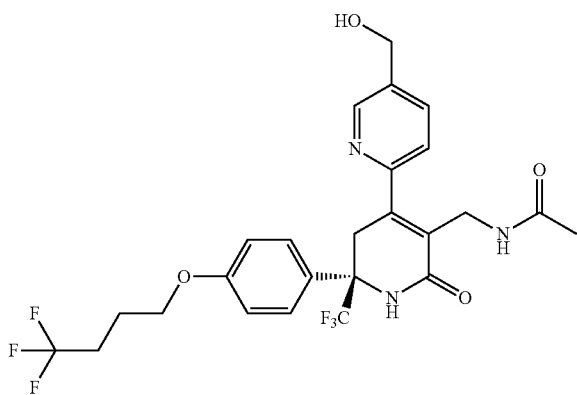 [SMILES: CC(=O)NCC1=C(c2ccc(CO)cn2)C[C@](c2ccc(OCCCC(F)(F)F)cc2)(C(F)(F)F)NC1=O]
I-9

TABLE 1-continued
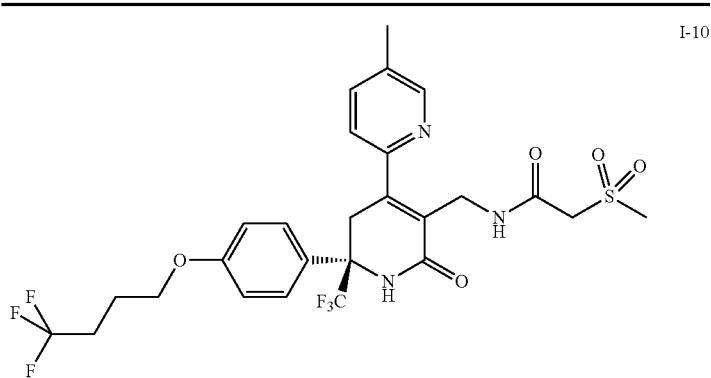
I-10
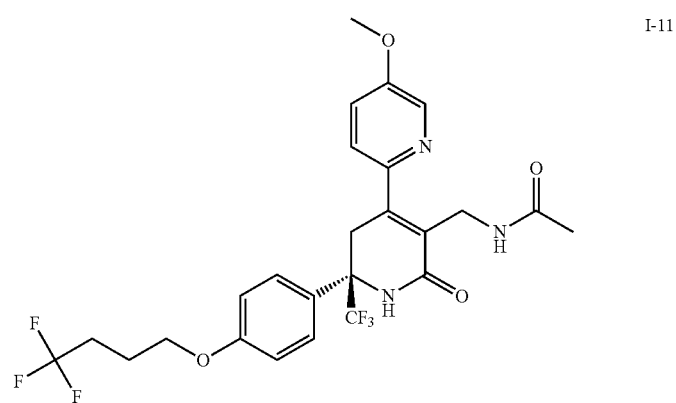
I-11
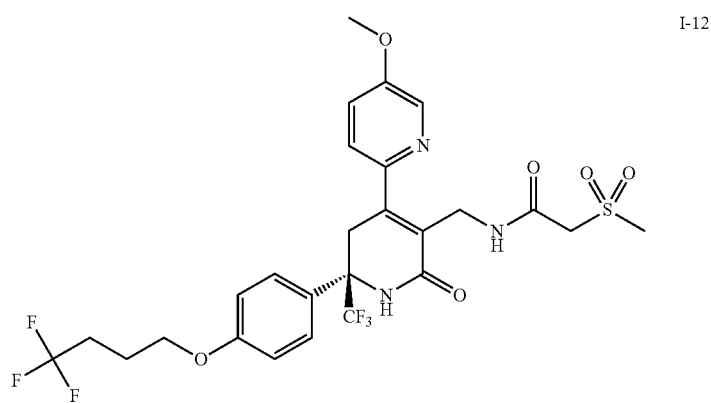
I-12
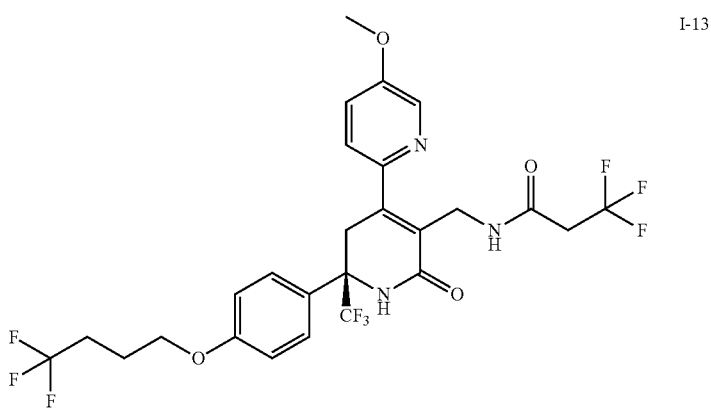
I-13

TABLE 2
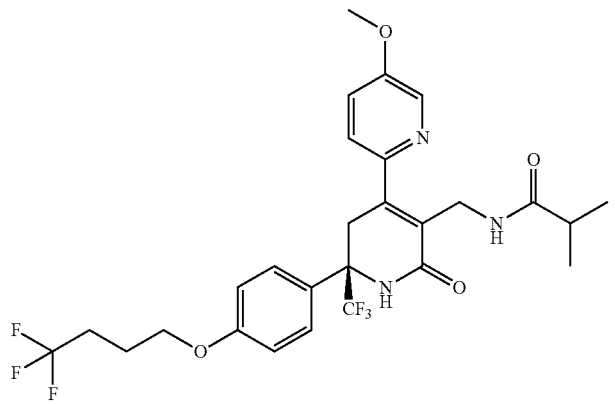 [SMILES: COc1ccc(C2=C(CNC(=O)C(C)C)C(=O)N[C@@](c3ccc(OCCCC(F)(F)F)cc3)(C(F)(F)F)C2)nc1]
I-14
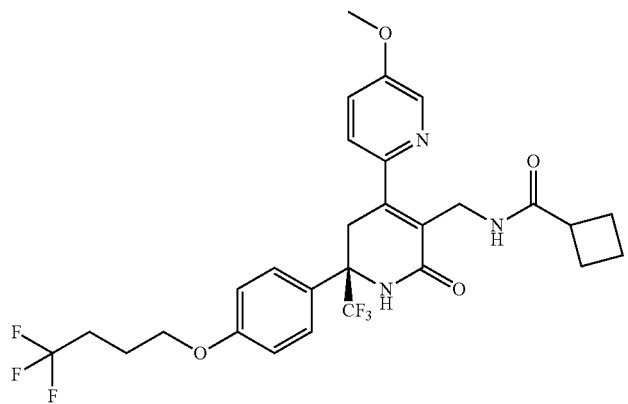 [SMILES: COc1ccc(C2=C(CNC(=O)C3CCC3)C(=O)N[C@@](c3ccc(OCCCC(F)(F)F)cc3)(C(F)(F)F)C2)nc1]
I-15
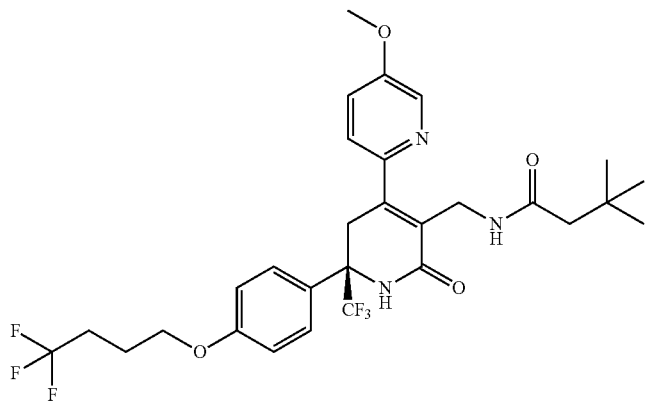 [SMILES: COc1ccc(C2=C(CNC(=O)CC(C)(C)C)C(=O)N[C@@](c3ccc(OCCCC(F)(F)F)cc3)(C(F)(F)F)C2)nc1]
I-16
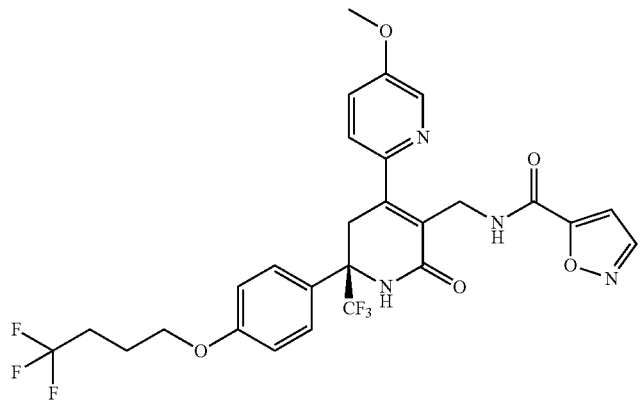 [SMILES: COc1ccc(C2=C(CNC(=O)c3ccno3)C(=O)N[C@@](c3ccc(OCCCC(F)(F)F)cc3)(C(F)(F)F)C2)nc1]
I-17

TABLE 2-continued
I-18
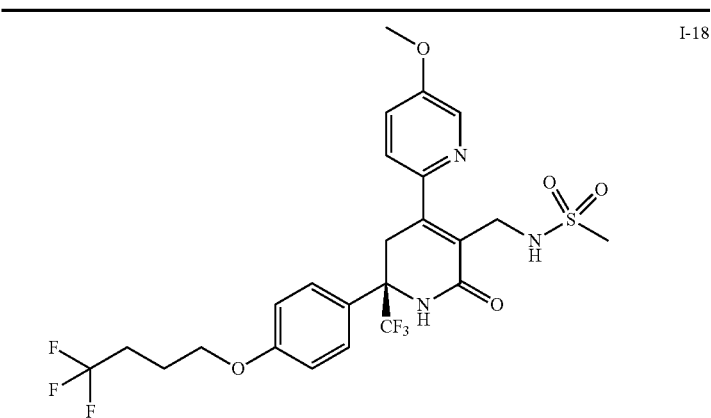
I-19
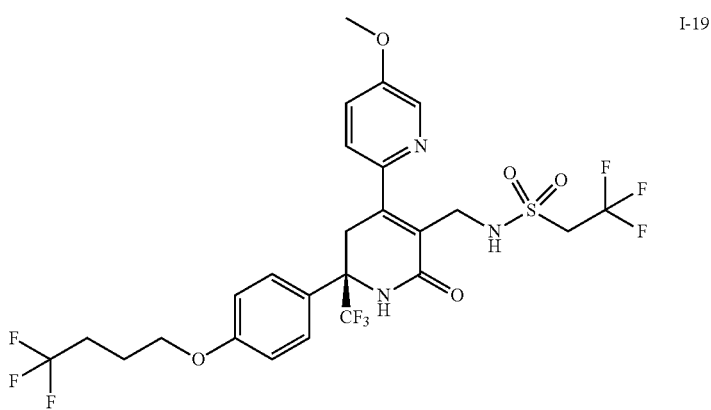
I-20
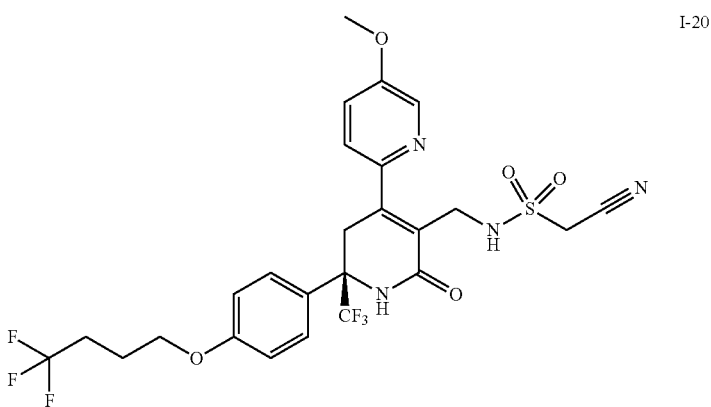
I-21
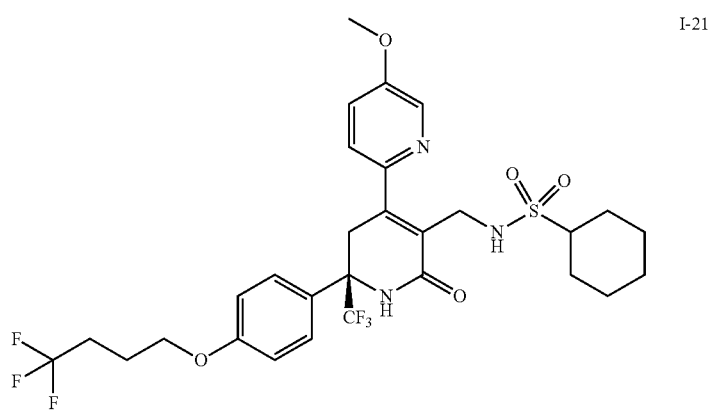

TABLE 2-continued
I-22
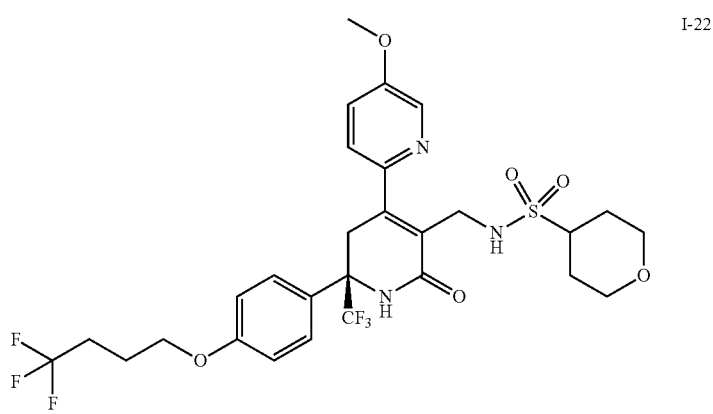
I-23
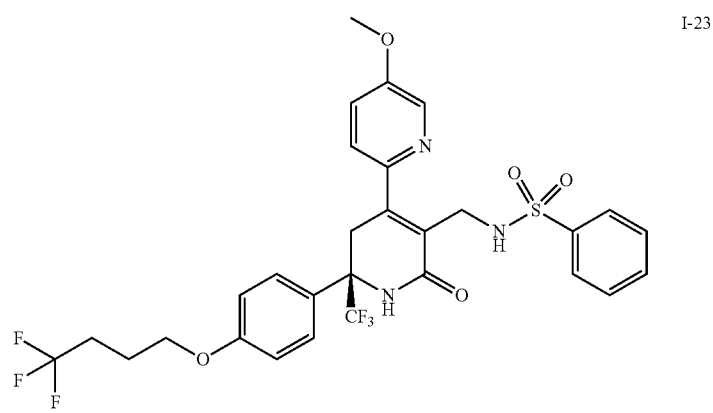
I-24
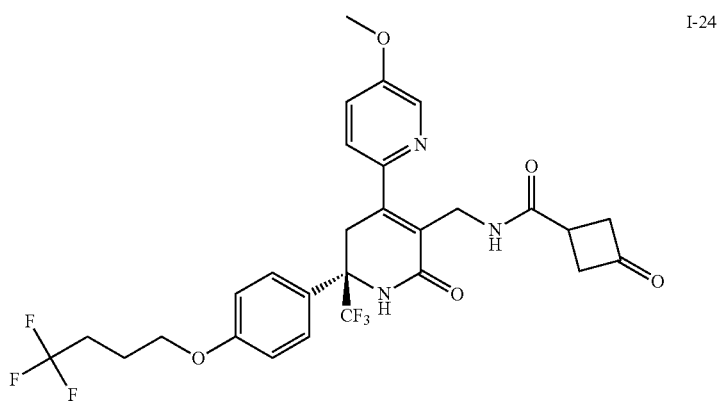
I-25
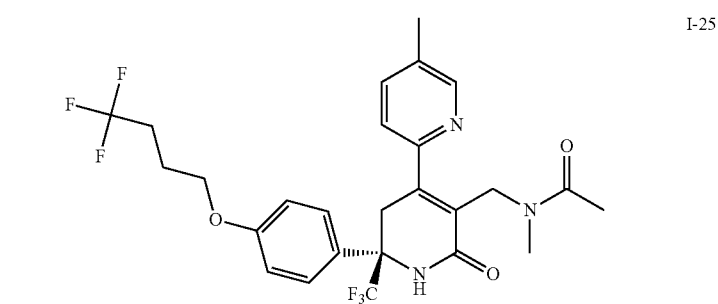

TABLE 3
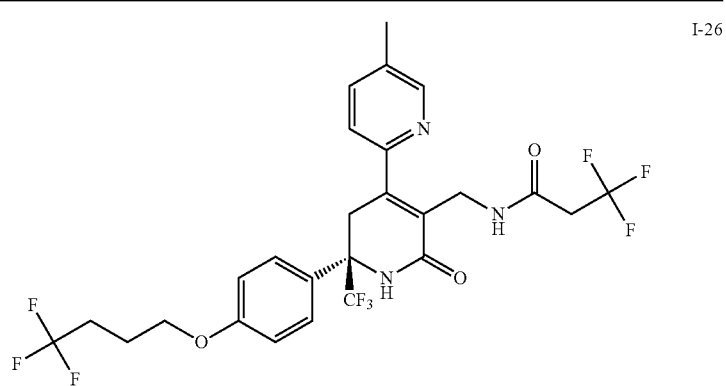
I-26
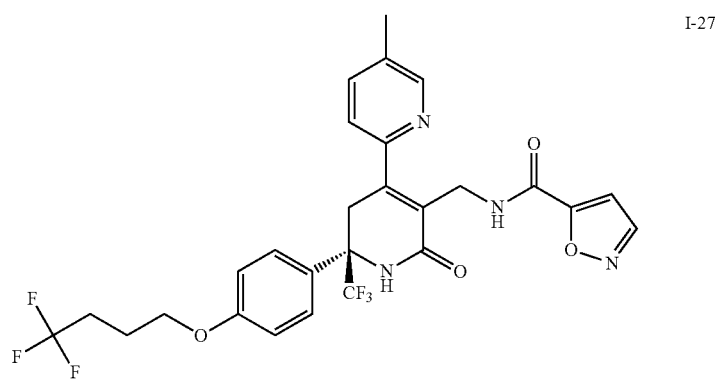
I-27
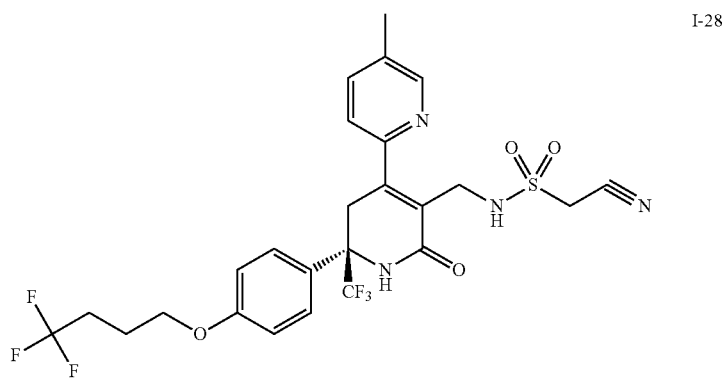
I-28
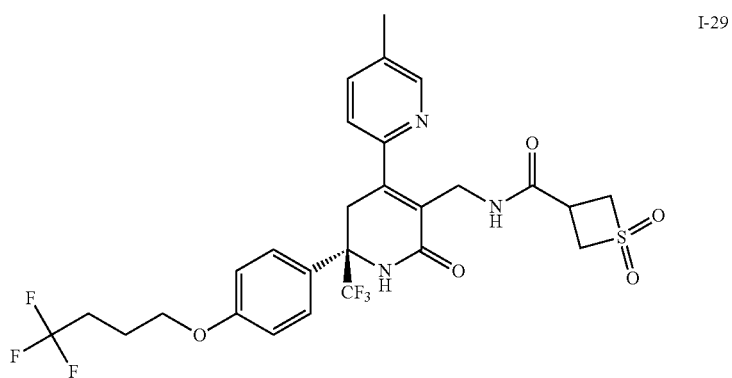
I-29

TABLE 3-continued
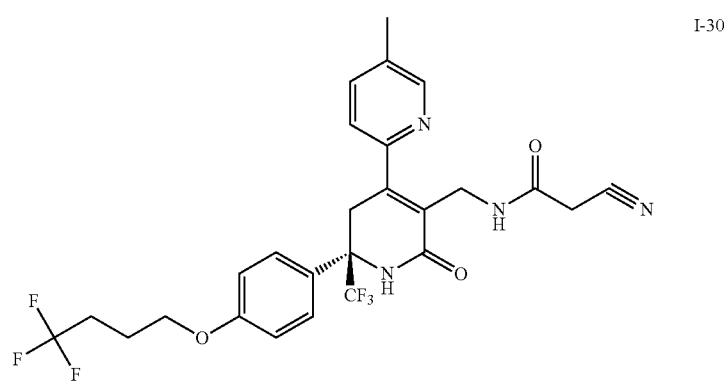
I-30
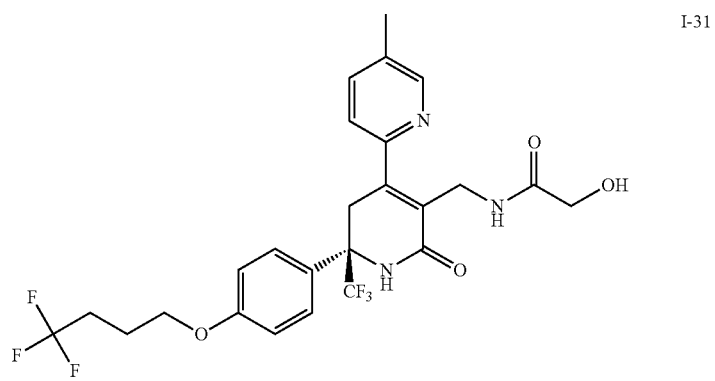
I-31
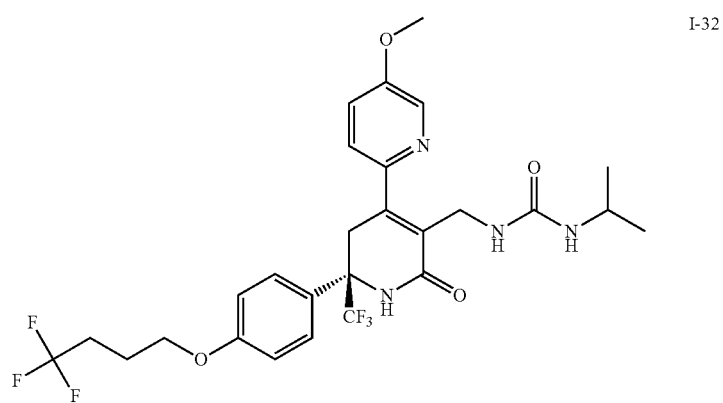
I-32
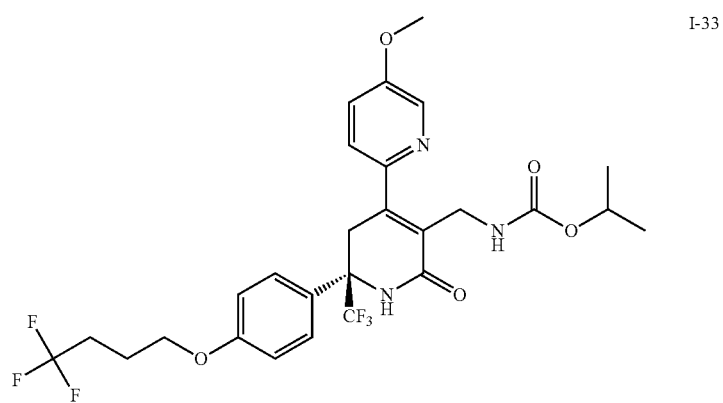
I-33

TABLE 3-continued
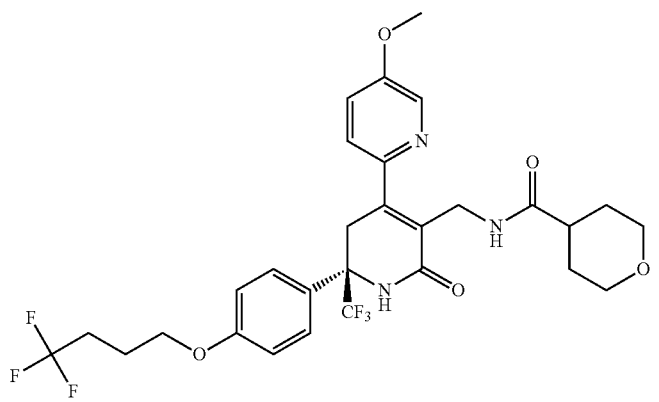 [SMILES: COc1ccc(C2=C(CNC(=O)C3CCOCC3)C(=O)N[C@@](c3ccc(OCCCC(F)(F)F)cc3)(C(F)(F)F)C2)nc1]
I-34
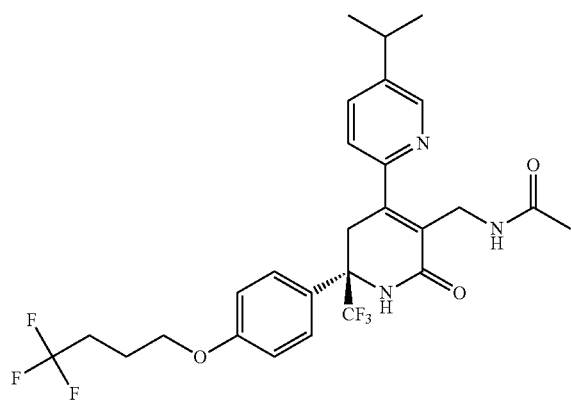 [SMILES: CC(=O)NCC1=C(c2ccc(C(C)C)cn2)C[C@](c2ccc(OCCCC(F)(F)F)cc2)(C(F)(F)F)NC1=O]
I-35
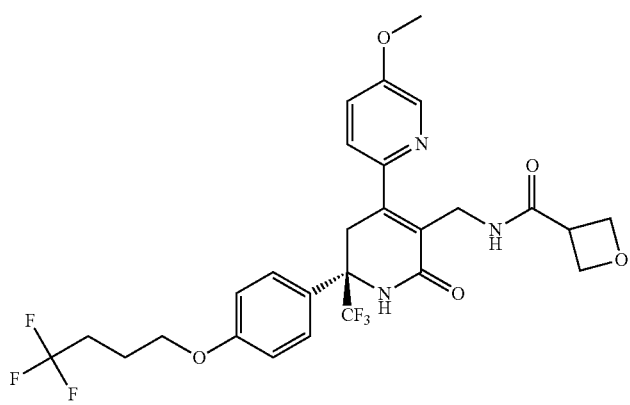 [SMILES: COc1ccc(C2=C(CNC(=O)C3COC3)C(=O)N[C@@](c3ccc(OCCCC(F)(F)F)cc3)(C(F)(F)F)C2)nc1]
I-36
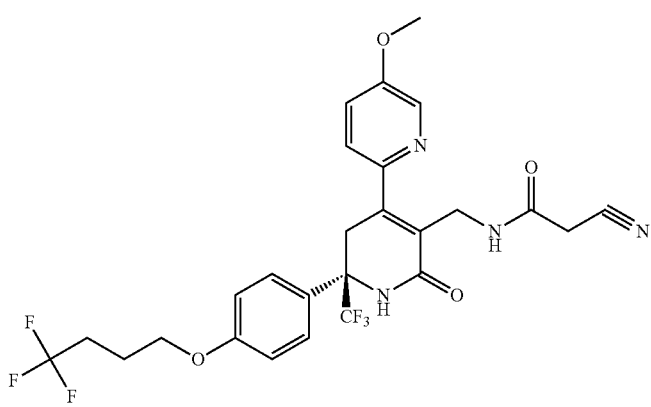 [SMILES: COc1ccc(C2=C(CNC(=O)CC#N)C(=O)N[C@@](c3ccc(OCCCC(F)(F)F)cc3)(C(F)(F)F)C2)nc1]
I-37

TABLE 4
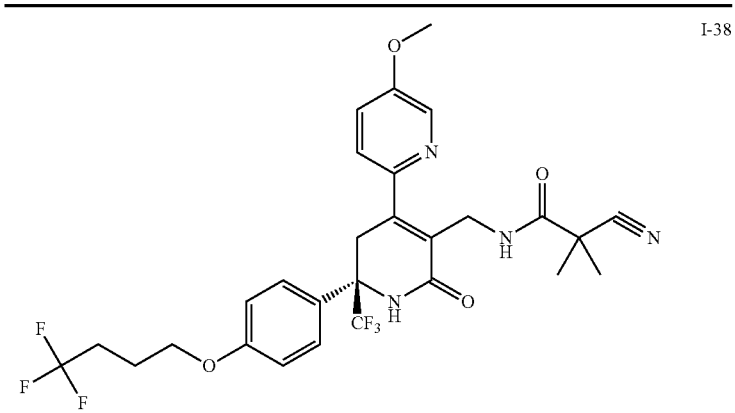
I-38
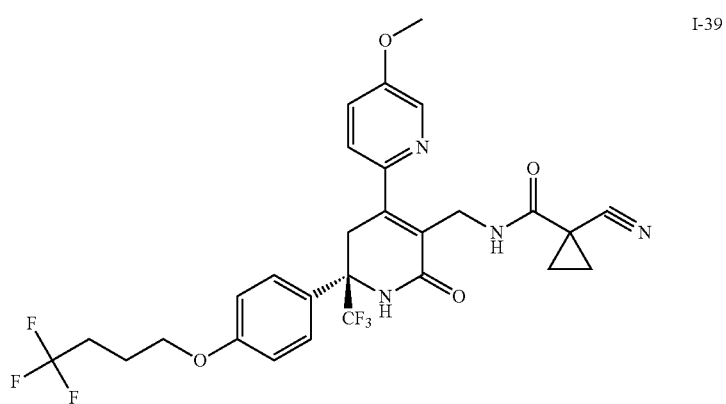
I-39
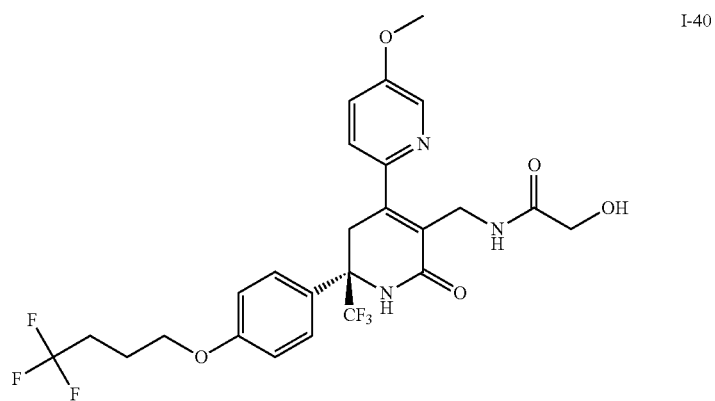
I-40
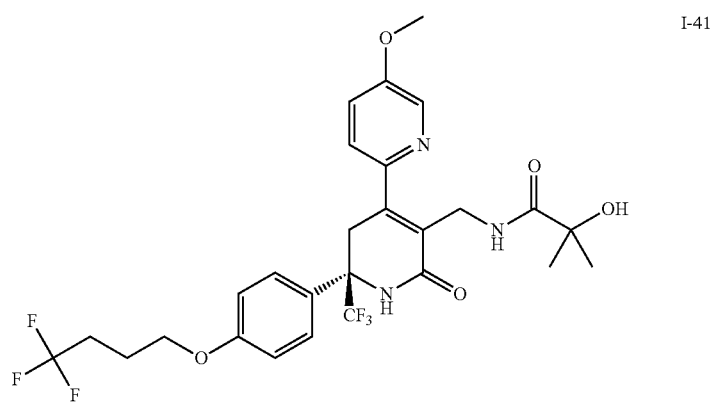
I-41

TABLE 4-continued
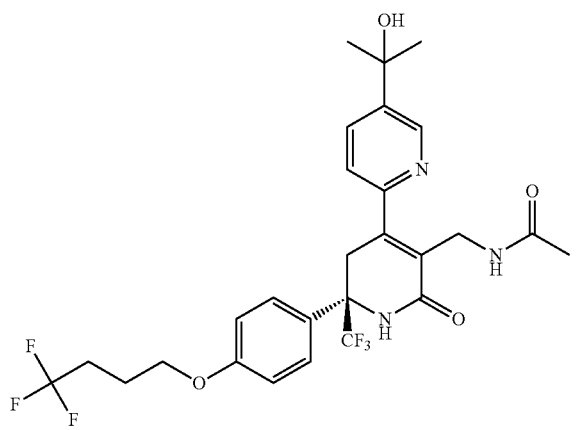 [SMILES: CC(=O)NCC1=C(c2ccc(C(C)(C)O)cn2)C[C@](c2ccc(OCCCC(F)(F)F)cc2)(C(F)(F)F)NC1=O] I-42
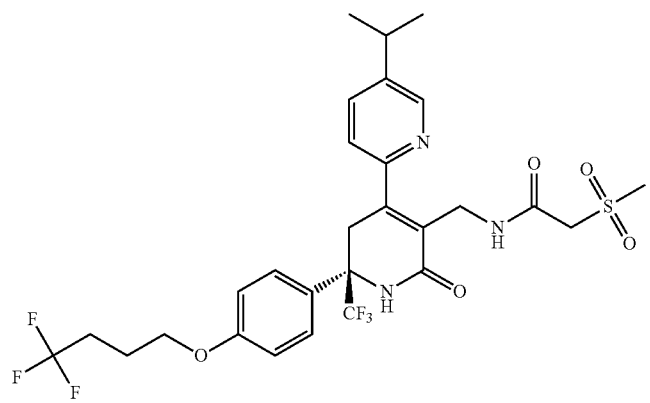 [SMILES: CC(C)c1ccc(C2=C(CNC(=O)CS(C)(=O)=O)C(=O)N[C@@](c3ccc(OCCCC(F)(F)F)cc3)(C(F)(F)F)C2)nc1] I-43
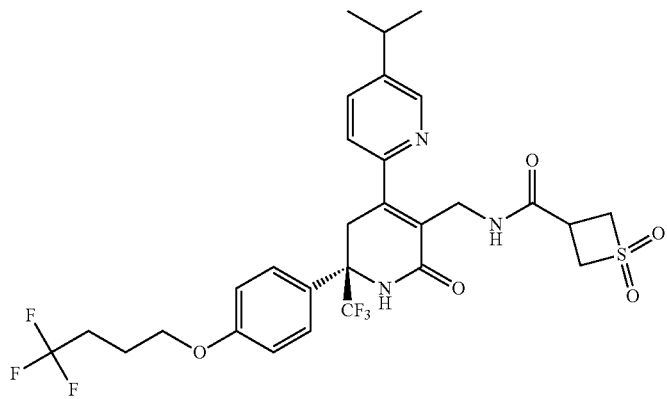 [SMILES: CC(C)c1ccc(C2=C(CNC(=O)C3CS(=O)(=O)C3)C(=O)N[C@@](c3ccc(OCCCC(F)(F)F)cc3)(C(F)(F)F)C2)nc1] I-44
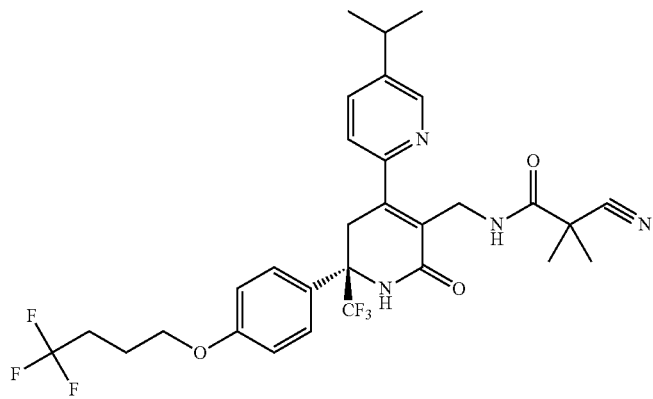 [SMILES: CC(C)c1ccc(C2=C(CNC(=O)C(C)(C)C#N)C(=O)N[C@@](c3ccc(OCCCC(F)(F)F)cc3)(C(F)(F)F)C2)nc1] I-45

TABLE 4-continued
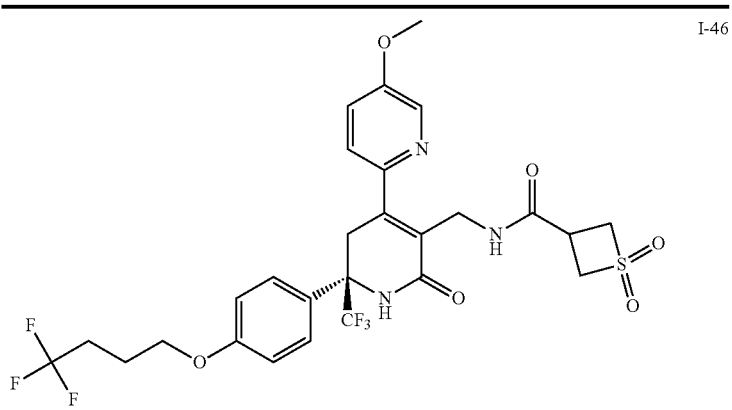
I-46
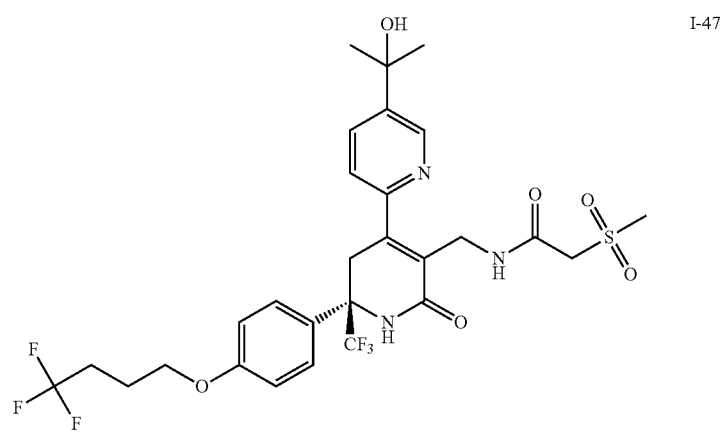
I-47
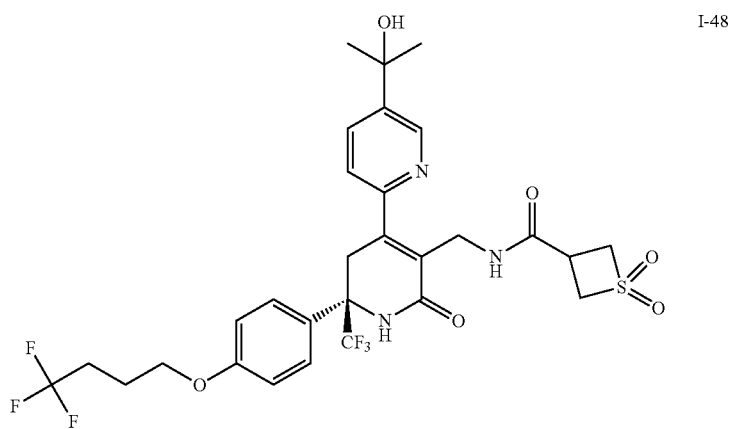
I-48
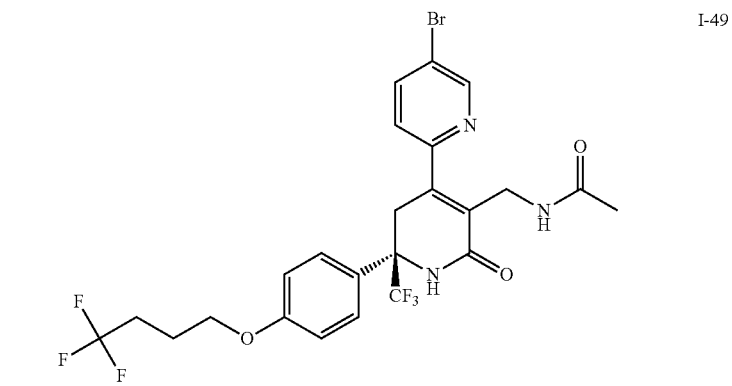
I-49

TABLE 5
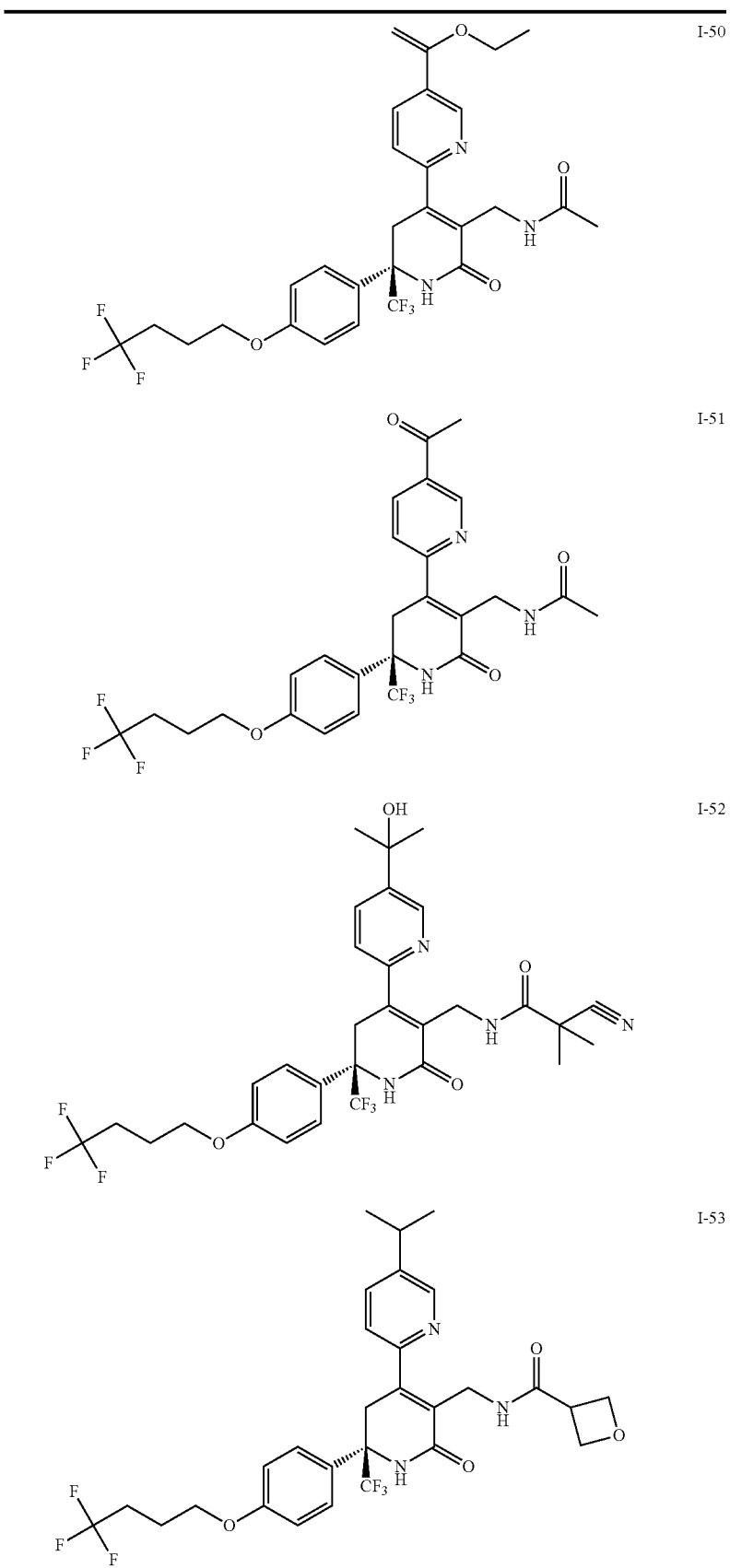

TABLE 5-continued
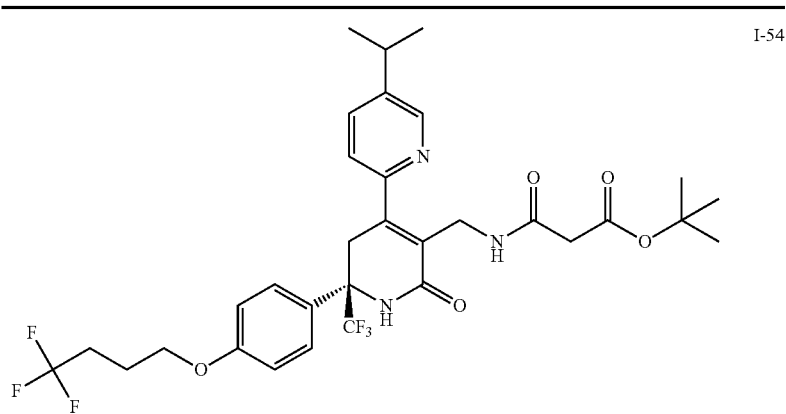
I-54
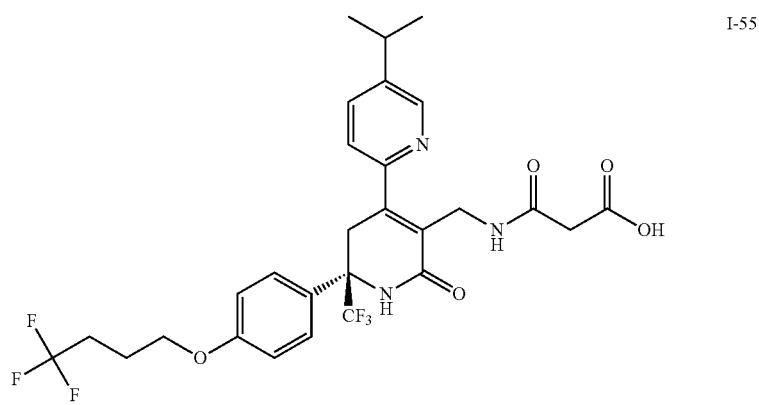
I-55
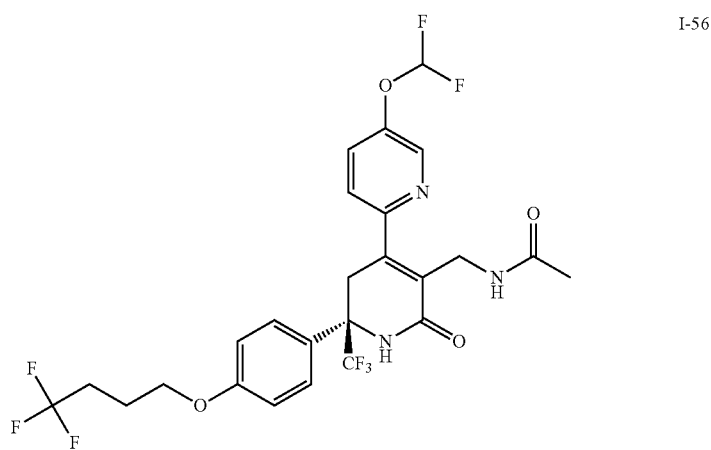
I-56

TABLE 5-continued
| | |
|---|---|
| 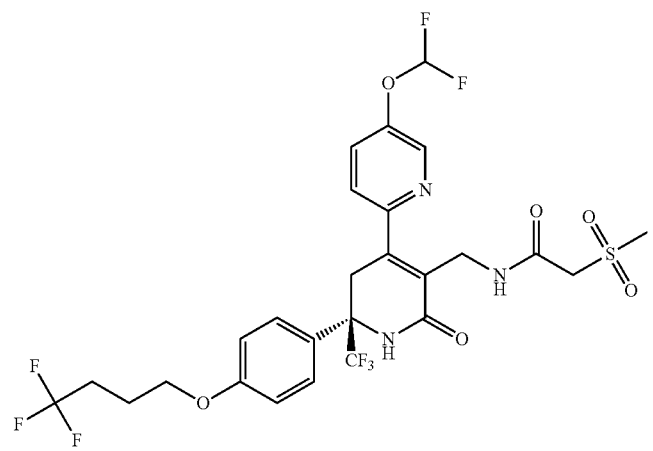 [SMILES: CS(=O)(=O)CC(=O)NCC1=C(c2ccc(OC(F)F)cn2)C[C@](c2ccc(OCCCC(F)(F)F)cc2)(C(F)(F)F)NC1=O] | I-57 |
| 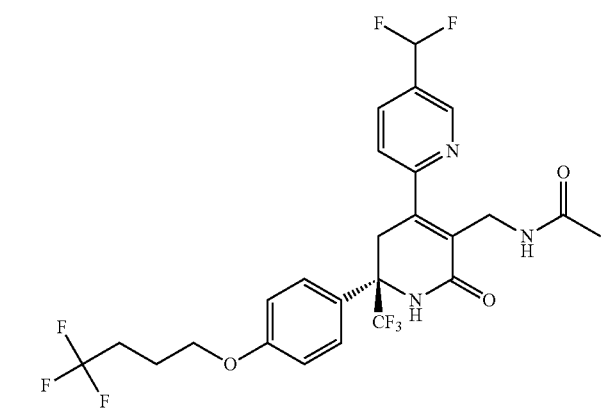 [SMILES: CC(=O)NCC1=C(c2ccc(C(F)F)cn2)C[C@](c2ccc(OCCCC(F)(F)F)cc2)(C(F)(F)F)NC1=O] | I-58 |
| 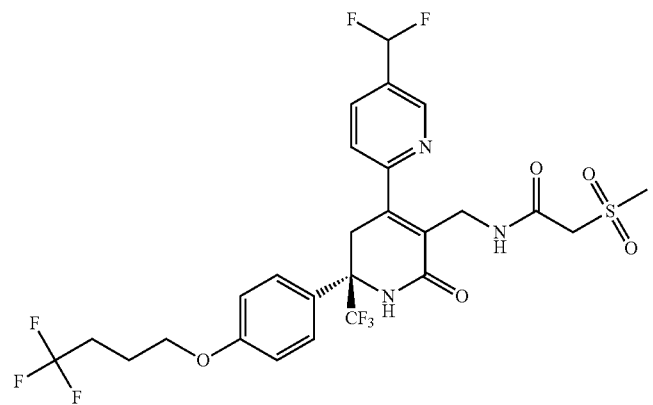 [SMILES: CS(=O)(=O)CC(=O)NCC1=C(c2ccc(C(F)F)cn2)C[C@](c2ccc(OCCCC(F)(F)F)cc2)(C(F)(F)F)NC1=O] | I-59 |
| 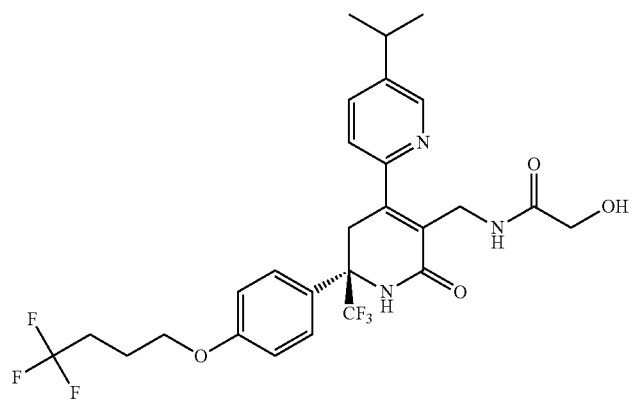 [SMILES: CC(C)c1ccc(C2=C(CNC(=O)CO)C(=O)N[C@@](c3ccc(OCCCC(F)(F)F)cc3)(C(F)(F)F)C2)nc1] | I-60 |

TABLE 5-continued
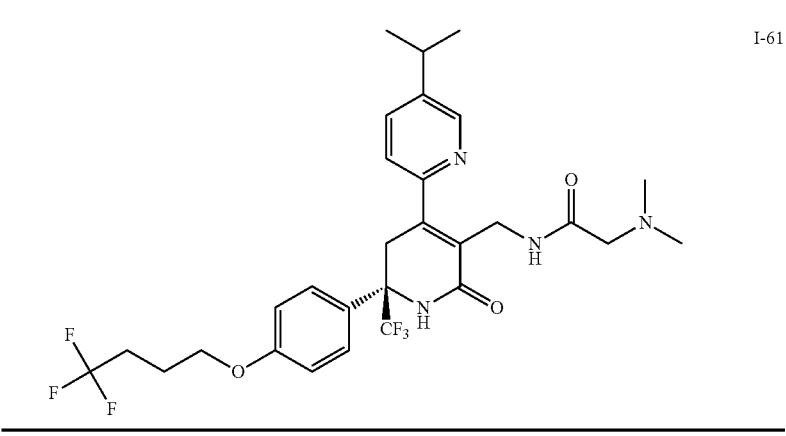
I-61
TABLE 6
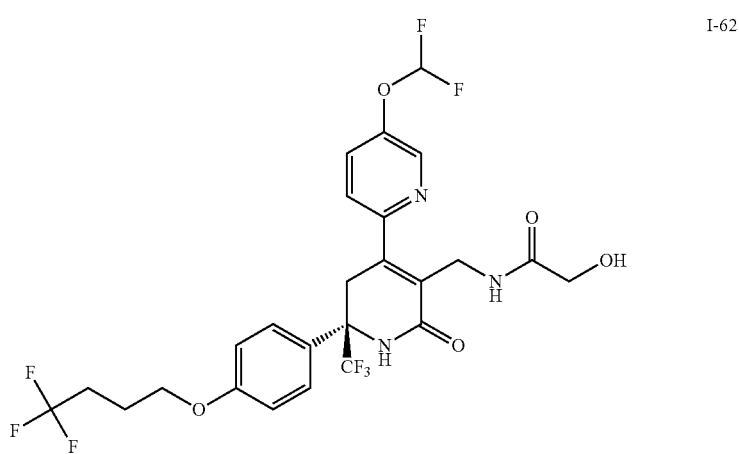
I-62
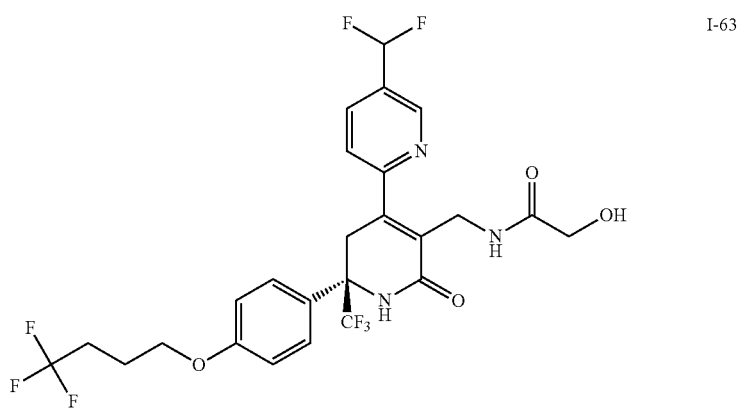
I-63

TABLE 6-continued
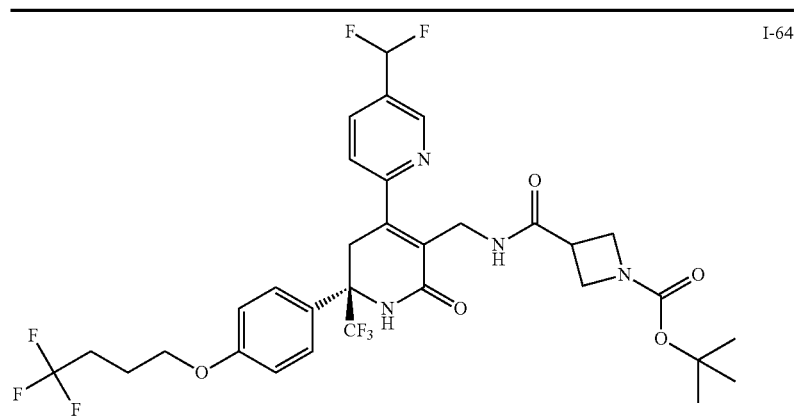
I-64
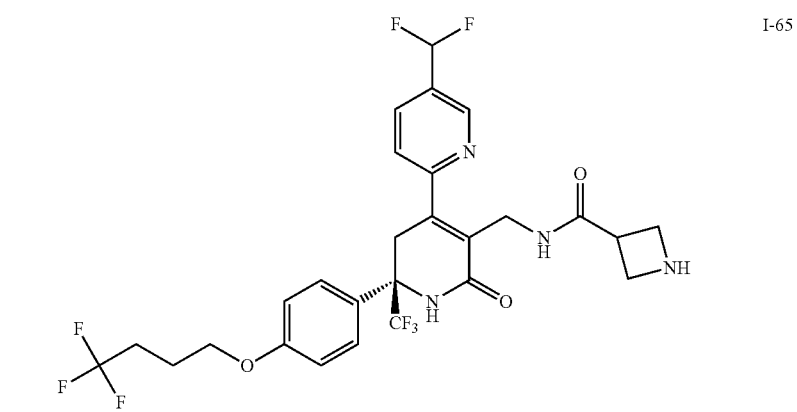
I-65
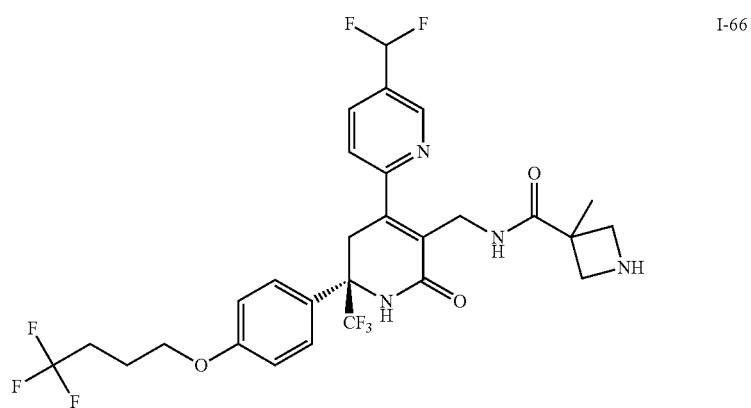
I-66
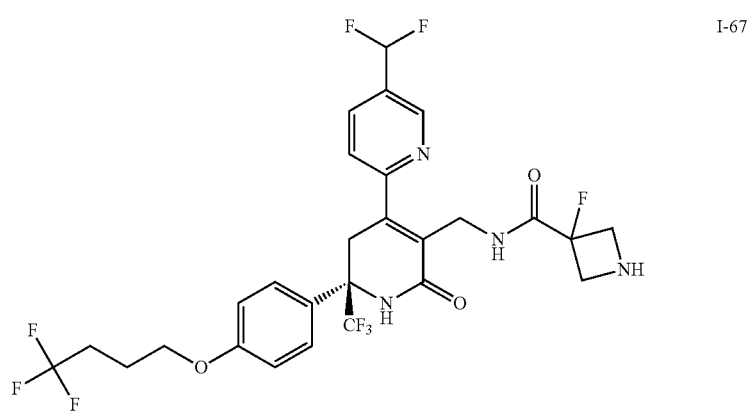
I-67

TABLE 6-continued

I-68

I-69

I-70

I-71

TABLE 6-continued
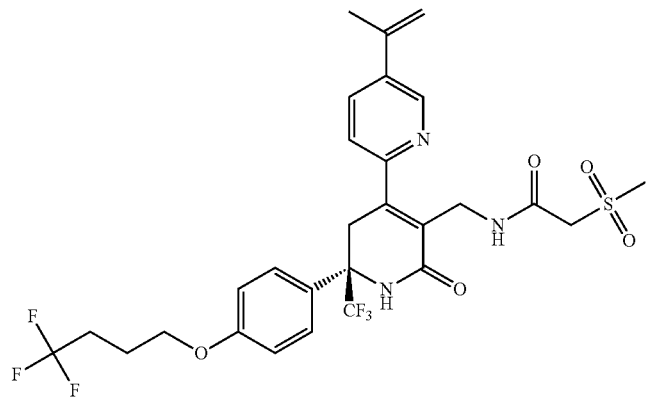 [SMILES: C=C(C)c1ccc(C2=C(CNC(=O)CS(C)(=O)=O)C(=O)N[C@@](c3ccc(OCCCC(F)(F)F)cc3)(C(F)(F)F)C2)nc1]
I-72
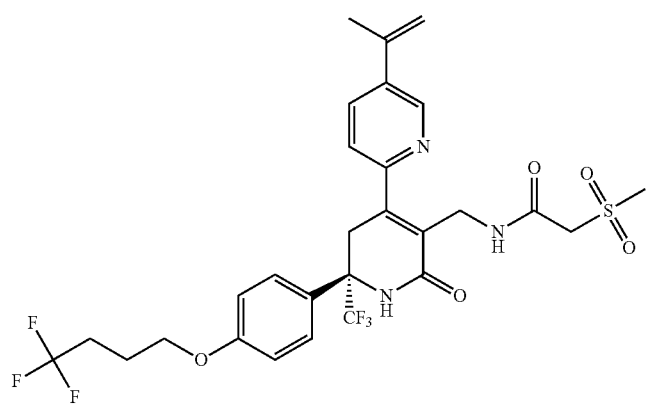 [SMILES: C=C(C)c1ccc(C2=C(CNC(=O)CS(C)(=O)=O)C(=O)N[C@](c3ccc(OCCCC(F)(F)F)cc3)(C(F)(F)F)C2)nc1]
I-73
TABLE 7
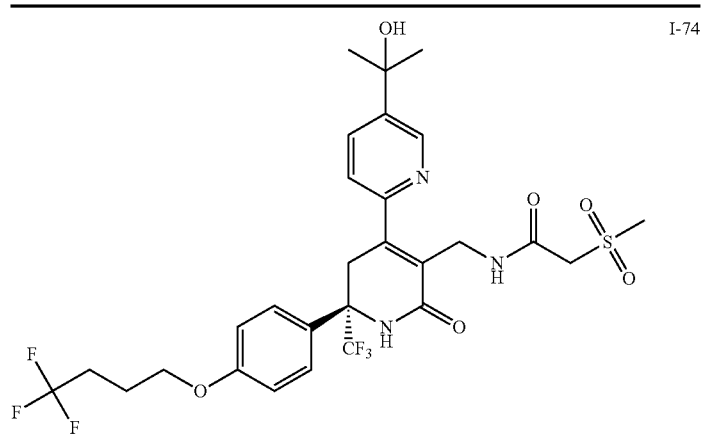
I-74

TABLE 7-continued
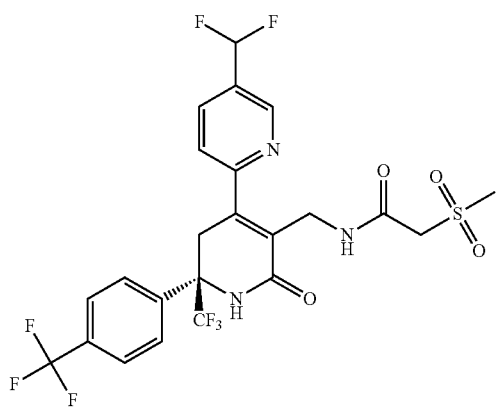 [SMILES: CS(=O)(=O)CC(=O)NCC1=C(c2ccc(C(F)F)cn2)C[C@](c2ccc(C(F)(F)F)cc2)(C(F)(F)F)NC1=O]
I-75
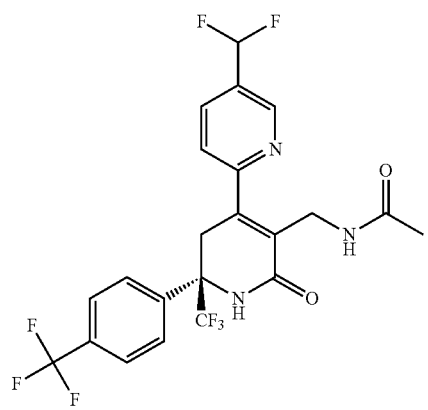 [SMILES: CC(=O)NCC1=C(c2ccc(C(F)F)cn2)C[C@](c2ccc(C(F)(F)F)cc2)(C(F)(F)F)NC1=O]
I-76
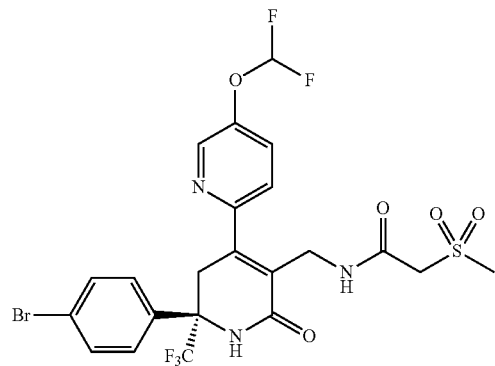 [SMILES: CS(=O)(=O)CC(=O)NCC1=C(c2ccc(OC(F)F)cn2)C[C@@](c2ccc(Br)cc2)(C(F)(F)F)NC1=O]
I-77
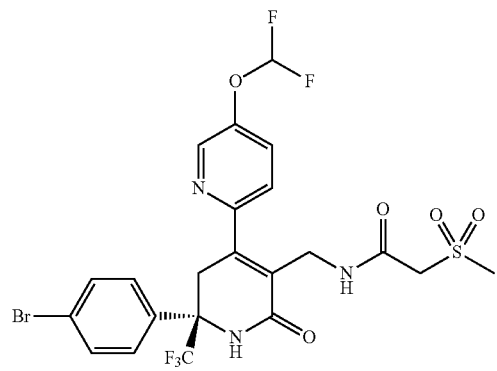 [SMILES: CS(=O)(=O)CC(=O)NCC1=C(c2ccc(OC(F)F)cn2)C[C@](c2ccc(Br)cc2)(C(F)(F)F)NC1=O]
I-78

TABLE 7-continued
I-79
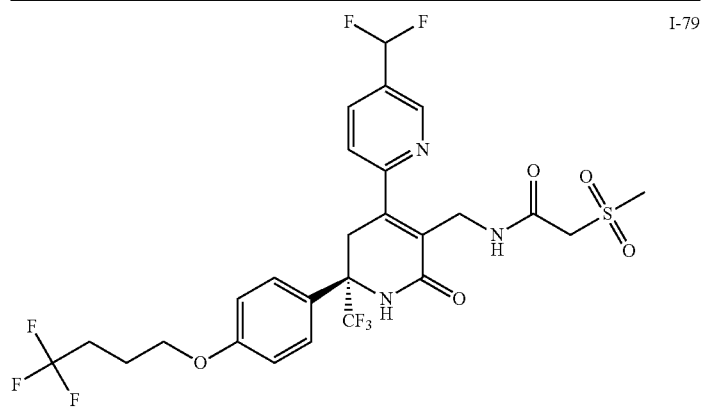
I-80
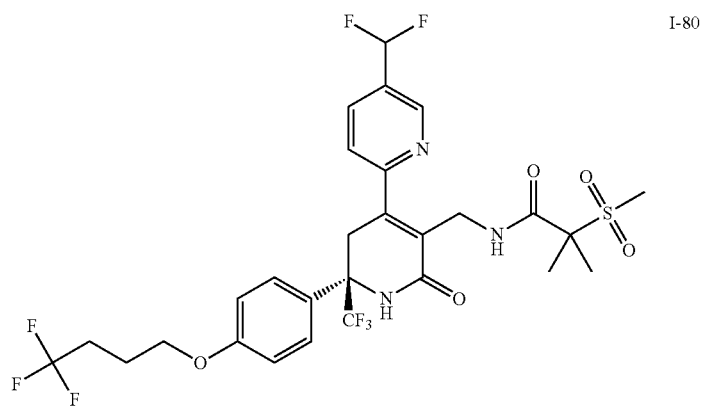
I-81
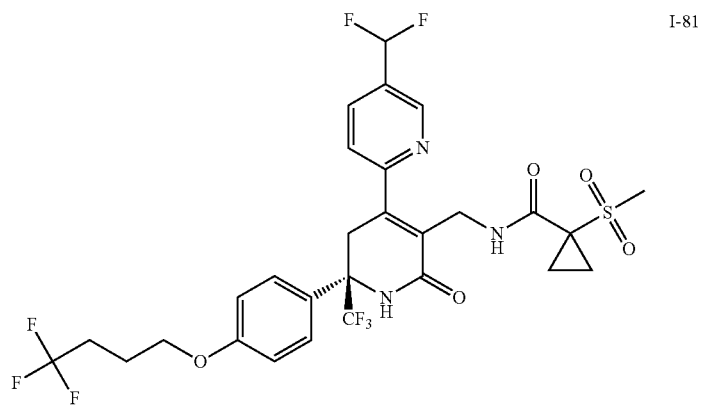
I-82
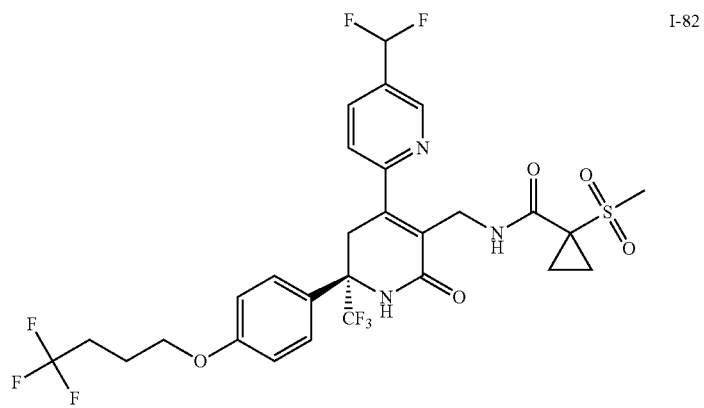

TABLE 7-continued
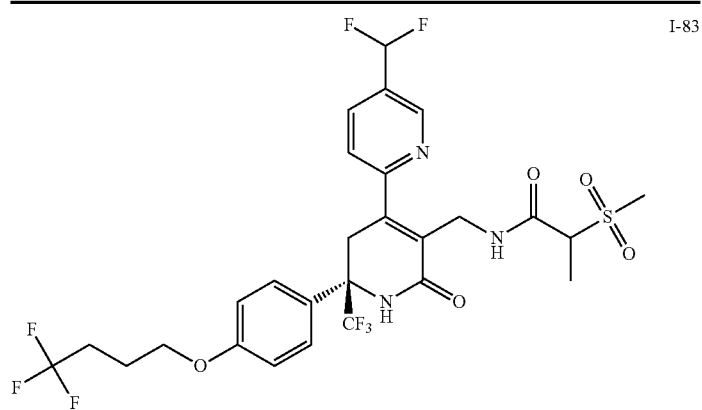
I-83
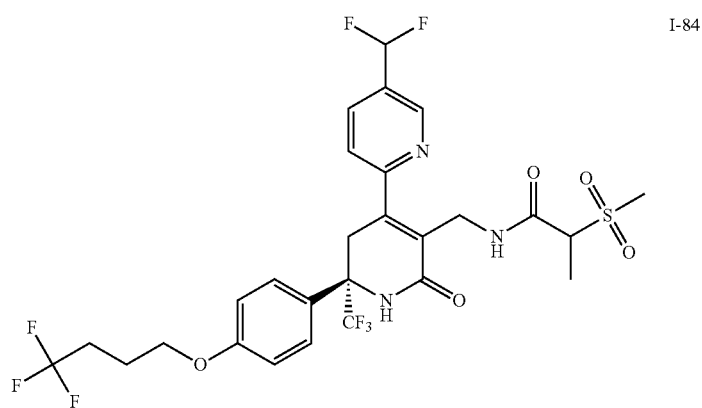
I-84
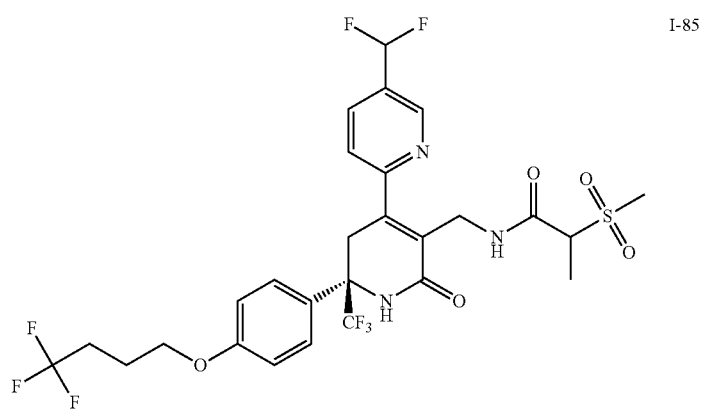
I-85

TABLE 8
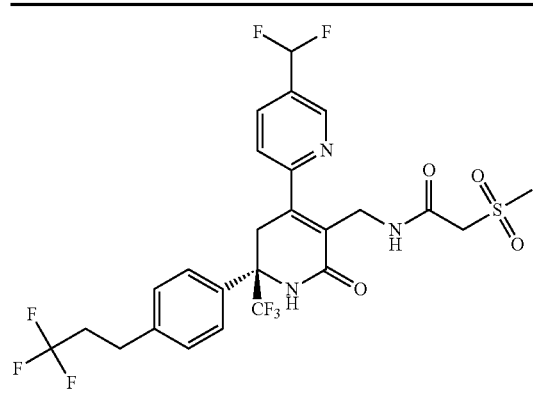
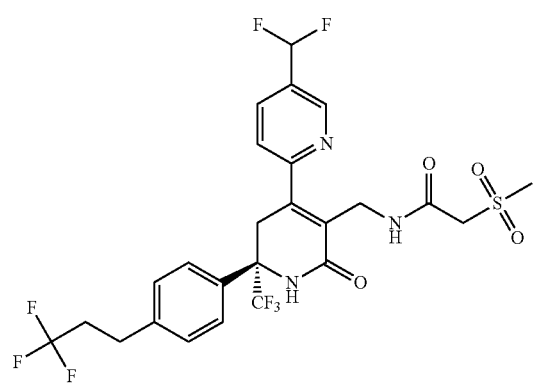 [SMILES: CS(=O)(=O)CC(=O)NCC1=C(c2ccc(C(F)F)cn2)C[C@@](c2ccc(CCC(F)(F)F)cc2)(C(F)(F)F)NC1=O]
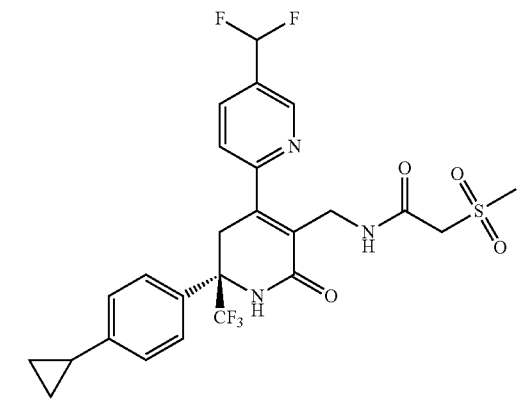 [SMILES: CS(=O)(=O)CC(=O)NCC1=C(c2ccc(C(F)F)cn2)C[C@](c2ccc(C3CC3)cc2)(C(F)(F)F)NC1=O]
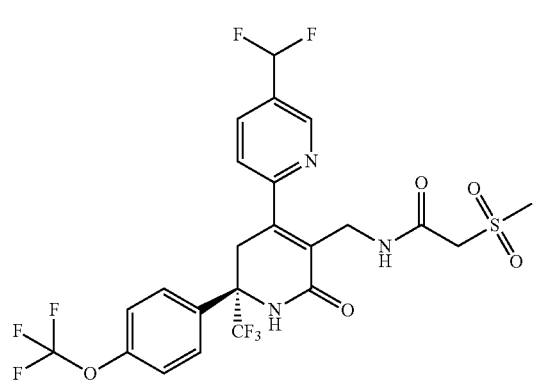 [SMILES: CS(=O)(=O)CC(=O)NCC1=C(c2ccc(C(F)F)cn2)C[C@@](c2ccc(OC(F)(F)F)cc2)(C(F)(F)F)NC1=O]
TABLE 8-continued
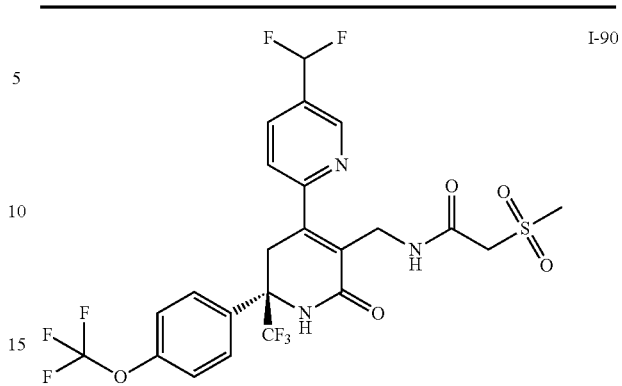

TABLE 8-continued
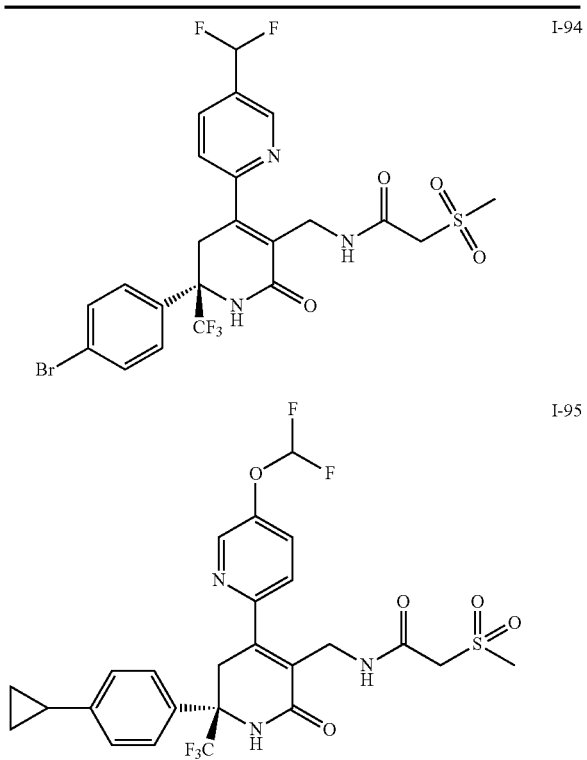
I-94
I-95
TABLE 8-continued
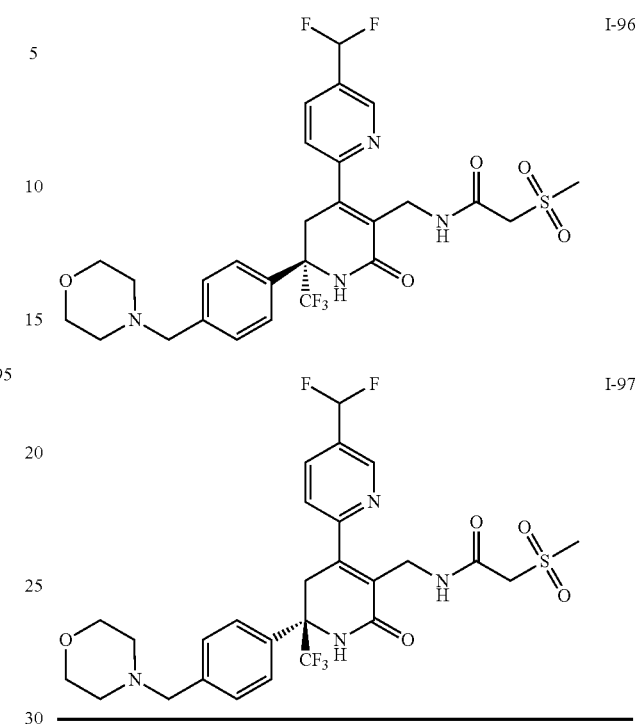
I-96
I-97
TABLE 9
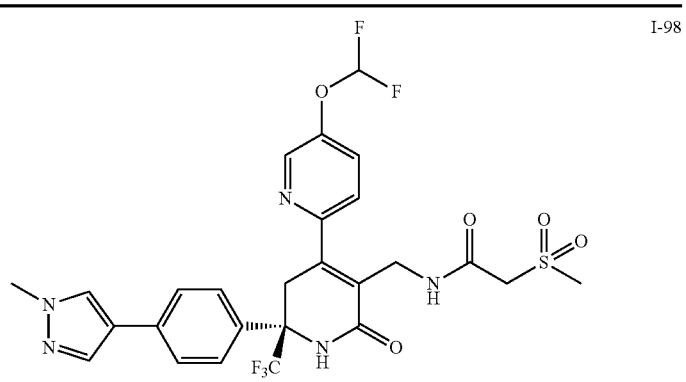
I-98
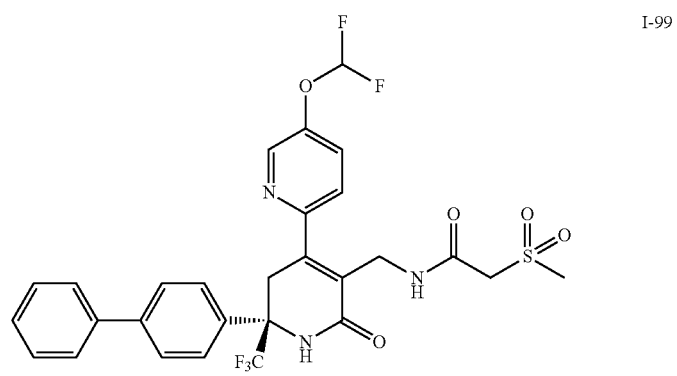
I-99

TABLE 9-continued
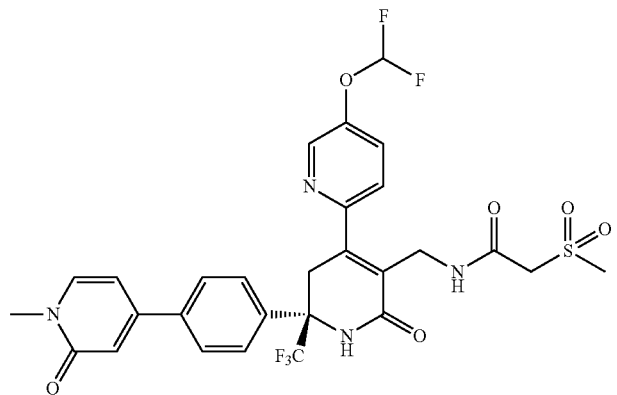 [SMILES: Cn1ccc(-c2ccc([C@]3(C(F)(F)F)CC(c4ccc(OC(F)F)cn4)=C(CNC(=O)CS(C)(=O)=O)C(=O)N3)cc2)cc1=O]
I-100
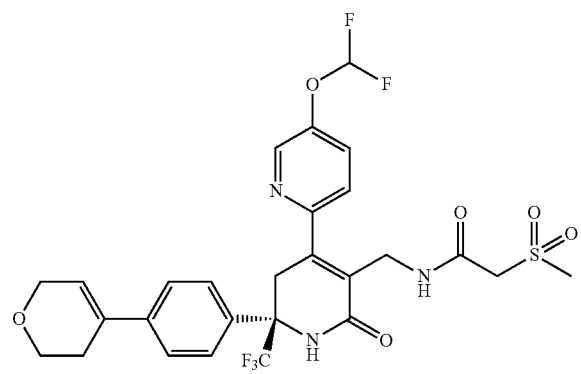 [SMILES: CS(=O)(=O)CC(=O)NCC1=C(c2ccc(OC(F)F)cn2)C[C@](c2ccc(C3=CCOCC3)cc2)(C(F)(F)F)NC1=O]
I-101
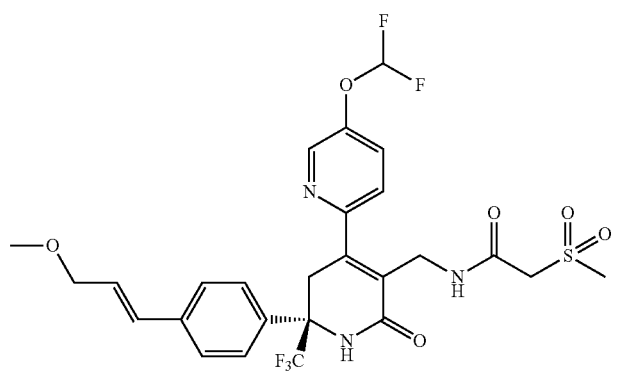 [SMILES: COC/C=C/c1ccc([C@]2(C(F)(F)F)CC(c3ccc(OC(F)F)cn3)=C(CNC(=O)CS(C)(=O)=O)C(=O)N2)cc1]
I-102
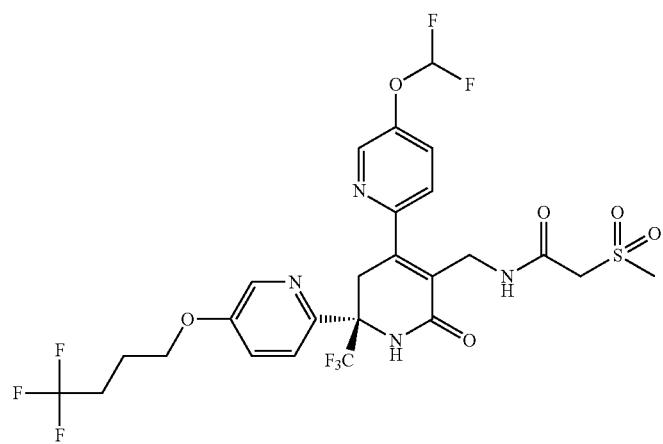 [SMILES: CS(=O)(=O)CC(=O)NCC1=C(c2ccc(OC(F)F)cn2)C[C@](c2ccc(OCCCC(F)(F)F)cn2)(C(F)(F)F)NC1=O]
I-103

TABLE 9-continued
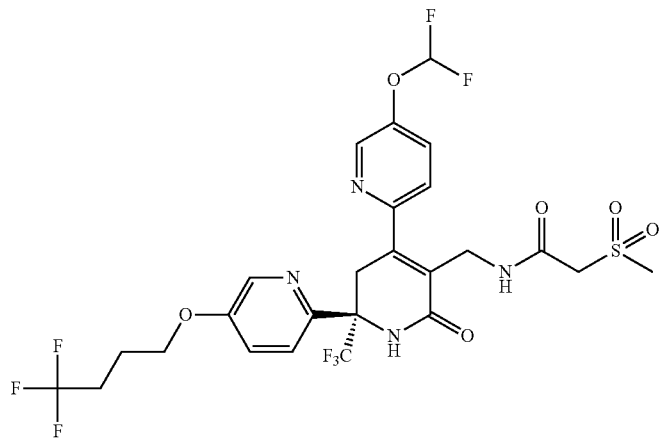 [SMILES: CS(=O)(=O)CC(=O)NCC1=C(c2ccc(OC(F)F)cn2)C[C@@](c2ccc(OCCCC(F)(F)F)cn2)(C(F)(F)F)NC1=O]
I-104
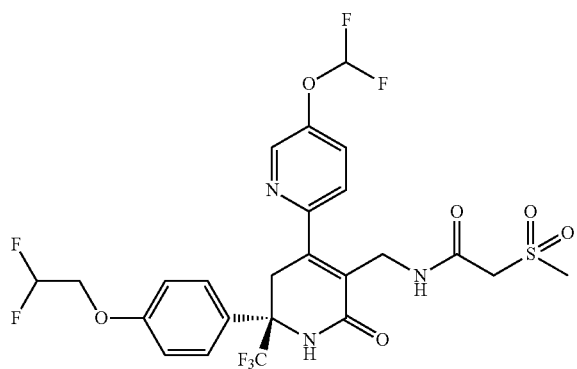 [SMILES: CS(=O)(=O)CC(=O)NCC1=C(c2ccc(OC(F)F)cn2)C[C@](c2ccc(OCC(F)F)cc2)(C(F)(F)F)NC1=O]
I-105
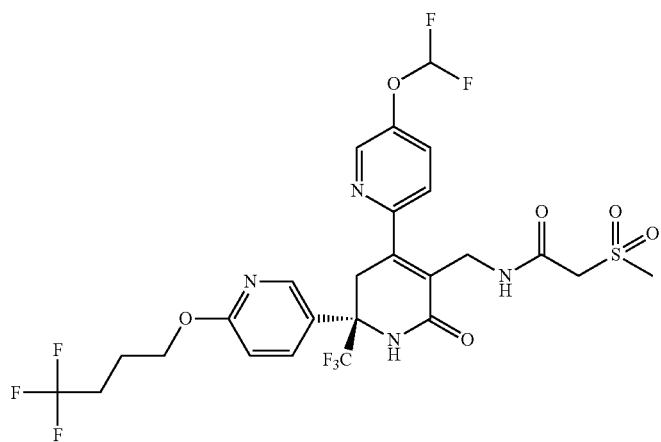 [SMILES: CS(=O)(=O)CC(=O)NCC1=C(c2ccc(OC(F)F)cn2)C[C@](c2ccc(OCCCC(F)(F)F)nc2)(C(F)(F)F)NC1=O]
I-106

TABLE 9-continued
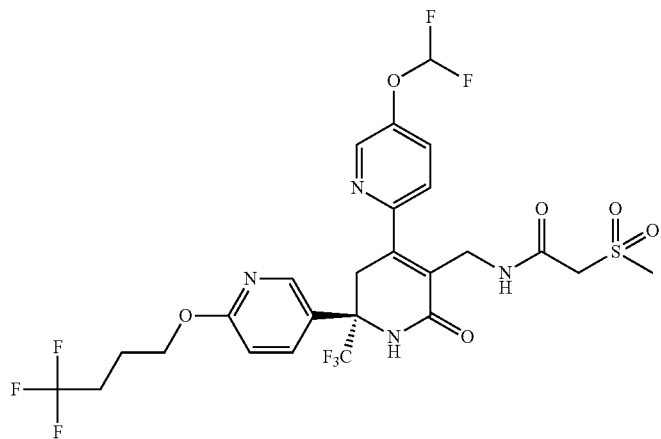 [SMILES: CS(=O)(=O)CC(=O)NCC1=C(c2ccc(OC(F)F)cn2)C[C@@](c2ccc(OCCCC(F)(F)F)nc2)(C(F)(F)F)NC1=O]
I-107
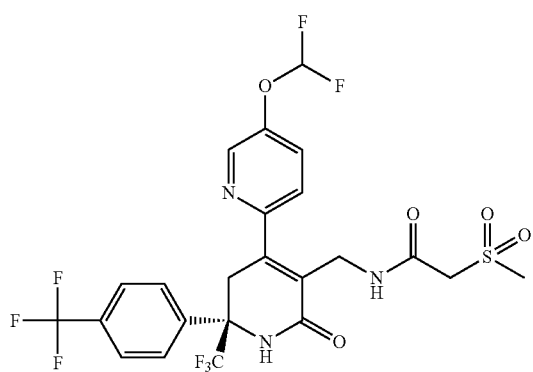 [SMILES: CS(=O)(=O)CC(=O)NCC1=C(c2ccc(OC(F)F)cn2)C[C@](c2ccc(C(F)(F)F)cc2)(C(F)(F)F)NC1=O]
I-108
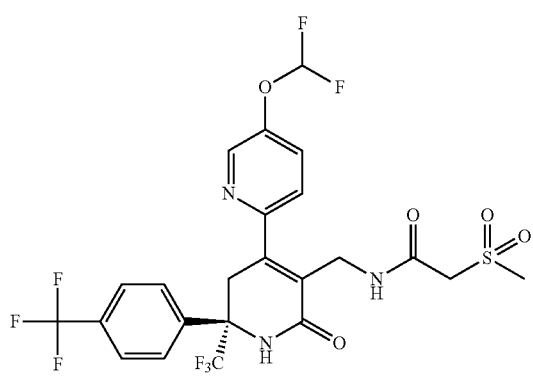
I-109

TABLE 10
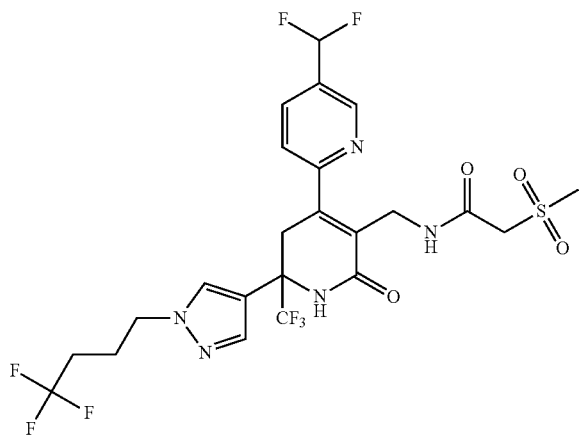 [SMILES: CS(=O)(=O)CC(=O)NCC1=C(c2ccc(C(F)F)cn2)CC(c2cnn(CCCC(F)(F)F)c2)(C(F)(F)F)NC1=O]
I-110
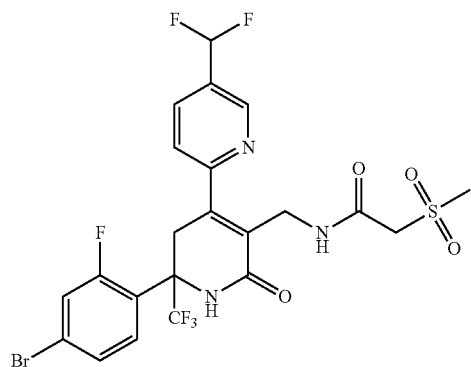 [SMILES: CS(=O)(=O)CC(=O)NCC1=C(c2ccc(C(F)F)cn2)CC(c2ccc(Br)cc2F)(C(F)(F)F)NC1=O]
I-111
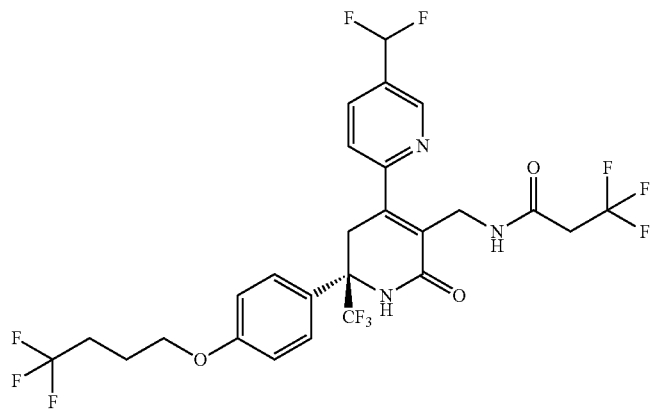 [SMILES: O=C(CC(F)(F)F)NCC1=C(c2ccc(C(F)F)cn2)C[C@](c2ccc(OCCCC(F)(F)F)cc2)(C(F)(F)F)NC1=O]
I-112
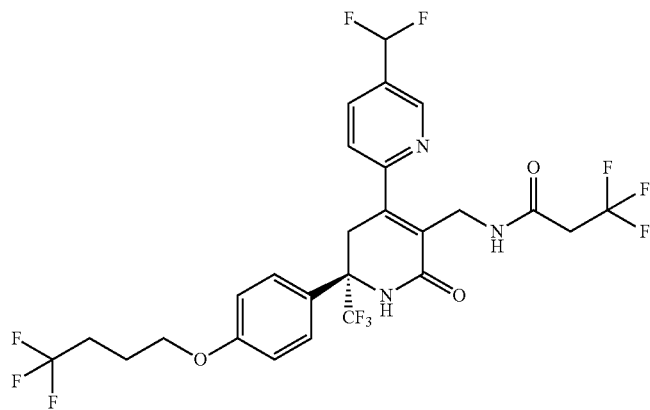 [SMILES: O=C(CC(F)(F)F)NCC1=C(c2ccc(C(F)F)cn2)C[C@@](c2ccc(OCCCC(F)(F)F)cc2)(C(F)(F)F)NC1=O]
I-113

TABLE 10-continued

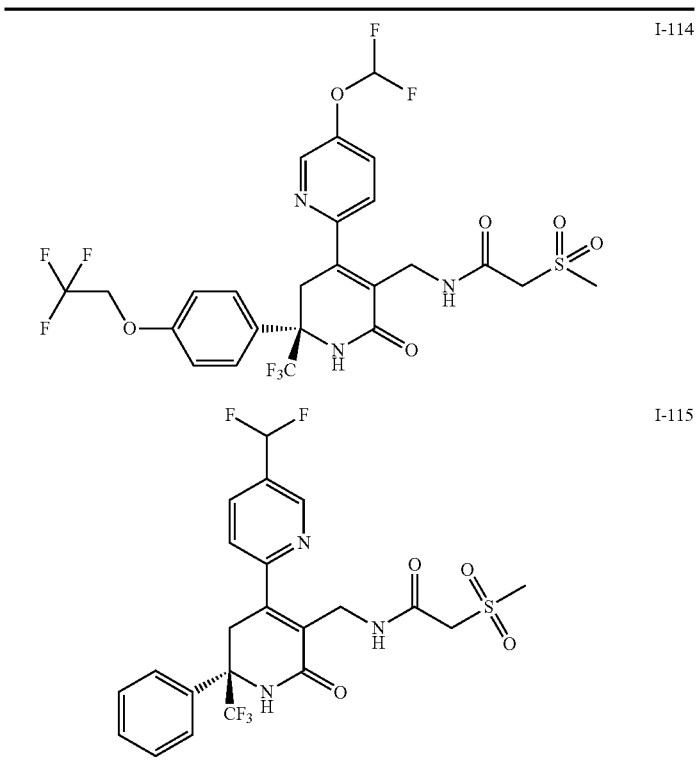

For I-83, I-84, and I-85, each of which is a single compound, the stereochemistry of a methyl group included in $R^1$ has not been proved.

I-110 and I-11 is each a racemate.

The physical data of the compounds are shown below.

In the tables, LC (min) indicates retention time in LC/MS (liquid chromatography/mass spectrometry), MS (M+H) indicates mass in LC/MS, and LCMS Method indicates any of the following measurement conditions for LC/MS.

Measurement Condition A
Column: ACQUITY UPLC (registered trademark) BEH C18 (1.7 μm i.d.2.1×50 mm) (Waters)
Flow rate: 0.8 mL/min
UV detection wavelength: 254 nm
Mobile phases: [A] is 0.1% formic acid solution, and [B] is 0.1% formic acid in acetonitrile solvent.
Gradient: linear gradient of 5% to 100% solvent [B] for 3.5 minutes was performed, and then 100% solvent [B] was maintained for 0.5 minute.

Measurement Condition B
Column: Shim-pack XR-ODS (2.2 μm, i.d.50×3.0 mm) (Shimadzu)
Flow rate: 1.6 mL/min
UV detection wavelength: 254 nm
Mobile phases: [A] is 0.1% formic acid solution, and [B] is 0.1% formic acid in acetonitrile solvent.
Gradient: linear gradient of 10% to 100% solvent [B] for 3 minutes was performed, and 100% solvent [B] was maintained for 0.5 minute.

Measurement Condition C
Column: ACQUITY UPLC (registered trademark) BEH C18 (1.7 μm i.d.2.1×50 mm)(Waters)
Flow rate: 0.55 mL/min
UV detection wavelength: 254 nm
Mobile phases: [A] is 0.1% formic acid solution, and [B] is 0.1% formic acid in acetonitrile solvent.
Gradient: linear gradient of 5% to 100% solvent [B] for 3 minutes was performed, and then 100% solvent [B] was maintained for 0.5 minute.

Measurement Condition D
Column: ACQUITY UPLC (registered trademark) BEH C18 (1.7 μm i.d.2.1×50 mm) (Waters)
Flow rate: 0.8 mL/min
UV detection wavelength: 254 nm
Mobile phases: [A] is 0.1% formic acid solution, and [B] is 0.1% formic acid in acetonitrile solvent.
Gradient: linear gradient of 5% to 100% solvent [B] for 3.5 minutes was performed, and then 100% solvent [B] was maintained for 0.5 minute.

Measurement Condition E
Column: ACQUITY UPLC (registered trademark) BEH C18 (1.7 μm i.d.2.1×50 mm) (Waters)
Flow rate: 0.8 mL/min
UV detection wavelength: 254 nm
Mobile phase: [A] is 10 mmol/L aqueous solution of ammonium carbonate, and [B] is acetonitrile.
Gradient: linear gradient of 5% to 100% solvent [B] for 3.5 minutes was performed, and then 100% solvent [B] was maintained for 0.5 minute.

TABLE 11

| No. | LCMS Method | LC (min) | MS (M + H) |
|---|---|---|---|
| I-1 | C | 2.47 | 565 |
| I-3 | C | 2.29 | 566 |
| I-4 | C | 2.09 | 530 |
| I-5 | C | 2.23 | 567 |

TABLE 11-continued

| No. | LCMS Method | LC (min) | MS (M + H) |
|---|---|---|---|
| I-6 | C | 1.97 | 531 |
| I-7 | C | 2.30 | 546 |
| I-8 | C | 2.19 | 556 |
| I-9 | C | 1.97 | 546 |
| I-10 | C | 2.17 | 608 |
| I-11 | A | 2.08 | 546 |
| I-12 | A | 2.15 | 624 |
| I-13 | A | 2.40 | 614 |
| I-14 | A | 2.33 | 574 |
| I-15 | A | 2.37 | 586 |
| I-16 | A | 2.51 | 602 |
| I-17 | A | 2.30 | 599 |
| I-18 | A | 2.33 | 582 |
| I-19 | A | 2.55 | 650 |
| I-20 | A | 2.42 | 607 |
| I-21 | A | 2.64 | 650 |
| I-22 | A | 2.35 | 652 |
| I-23 | A | 2.56 | 644 |
| I-24 | A | 2.21 | 600 |
| I-25 | C | 2.23 | 544 |
| I-26 | A | 2.42 | 598 |
| I-27 | A | 2.37 | 583 |
| I-28 | A | 2.48 | 591 |
| I-29 | A | 2.23 | 620 |
| I-30 | A | 2.16 | 555 |
| I-31 | A | 1.96 | 546 |
| I-32 | A | 2.19 | 589 |
| I-33 | A | 2.40 | 590 |
| I-34 | A | 2.09 | 616 |
| I-35 | A | 2.28 | 558 |
| I-36 | A | 2.12 | 588 |
| I-37 | D | 2.33 | 571 |
| I-38 | D | 2.51 | 599 |
| I-39 | D | 2.49 | 597 |
| I-40 | A | 2.08 | 562 |
| I-41 | A | 2.19 | 590 |
| I-42 | A | 1.84 | 574 |
| I-43 | A | 2.34 | 636 |
| I-44 | A | 2.35 | 648 |
| I-45 | A | 2.58 | 611 |
| I-46 | A | 2.78 | 636 |
| I-47 | A | 1.93 | 652 |
| I-48 | A | 1.92 | 664 |
| I-49 | A | 2.26 | 594 |
| I-50 | A | 2.41 | 586 |
| I-51 | A | 2.06 | 558 |
| I-53 | A | 2.29 | 600 |
| I-54 | A | 2.74 | 658 |
| I-55 | A | 2.30 | 602 |
| I-56 | A | 2.28 | 582 |
| I-57 | A | 2.32 | 660 |
| I-58 | A | 2.22 | 566 |
| I-59 | A | 2.27 | 644 |
| I-60 | C | 2.33 | 574 |

TABLE 12

| No. | LCMS Method | LC (min) | MS (M + H) |
|---|---|---|---|
| I-61 | C | 1.99 | 601 |
| I-62 | C | 2.30 | 598 |
| I-63 | C | 2.25 | 582 |
| I-64 | A | 2.45 | 707 |
| I-65 | A | 2.03 | 607 |
| I-66 | A | 1.98 | 621 |
| I-67 | A | 1.98 | 625 |
| I-68 | A | 2.28 | 562 |
| I-69 | A | 2.30 | 640 |
| I-70 | A | 2.31 | 672 |
| I-71 | A | 2.31 | 672 |
| I-72 | A | 2.38 | 634 |
| I-73 | E | 2.38 | 634 |
| I-74 | A | 1.94 | 652 |
| I-75 | A | 2.02 | 586 |
| I-76 | A | 1.97 | 508 |
| I-77 | B | 2.00 | 612 |
| I-78 | B | 2.00 | 612 |
| I-79 | E | 2.20 | 644 |
| I-80 | A | 2.35 | 672 |
| I-81 | A | 2.36 | 670 |
| I-82 | A | 2.36 | 670 |
| I-83 | A | 2.27 | 658 |
| I-84 | A | 2.27 | 658 |
| I-85 | A | 2.27 | 658 |
| I-86 | A | 2.09 | 614 |
| I-87 | A | 2.09 | 614 |
| I-88 | A | 2.03 | 558 |
| I-89 | A | 2.32 | 602 |
| I-90 | A | 2.32 | 602 |
| I-91 | A | 2.07 | 616 |
| I-92 | A | 2.07 | 616 |
| I-93 | A | 2.00 | 596 |
| I-94 | A | 2.00 | 596 |
| I-95 | B | 2.24 | 574 |
| I-96 | A | 1.25 | 617 |
| I-97 | A | 1.25 | 617 |
| I-98 | B | 1.71 | 614 |
| I-99 | B | 2.16 | 610 |
| I-100 | B | 1.76 | 641 |
| I-101 | B | 1.87 | 616 |
| I-102 | B | 1.92 | 604 |
| I-103 | A | 2.10 | 661 |
| I-104 | A | 2.11 | 662 |
| I-105 | A | 1.91 | 614 |
| I-106 | B | 2.11 | 662 |
| I-107 | B | 2.11 | 661 |
| I-108 | B | 2.04 | 602 |
| I-109 | B | 2.04 | 602 |
| I-110 | A | 1.83 | 618 |
| I-111 | A | 2.06 | 614 |
| I-112 | A | 2.47 | 634 |
| I-113 | A | 2.47 | 634 |
| I-114 | B | 2.03 | 632 |
| I-115 | A | 1.79 | 518 |

NMR analysis of each Example was performed by 300 MHz using DMSO-$d_6$ or $CDCl_3$.

TABLE 13

| | |
|---|---|
| I-1 | 1H-NMR (CDCl3) δ: 2.02-2.10 (m, 2H), 2.25-2.39 (m, 5H), 2.71 (s, 3H), 3.28 (d, J = 17.6 Hz, 1H), 3.47 (d, J = 17.6 Hz, 1H), 3.83 (dd, J = 13.6, 6.6 Hz, 1H), 3.91 (dd, J = 13.6, 6.6 Hz, 1H), 4.03 (t, J = 5.9 Hz, 2H), 5.46 (t, J = 6.6 Hz, 1H), 6.58 (s, 1H), 6.94 (d, J = 8.8 Hz, 2H), 7.07 (d, J = 8.2 Hz, 2H), 7.23 (d, J = 8.2 Hz, 2H), 7.43 (d, J = 8.8 Hz, 2H). |
| I-4 | 1H-NMR (CDCl3) δ: 1.90 (s, 3H), 2.01-2.09 (m, 2H), 2.26-2.38 (m, 5H), 3.48 (d, J = 17.6 Hz, 1H), 3.67 (d, J = 17.6 Hz, 1H), 3.93-4.04 (m, 3H), 4.23 (dd, J = 14.3, 7.0 Hz, 1H), 6.35 (s, 1H), 6.43 (brs, 1H), 6.90 (d, J = 8.4 Hz, 2H), 7.39 (d, J = 8.0 Hz, 1H), 7.47 (d, J = 8.4 Hz, 2H), 7.56 (d, J = 8.0 Hz, 1H), 8.49 (s, 1H). |
| I-9 | 1H-NMR (CDCl3) δ: 1.89 (s, 3H), 2.00-2.10 (m, 2H), 2.25-2.37 (m, 2H), 3.50 (d, J = 17.6 Hz, 1H), 3.64 (d, J = 17.6 Hz, 1H), 3.93-4.06 (m, 3H), 4.22 (dd, J = 14.0, 6.7 Hz, 1H), 4.76 (s, 2H), 6.35 (s, 1H), 6.43 (brs, 1H), 6.91 (d, J = 8.7 Hz, 2H), 7.43-7.50 (m, 3H), 7.79 (d, J = 8.2 Hz, 1H), 8.66 (s, 1H). |

TABLE 13-continued

I-10  2.24-2.35 (m, 2H), 2.38 (s, 3H), 3.12 (s, 3H), 3.38 (d, J = 17.6 Hz, 1H), 3.74 (d, J = 17.6 Hz, 1H), 3.84-3.96 (m, 2H), 3.98-4.08 (m, 3H), 4.28 (dd, J = 14.3, 6.8 Hz, 1H), 6.91 (d, J = 8.3 Hz, 2H), 6.98 (s, 1H), 7.33 (d, J = 7.0 Hz, 1H), 7.49-7.56 (m, 3H), 7.68 (brs, 1H), 8.52 (s, 1H).

I-47  1H-NMR (CDCl3) δ: 1.63 (s, 6H), 1.93 (s, 1H), 2.01-2.07 (m, 2H), 2.24-2.36 (m, 2H), 3.16 (s, 3H), 3.35 (d, J = 17.6 Hz, 1H), 3.81 (d, J = 17.6 Hz, 1H), 3.89 (d, J = 14.0 Hz, 1H), 3.92 (d, J = 13.6 Hz, 1H), 4.00 (t, J = 6.0 Hz, 2H), 4.18 (d, J = 13.6 Hz, 1H), 4.30 (dd, J = 7.6, 14.0 Hz, 1H), 6.90 (d, J = 8.8 Hz, 2H), 7.35 (s, 1H), 7.44 (d, J = 8.0 Hz, 1H), 7.54 (d, J = 8.0 Hz, 2H), 7.86 (d, J = 8.0 Hz, 1H), 7.92 (br.s, 1H), 8.82 (s, 1H).

I-52  1H-NMR (CDCl3) δ: 1.48 (3H, s), 1.50 (3H, s), 1.63 (6H, s), 2.01-2.08 (2H, m), 2.24-2.36 (2H, m), 3.57 (2H, dd, J = 44.9, 17.4 Hz), 4.01 (2H, t, J = 5.1 Hz), 4.18 (2H, ddd, J = 51.6, 14.2, 5.8 Hz), 6.52 (1H, s), 6.91 (2H, d, J = 8.9 Hz), 7.39 (1H, d, J = 8.2 Hz), 7.49 (3H, m), 7.90 (1H, dd, J = 8.3, 2.4 Hz), 8.83 (1H, d, J = 2.1 Hz).

I-59  1H-NMR (CDCl3) δ: 2.02-2.09 (m, 2H), 2.25-2.37 (m, 2H), 3.50 (d, J = 17.6 Hz, 1H), 3.67 (d, J = 17.6 Hz, 1H), 3.89 (dd, J = 5.2, 14.4 Hz, 1H), 4.02 (t, J = 6.0 Hz, 2H), 4.02 (dd, J = 6.8, 14.4 Hz, 1H), 6.49 (br.t, J = 5.6 Hz, 1H), 6.74 (d, JH-F = 56.0 Hz, 1H), 6.91 (d, J = 9.2 Hz, 2H), 7.16 (s, 1H), 7.49 (d, J = 9.2 Hz, 2H), 7.70 (d, J = 8.4 Hz, 1H), 7.92 (d, J = 8.4 Hz, 1H), 8.82 (s, 1H).

I-75  1H-NMR (CDCl3) δ: 3.19 (s, 3H), 3.36 (d, J = 17.6 Hz, 1H), 3.89 (d, J = 13.6 Hz, 1H), 3.95 (d, J = 13.6 Hz, 1H), 3.97 (d, J = 17.6 Hz, 1H), 4.27 (d, J = 13.6 Hz, 1H), 4.33 (dd, J = 8.0, 13.6 Hz, 1H), 6.76 (d, JH-F = 55.6 Hz, 1H), 6.90 (d, J = 8.0 Hz, 1H), 7.00 (d, J = 8.0 Hz, 2H), 7.77 (s, 1H), 7.83 (d, J = 8.0 Hz, 2H), 7.89 (d, J = 8.0 Hz, 1H), 8.00 (br.d, J = 6.0 Hz, 1H), 8.85 (s, 1H).

I-88  1H-NMR (CDCl3) δ: 0.70 (m, 2H), 0.97 (m, 2H), 1.87 (m, 1H), 3.17 (s, 3H), 3.34 (d, J = 17.6 Hz, 1H), 3.69-3.86 (m, 2H), 3.95 (d, J = 14.0 Hz, 1H), 4.22 (d, J = 14.0 Hz, 1H), 4.27 (dd, J = 7.2, 14.0 Hz, 1H), 6.75 (d, JH-F = 55.6 Hz, 1H), 7.08 (d, J = 8.4 Hz, 2H), 7.48 (d, J = 8.4 Hz, 2H), 7.59 (s, 1H), 7.60 (d, J = 8.4 Hz, 1H), 7.87 (d, J = 8.0 Hz, 1H), 8.00 (br.s, 1H), 8.84 (s, 1H).

I-90  1H-NMR (CDCl3) δ: 3.19 (s, 3H), 3.34 (d, J = 18.0 Hz, 1H), 3.81 (d, J = 14.0 Hz, 1H), 3.80 (d, J = 18.0 Hz, 1H), 3.95 (d, J = 14.0 Hz, 1H), 4.25 (d, J = 14.0 Hz, 1H), 4.32 (dd, J = 8.0, 14.0 Hz, 1H), 6.76 (d, JH-F = 55.6 Hz, 1H), 7.27 (d, J = 8.0 Hz, 2H), 7.61 (d, J = 8.0 Hz, 1H), 7.68 (s, 1H), 7.71 (d, J = 8.0 Hz, 2H), 7.89 (d, J = 8.0 Hz, 1H), 7.98 (br.d, J = 5.2 Hz, 1H), 8.85 (s, 1H).

I-99  1H-NMR (CDCl3) δ: 3.17 (s, 3H), 3.38 (d, J = 18.0 Hz, 1H), 3.88 (1H, m), 3.90 (d, J = 18.0 Hz, 1H), 3.98 (d, J = 6.8 Hz, 1H), 4.27 (d, J = 6.8 Hz, 1H), 4.36-4.29 (m, 1H), 6.60 (d, J = 72 Hz, 1H), 7.74-7.31 (m, 12H), 8.09-8.02 (m ,1H), 8.61-8.56 (m, 1H).

I-101  1H-NMR (CDCl3) δ: 2.50 (s, 2H), 3.18 (s, 3H), 3.32 (d, J = 18.0 Hz, 1H), 3.95-3.78 (m, 4H), 3.96 (d, J = 18.0 Hz, 1H), 4.35-4.22 (m, 4H), 6.18 (s, 1H), 6.61 (t, J = 72.3 Hz, 1H), 7.44 (d, J = 8.4 Hz, 2H), 7.51-7.46 (m, 1H), 7.56 (1H, d, J = 8.4 Hz), 7.60 (2H, d, J = 8.4 Hz), 7.64 (1H, s), 8.06-8.00 (m, 1H), 8.59-8.55 (m, 1H).

I-108  1H-NMR (CDCl3) δ: 3.16 (s, 3H), 3.36 (d, J = 17.8 Hz, 1H), 3.94-3.82 (m, 1H), 3.97 (d, J = 13.8 Hz, 1H), 4.19 (d, J = 13.8 Hz, 1H), 4.36-4.28 (m, 1H), 6.61 (2H, t, J = 72.2 Hz), 7.54-7.49 (m, 1H), 7.57 (d, J = 8.7 Hz, 1H),7.69 (d, J = 8.5 Hz, 2H), 7.80 (d, J = 8.5 Hz, 2H), 7.98-7.91 (m, 1H), 8.60-8.55 (m, 1H).

Biological Test Examples for the compounds of the present invention are described below.

Preparation Example 1 (Preparation of Recombinant Human MGAT2)

A full-length human MGAT2 gene to which a Flag-tag had been added at the N-terminal was inserted into pFastBac (from Invitrogen). A recombinant baculovirus was produced in accordance with the protocol for a Bac-to-Bac baculovirus expression system (produced by Invitrogen), and Sf-9 cells were infected therewith. The cells were collected and sonicated, and then the membrane fraction was collected through centrifugation. Western blotting analysis with an anti-Flag antibody was performed for the membrane fraction to confirm expression, and the membrane fraction was used as a recombinant human MGAT2 enzyme solution.

Test Example 1 (Measurement of Human MGAT2 Inhibitory Activity)

Solutions of the compounds of the present invention in DMSO were each aliquoted into 0.2-μL portions in a 384-well polystyrene microplate produced by Corning Incorporated, and 5 μL of an enzyme solution prepared with an assay buffer (100 mmol/L phosphate buffer (pH 7.4) containing 2 mmol/L DTT) and 5 μL of a substrate solution (100 mmol/L phosphate buffer (pH 7.4), 30 μmol/L 2-Oleoylglycerol, 10 μmol/L Oleoyl-CoA) were added thereto, and the resultant was stirred and centrifuged, and incubated in a moist chamber at room temperature for 1 hour. After enzymatic reaction, 50 μL of a quenching solution (containing 0.2 μmol/L Diolein-d5, 0.4% formic acid, and 50% isopropanol) containing Internal Standard (IS) was added to terminate the reaction, and the resultant was sealed in a plate produced by Shimadzu GLC Ltd., and then stirred and centrifuged, and measurement was performed by using an electrospray ionization method with a RapidFire360 and Agilent 6550 Q-TOF mass spectrometer. Diolein as a reaction product (P) of 2-Oleoylglycerol as the substrate and an ammonium adduct ion of the IS were detected, and the peak intensity ratio, P/IS, was calculated from the peak heights to evaluate the inhibitory activity. Inhibitory activities with/without addition of enzyme were defined as Control (+)/Control (−), respectively, and the respective % inhibitions were defined as 0% inhibition and 100% inhibition. The inhibitory activity was calculated from the formula below with TIBCO Spotfire (produced by TIBCO Software Inc.):

Inhibitory activity (%)=[1−{Sample−Control(−)}/{Control(+)−Control(−)}]*100 where Sample indicates a peak intensity ratio: P/IS, when the compound of the present invention was added.

TABLE 15

| No. | IC50 (nM) |
|---|---|
| I-1 | 21 |
| I-3 | 120 |
| I-4 | 32 |
| I-5 | 230 |
| I-6 | 120 |
| I-7 | 150 |
| I-8 | 13 |
| I-9 | 29 |
| I-10 | <4.6 |
| I-11 | 110 |
| I-12 | 2.5 |
| I-13 | 3.3 |
| I-14 | 8 |
| I-15 | 10 |
| I-16 | 52 |
| I-17 | 7.6 |
| I-18 | 330 |
| I-19 | 240 |
| I-20 | 35 |
| I-22 | 200 |
| I-23 | 750 |
| I-24 | 40 |
| I-26 | 2.3 |
| I-27 | 2.2 |
| I-28 | 100 |
| I-29 | 18 |
| I-30 | 12 |
| I-31 | 70 |
| I-32 | 97 |
| I-33 | 340 |
| I-35 | 18 |
| I-36 | 53 |
| I-37 | 28 |
| I-38 | 17 |
| I-39 | 91 |
| I-40 | 43 |
| I-41 | 75 |
| I-42 | 10 |
| I-43 | <1 |
| I-44 | 9.2 |
| I-45 | 4.4 |
| I-46 | 62 |
| I-47 | 0.73 |
| I-48 | 3.2 |
| I-49 | 140 |
| I-51 | 130 |
| I-52 | 3.1 |
| I-53 | 11 |
| I-54 | 82 |
| I-55 | 160 |
| I-56 | 17 |
| I-57 | 0.62 |
| I-58 | 34 |
| I-59 | 1.1 |
| I-60 | 27 |
| I-61 | 27 |
| I-62 | 59 |
| I-63 | 110 |
| I-64 | 14 |
| I-65 | 280 |
| I-66 | 410 |
| I-67 | 40 |
| I-68 | 440 |
| I-69 | 43 |
| I-70 | 5.3 |
| I-71 | 940 |
| I-72 | 1 |
| I-73 | 77 |
| I-75 | 78 |
| I-78 | 25 |
| I-80 | 990 |
| I-81 | 140 |
| I-83 | 22 |
| I-85 | 24 |
| I-86 | 1.9 |
| I-88 | 21 |
| I-90 | 27 |
| I-91 | 6.8 |
| I-94 | 59 |
| I-95 | 17 |
| I-97 | 39 |
| I-98 | 70 |
| I-99 | 26 |
| I-100 | 370 |
| I-101 | 42 |
| I-102 | 21 |
| I-103 | 6.6 |
| I-105 | 9.2 |
| I-106 | 7.7 |
| I-108 | 46 |
| I-110 | 91 |
| I-111 | 33 |
| I-112 | 3.8 |
| I-114 | 4.1 |
| I-115 | 110 |

Test Example 2 (Metabolism Stability Test)

Using commercially available pooled human hepatic microsomes, the compound of the present invention was reacted for a constant time, a remaining rate was calculated by comparing a reacted sample and an unreacted sample, thereby, a degree of metabolism of the compound of the present invention in liver was assessed.

A reaction was performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a methanol/acetonitrile=1/1 (v/v) solution, mixed and centrifuged at 3000 rpm for 15 minutes. The compound of the present invention in the supernatant was quantified by LC/MS/MS, and a remaining amount of the compound of the present invention after the reaction was calculated, letting a compound amount at 0 minute reaction time to be 100%. Hydrolysis reaction was performed in the absence of NADPH, and glucuronidation reaction was performed in the presence of 5 mmol/L UDP-glucuronic acid instead of NADPH. Then, the same operation was carried out.

Test Example 3 (Solubility Test)

The solubility of the compound of the present invention was determined under 1% DMSO addition conditions. 10 mmol/L solution of the compound was prepared with DMSO, and 6 μL of the solution of the compound of the present invention was added to 594 μL of pH 6.8 artificial intestinal juice (118 mL of 0.2 mol/L NaOH test solution and water were added to 250 mL of 0.2 mol/L potassium dihydrogen phosphate test solution to reach 1000 mL). The mixture was left standing for 16 hours at 25° C., and the mixture was vacuum-filtered. The filtrate was two-fold diluted with methanol/water=1/1 (v/v), and the compound concentration in the filtrate was measured with HPLC or LC/MS/MS by the absolute calibration method.

Test Example 4 (Phototoxicity Test)

An erythrocyte photohemolysis test (Wolfgang J. W. Pepe et al., ATLA29, 145-162, 2001), which is an evaluation method using effect to biomembranes and photoperoxidation as indexes, was conducted as an In vitro phototoxicity test. In this method, a solution of the compound of the present invention was prepared with dimethylsulfoxide as a medium, to which a sheep erythrocyte solution in a ratio of 2.5% (v/v) with respect to the prepared solution was added, and the thus-obtained mixed solution (concentration: 0.1 to 0.0008%) was used. The mixed solution was added to two microplates, and one of the prepared microplates was irradiated with light in UVA and UVB regions (10 J/cm$^2$, 290 to 400 nm) by using an ultraviolet fluorescence lamp (GL20SE lamp, SANKYO DENKI Co., Ltd., and, FL20S-BLB lamp, Panasonic Corporation), and subjected to centrifugation together with the microplate without irradiation with light, and then the absorbance (540 nm or 630 nm) of the supernatant was measured. To determine two indexes (effect to biomembranes and photoperoxidation) for evaluation of phototoxicity, the absorbance of the medium was subtracted from the absorbance obtained from the compound of the present invention for each of the cases with and without irradiation with light, and the thus-calculated values were used for the subsequent calculations. With respect to effect to biomembranes, a photohemolysis rate was determined from the difference in absorbance (540 nm) between the case with irradiation with light and the case without irradiation with light, and, with respect to photoperoxidation, change in absorbance (630 nm) between the case with irradiation with light and the case without irradiation with light was determined. In calculation of a photohemolysis rate, the absorbance (540 nm) obtained from a 2.5% (v/v) sheep erythrocyte solution which had been subjected to forced hemolysis with distilled water was defined as the 100% photohemolysis rate and used as a reference.

Test Example 5 (Cytotoxicity Test)

Cells after being exposed to the compound were automatically counted by using the cell image analyzer Toxinsight (Thermo Fisher Scientific) to evaluate the cytotoxicity of the compound of the present invention.

HepG2 cells (derived from human liver cancer cells) were seeded in a 384-well plate at 60000 cells/mL, and a solution of the compound was added to each well after 24 hours. The solution of the compound was a solution of the compound of the present invention in DMSO (five stage dilution from maximum concentration of 50 µmol/L to minimum concentration of about 3.1 µmol/L at 2 fold ratio), and a solution consisting only of DMSO was used as a negative control, and a solution of camptothecin was used as a positive control. The solution of the compound of the present invention in DMSO, the negative control solution, or the positive control solution was added to each well. After 71 hours, a solution of Hoechst 33342 diluted with Dulbecco's phosphate buffer solution (D-PBS) to a final concentration of 1 µg/mL was added to each well, and nuclear staining was performed in an incubator at 37° C. and 5% CO$_2$ for 1 hour. After the staining, the resultant was fixed with 4% paraformaldehyde in a CO$_2$ incubator at 37° C. for 20 minutes. Finally, the wells were washed by D-PBS three times, and nuclei with development of fluorescence were counted for each well by using a Toxinsight (Thermo Fisher Scientific). Four wells were assigned for one concentration, and the mean value and variation (SD) of nucleus counts (counts of cells for which toxicity was not found) in the four wells were calculated. Comparison was made with the negative control group, and an exposure concentration to the compound (IC$_{50}$) at which the mean value was lowered to less than 50% of the mean value for the negative control was calculated. A smaller IC$_{50}$ value was rated as a higher risk of cytotoxicity.

Test Example 6 (Anti-Obesity Effect Test)

The anti-obesity effect of the compound of the present invention was examined by using C57BL/6j mice (DIO mice) provided with a high-fat diet (TestDiet; 58Y1).

Five-week-old male C57BL/6j mice (CLEA Japan, Inc.) were purchased, and grown with feeding of a high-fat diet under 12-hour light-dark cycles for 4 weeks to produce DIO mice. A medium (0.5% HPMC) was administered twice per day from 3 weeks before administration of the compound. Randomization was performed for grouping (n=7) on the basis of body weight and change in food consumption during the period of administration for conditioning. Forced oral administration of Example Compound or a medium (0.5% HPMC) was performed twice per day from Day 1 to Day 28. Body weight and food consumption were measured every day. Dissection was performed on Day 28, and measurement of the weight of epididymal fat and a biochemical test for the blood collected were conducted.

Test Example 7 (CYP Inhibition Test)

Using commercially available pooled human hepatic microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4) as typical substrate metabolism reactions of human main five CYP enzyme forms (CYP1A2, 2C9, 2C19, 2D6, 3A4), an inhibitory degree of each metabolite production amount by the compound of the present invention was assessed.

The reaction conditions are as follows: substrate, 0.5 µmol/L ethoxyresorufin (CYP1A2), 100 µmol/L tolbutamide (CYP2C9), 50 µmol/L S-mephenytoin (CYP2C19), 5 µmol/L dextromethorphan (CYP2D6), 1 µmol/L terfenadine (CYP3A4); reaction time, 15 minutes; reaction temperature, 37° C.; enzyme, pooled human hepatic microsome 0.2 mg protein/mL; concentration of the compound of the present invention, 1, 5, 10, 20 µmol/L (four points).

Each five kinds of substrates, human hepatic microsome, or the compound of the present invention in 50 mmol/L Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (V/V) solution was added to stop the reaction. After the centrifugation at 3000 rpm for 15 minutes, resorufin (CYP1A2 metabolite) in the supernatant was quantified by a fluorescent multilabel counter or LC/MS/MS, and tolbutamide hydroxide (CYP2CP metabolite), mephenytoin 4' hydroxide (CYP2C19 metabolite), dextrorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%). Remaining activity (%) was calculated. IC50 was calculated by reverse presumption by a logistic model using the concentration and an inhibition rate.

Test Example 8 (BA Test)

Materials and Methods for Experiments to Evaluate Oral Absorption
(1) Animals: the mice or SD rats were used.
(2) Breeding conditions: the mice or SD rats were allowed to freely take solid food and sterilized tap water.
(3) Dose and grouping: orally or intravenously administered at a predetermined dose; grouping was as follows (Dose depended on the compound)
   Oral administration: 1 to 30 mg/kg (n=2 to 3)
   Intravenous administration: 0.5 to 10 mg/kg (n=2 to 3)
(4) Preparation of dosing solution: for oral administration, in a solution or a suspension state; for intravenous administration, in a solubilized state
(5) Administration method: in oral administration, forcedly administer into ventriculus with oral probe; in intravenous administration, administer from caudal vein or femoral vein with a needle-equipped syringe
(6) Evaluation items: blood was collected over time, and the plasma concentration of the compound of the present invention was measured by LC/MS/MS.
(7) Statistical analysis: regarding the transition of the plasma concentration of the compound of the present invention, the area under the plasma concentration-time curve (AUC) was calculated by non-linear least squares program WinNonlin (registered trademark), and the bioavailability (BA) of the compound of the present invention was calculated from the AUCs of the oral administration group and intravenous administration group.

Test Example 9 (CYP3A4 (MDZ) MBI Test)

This test is a test to evaluate Mechanism based inhibition (MBI) potency from enhancement of CYP3A4 inhibition of the compound of the present invention by a metabolism reaction. CYP3A4 inhibition was evaluated by using pooled human hepatic microsomes and employing, as an index, midazolam (MDZ) 1-hydroxylation reaction.

The reaction conditions are as follows: substrate, 10 µmol/L MDZ; pre-reaction time, 0 or 30 minutes; reaction time, 2 minutes; reaction temperature, 37° C.; pooled human hepatic microsome, at pre-reaction 0.5 mg/mL, at reaction 0.05 mg/mL (at 10-fold dilution); concentration of the compound of the present invention, 1, 5, 10, 20 µmol/L (four points).

Pooled human hepatic microsomes in K-Pi buffer (pH 7.4) and a solution of the compound of the present invention as a pre-reaction solution were added to a 96-well plate at the above composition of the pre-reaction. A part of pre-reaction solution was transferred to another 96-well plate so that it was 1/10 diluted with a substrate and K-Pi buffer. NADPH as a co-factor was added in order to initiate a reaction as an index (without preincubation). After a predetermined time of a reaction, methanol/acetonitrile=1/1 (V/V) solution was added to stop the reaction. On the other hand, NADPH was also added to a remaining preincubation solution in order to initiate a preincubation (with preincubation). After a predetermined time of a preincubation, a part was transferred to another plate so that it was 1/10 diluted with a substrate and K-Pi buffer to initiate a reaction as an index. After a predetermined time of a reaction, methanol/acetonitrile=1/1 (V/V) solution was added in order to stop the reaction. The plate on which each index reaction had been performed was centrifuged at 3000 rpm for 15 minutes, and thereafter 1-hydroxylated midazolam in the supernatant was quantified by LC/MS/MS.

Addition of only DMSO which was a solvent dissolving the compound of the present invention to a reaction system was adopted as a control (100%), remaining activity (%) was calculated at each concentration of the compound of the present invention added as the solution. IC was calculated by reverse-presumption by a logistic model using a concentration and an inhibition rate. IC at Preincubation 0 min/IC at Preincubation 30 min was defined as a value of Shifted IC, and a case that Shifted IC was 1.5 or more was regarded as Positive, and a case that Shifted IC was 1.0 or less was regarded as Negative.

Test Example 10 (Powder Solubility Test)

Appropriate quantity of the compound of the present invention was put in suitable containers. 200 µL of JP-1 solution (water was added to 2.0 g of sodium chloride and 7.0 mL of hydrochloric acid to reach 1000 mL), 200 µL of JP-2 solution (500 mL of water was added to 500 mL of phosphate buffer (pH 6.8)) or 20 mmol/L sodium taurocholate (TCA)/JP-2 solution (JP-2 solution was added to 1.08 g of TCA to reach 100 mL) was independently added to each container. When total amount was dissolved after adding the test reagent, the compound of the present invention was added appropriately. After sealing and shaking at 37° C. for 1 hour, solution is filtrated and 100 µL of methanol is added to 100 µL of each filtrate to dilute two-fold. The dilution rate is changed as necessary. After checking that there was no bubble and deposit, the container was sealed and shaken. The compound of the present invention was measured using HPLC by absolute calibration curve method.

Test Example 11 (Fluctuation Ames Test)

Mutagenicity of the compound of the present invention was evaluated.

20 µL of freezing-stored rat typhoid *bacillus* (*Salmonella typhimurium* TA98 strain, TA100 strain) was inoculated on 10 mL of a liquid nutrient medium (2.5% Oxoid nutrient broth No. 2), and this was cultured before shaking at 37° C. for 10 hours. 8.0 mL of a bacterial solution of the TA98 strain was centrifuged (2000×g, 10 minutes) to remove a culturing solution. The bacteria was suspended in 8.0 mL of a Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4.7H_2O$: 0.1 g/L), the suspension was added to 120 mL of an Exposure medium (Micro F buffer containing Biotin: 8 µg/mL, histidine: 0.2 µg/mL, glucose: 8 mg/mL). The TA100 strain was added to 120 mL of the Exposure medium relative to 3.1 mL of the bacterial solution to prepare a test bacterial solution. Each 12 µL of DMSO solution of the compound of the present invention (several stage dilution from maximum dose 50 mg/mL at 2 to 3 fold ratio), DMSO as a negative control, and 50 µg/mL of 4-nitroquinoline-1-oxide DMSO solution for the TA98 strain, 0.25 µg/mL of 2-(2-furyl)-3-(5-nitro-2-furyl)acrylamide DMSO solution for the TA100 strain under the non-metabolism activating condition, 40 µg/mL of 2-aminoanthracene DMSO solution for the TA98 strain, 20 µg/mL of 2-aminoanthracene DMSO solution for the TA100 strain under the metabolism activating condition as a positive control, and 588 µL of the test bacterial solution (a mixed solution of 498 µL of the test bacterial solution and 90 µL of S9 mix under the metabolism activating condition) were mixed, and this was shaking-cultured at 37° C. for 90 minutes. 230 µL of the bacterial solution exposed to the compound of the present invention was mixed with 1150 μL of an Indicator medium (Micro F buffer containing biotin: 8 μg/mL, histidine: 0.2 μg/mL, glucose: 8 mg/mL, Bromo Cresol Purple: 37.5 μg/mL), each 50 μL was dispensed into microplate 48 wells/dose, and this was subjected to stationary culturing at 37° C. for 3 days. Since a well containing a bacterium which had obtained the proliferation ability by mutation of an amino acid (histidine) synthesizing enzyme gene turns from purple to yellow due to a pH change, the bacterium proliferation well which had turned to yellow in 48 wells per dose was counted, and was assessed by comparing with a negative control group.

Test Example 12 (hERG Test)

For the purpose of assessing risk of an electrocardiogram QT interval prolongation of the compound of the present invention, effects of the compound of the present invention on delayed rectifier K$^+$ current ($I_{Kr}$), which plays an important role in the ventricular repolarization process, was studied using CHO cells expressing human ether-a-go-go related gene (hERG) channel.

After a cell was retained at a membrane potential of −80 mV by whole cell patch clamp method using an automated patch clamp system (QPatch; Sophion BIoscience A/S), $I_{Kr}$ induced by application of a leak potential of −50 mV followed by depolarization pulse stimulation at +20 mV for 2 seconds and, further, repolarization pulse stimulation at −50 mV for 2 seconds, was recorded. After the generated current was stabilized, extracellular solution (NaCl: 145 mmol/L, KCl: 4 mmol/L, CaCl$_2$: 2 mmol/L, MgCl$_2$: 1 mmol/L, glucose: 10 mmol/L, HEPES (4-(2-hydroxyethyl)-1-piperazineethanesulfonic acid): 10 mmol/L, pH=7.4), in which the compound of the present invention had been dissolved at an objective concentration, was applied to the cell at room temperature for 10 minutes. From the recording $I_{Kr}$, an absolute value of the tail peak current was measured based on the current value at the resting membrane potential using analysis software (Falster Patch; Sophion Bioscience A/S). Further, the % inhibition relative to the tail peak current before application of the compound of the present invention was calculated to assess influence of the compound of the present invention on $I_{Kr}$.

INDUSTRIAL APPLICABILITY

Since the compounds of the present invention have MGAT2 inhibitory activity, they are useful as a medicine for MGAT2-related diseases including obesity, metabolic syndrome, hyperlipidemia, hypertriglyceridemia, hyper-VLDL-triglyceridemia, hyperfattyacidemia, diabetes mellitus, and arteriosclerosis.

The invention claimed is:
1. A compound represented by Formula (I):

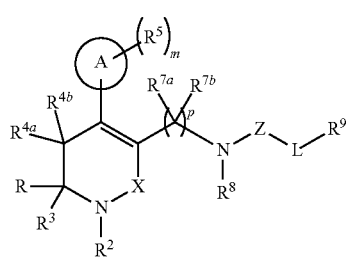

wherein
X is C(=O), C(=S), or SO$_2$;
Z is C(=O), C(=S), C(=N—R$^N$), or SO$_2$;
L is a single bond, —O—, —S—, or —NR$^N$—;
R is R$^6$ or a group represented by the following formula:

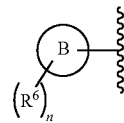

A is aromatic carbocycle, non-aromatic carbocycle, aromatic heterocycle, or non-aromatic heterocycle;
B is aromatic carbocycle, non-aromatic carbocycle, aromatic heterocycle, or non-aromatic heterocycle;
R$^2$ is hydrogen, substituted or unsubstituted alkyl, substituted or unsubstituted alkylcarbonyl, substituted or unsubstituted alkyloxycarbonyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocycly-loxycarbonyl, substituted or unsubstituted non-aromatic carbocycly-loxycarbonyl, substituted or unsubstituted aromatic heterocyclyloxycarbonyl, substituted or unsubstituted non-aromatic heterocycly-loxycarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;
R$^3$ is hydrogen, cyano, substituted or unsubstituted carbamoyl, substituted or unsubstituted alkyl, substituted or unsubstituted alkenyl, substituted or unsubstituted alkynyl, substituted or unsubstituted alkylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;
R$^{4a}$ and R$^{4b}$ are each independently hydrogen, halogen, hydroxy, cyano, substituted or unsubstituted alkyl, substituted or unsubstituted non-aromatic carbocycle, or substituted or unsubstituted non-aromatic heterocycle, or, optionally, R$^{4a}$ and R$^{4b}$ are taken together with the adjacent carbon atom to form substituted or unsubstituted non-aromatic carbocycle or substituted or unsubstituted non-aromatic heterocycle;
R$^5$ is each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyloxy, substituted or unsubstituted alkenylcarbonyloxy, substituted or unsubstituted alkynylcarbonyloxy, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by the formula: $-L^1-N=S(=O)(-R^{S1})-R^{S2}$, a group represented by the formula: $-L^1-S(=O)(=N-R^N)-R^{S1}$, a group represented by the formula: $-N=S(=N-R^N)(-R^{S1})-R^{S2}$, or a group represented by the formula: $-S(=N-R^N)_2-R^{S1}$;

$R^6$ is each independently halogen, hydroxy, cyano, carboxy, substituted or unsubstituted carbamoyl, substituted or unsubstituted thiocarbamoyl, substituted or unsubstituted amidino, substituted or unsubstituted amino, substituted or unsubstituted ureido, substituted or unsubstituted guanidino, pentafluorothio, sulfo, substituted or unsubstituted sulfamoyl, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyloxy, substituted or unsubstituted alkenylcarbonyloxy, substituted or unsubstituted alkynylcarbonyloxy, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfanyl, substituted or unsubstituted alkenylsulfanyl, substituted or unsubstituted alkynylsulfanyl, substituted or unsubstituted alkylsulfinyl, substituted or unsubstituted alkenylsulfinyl, substituted or unsubstituted alkynylsulfinyl, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylcarbonyloxy, substituted or unsubstituted non-aromatic carbocyclylcarbonyloxy, substituted or unsubstituted aromatic heterocyclylcarbonyloxy, substituted or unsubstituted non-aromatic heterocyclylcarbonyloxy, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfanyl, substituted or unsubstituted non-aromatic carbocyclylsulfanyl, substituted or unsubstituted aromatic heterocyclylsulfanyl, substituted or unsubstituted non-aromatic heterocyclylsulfanyl, substituted or unsubstituted aromatic carbocyclylsulfinyl, substituted or unsubstituted non-aromatic carbocyclylsulfinyl, substituted or unsubstituted aromatic heterocyclylsulfinyl, substituted or unsubstituted non-aromatic heterocyclylsulfinyl, substituted or unsubstituted aromatic carbocyclylsulfonyl, substituted or unsubstituted non-aromatic carbocyclylsulfonyl, substituted or unsubstituted aromatic heterocyclylsulfonyl, substituted or unsubstituted non-aromatic heterocyclylsulfonyl, a group represented by the formula: $-L^1-N=S(=O)(-R^{S1})-R^{S2}$, a group represented by the formula: $-L^1-S(=O)(=N-R^N)-R^{S1}$, a group represented by the formula: $-N=S(=N-R^N)(-R^{S1})-R^{S2}$, or a group represented by the formula: $-S(=N-R^N)_2-R^{S1}$;

$R^{7a}$ is each independently hydrogen, halogen, hydroxy, cyano, substituted or unsubstituted amino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, and $R^{7b}$ is each independently hydrogen, halogen, hydroxy, cyano, substituted or unsubstituted amino, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl, or, optionally, $R^{7a}$ and $R^{7b}$ attached to the same carbon atom are taken together with the adjacent carbon atom to form substituted or unsubstituted non-aromatic carbocycle or substituted or unsubstituted non-aromatic heterocycle;

$R^8$ is hydrogen or substituted or unsubstituted alkyl;

$R^9$ is hydrogen, substituted or unsubstituted amino, substituted or unsubstituted alkyl, substituted or unsubstituted alkenyl, substituted or unsubstituted alkynyl, substituted or unsubstituted alkylcarbonyl, substituted or unsubstituted alkenylcarbonyl, substituted or unsubstituted alkynylcarbonyl, substituted or unsubstituted alkyloxycarbonyl, substituted or unsubstituted alkenyloxycarbonyl, substituted or unsubstituted alkynyloxycarbonyl, substituted or unsubstituted alkylsulfonyl, substituted or unsubstituted alkenylsulfonyl, substituted or unsubstituted alkynylsulfonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted aromatic carbocyclyloxycarbonyl, substituted or unsubstituted non-aromatic carbocyclyloxycarbonyl, substituted or unsubstituted aromatic heterocyclyloxycarbonyl, substituted or unsubstituted non-aromatic heterocyclyloxycarbonyl, substituted or unsubstituted aromatic carbocyclylsulfonyl, substituted or unsubstituted non-aromatic carbocyclylsulfonyl, substituted or unsubstituted aromatic heterocyclylsulfonyl, or substituted or unsubstituted non-aromatic heterocyclylsulfonyl;

$L^1$ is each independently a single bond, alkylene, or $C(=O)$;

$R^{S1}$ and $R^{S2}$ are each independently hydrogen, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or, optionally, $R^{S1}$ and $R^{S2}$ bonding to the same sulfur atom are taken together with the sulfur atom to form substituted or unsubstituted non-aromatic heterocycle;

$R^N$ is each independently hydrogen, cyano, substituted or unsubstituted carbamoyl, substituted or unsubstituted alkyl, substituted or unsubstituted alkylcarbonyl, substituted or unsubstituted alkyloxycarbonyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylcarbonyl, substituted or unsubstituted non-aromatic carbocyclylcarbonyl, substituted or unsubstituted aromatic heterocyclylcarbonyl, or substituted or unsubstituted non-aromatic heterocyclylcarbonyl;

m is an integer of 0 to 5;

n is an integer of 0 to 5; and p is an integer of 1 to 6, or its pharmaceutically acceptable salt.

2. The compound or its pharmaceutically acceptable salt according to claim 1, wherein $R^{7a}$ and $R^{7b}$ are each hydrogen.

3. The compound or its pharmaceutically acceptable salt according to claim 1, wherein p is 1.

4. The compound or its pharmaceutically acceptable salt according to claim 1, wherein Z is $C(=O)$ or $SO_2$.

5. The compound or its pharmaceutically acceptable salt according to claim 1, wherein A is aromatic carbocycle or aromatic heterocycle.

6. The compound or its pharmaceutically acceptable salt according to claim 1, wherein B is aromatic carbocycle or aromatic heterocycle.

7. The compound or its pharmaceutically acceptable salt according to claim 1, wherein $R^5$ is each independently halogen, substituted or unsubstituted alkyl, substituted or unsubstituted alkenyl, substituted or unsubstituted alkyloxy, substituted or unsubstituted alkylcarbonyl, or substituted or unsubstituted non-aromatic carbocyclyl.

8. The compound or its pharmaceutically acceptable salt according to claim 1, wherein $R^6$ is each independently halogen, substituted or unsubstituted alkyl, substituted or unsubstituted alkenyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl.

9. The compound or its pharmaceutically acceptable salt according to claim 1, wherein the compound is selected from the group consisting of
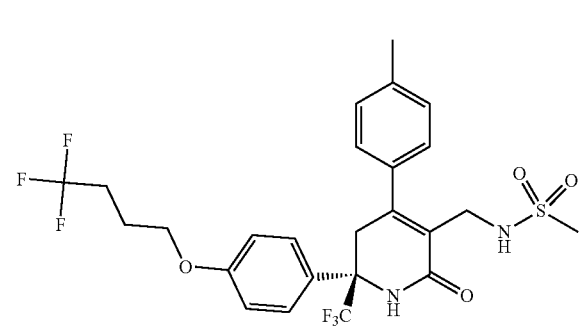
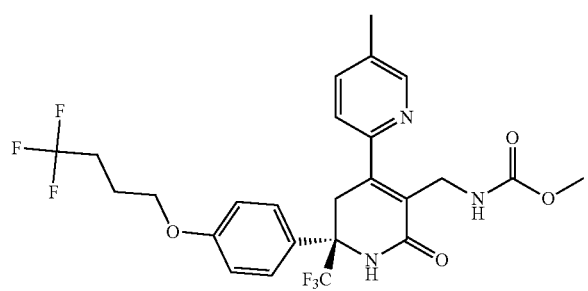
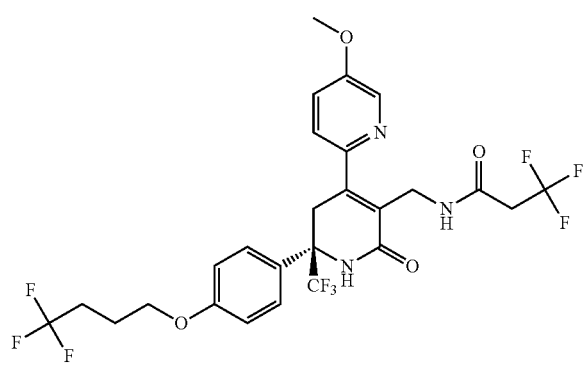
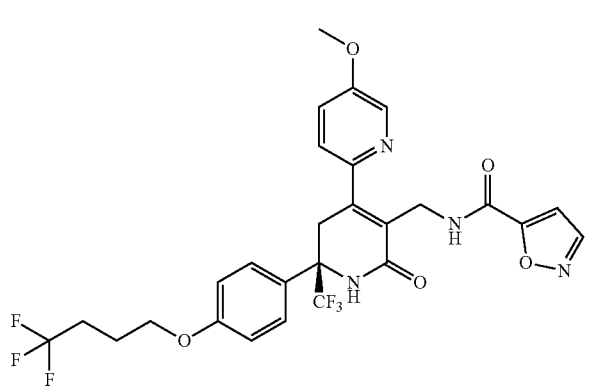
-continued
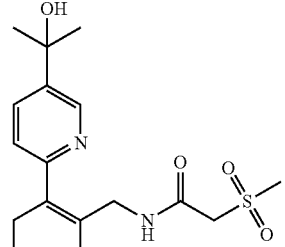
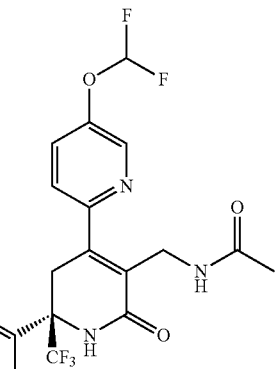
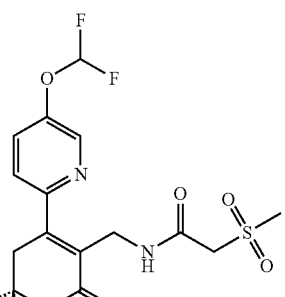
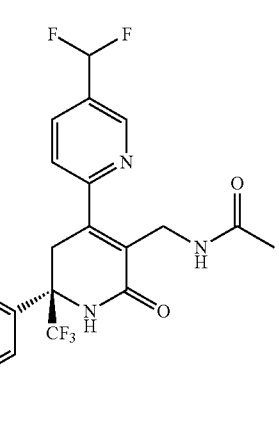

127
-continued
128
-continued
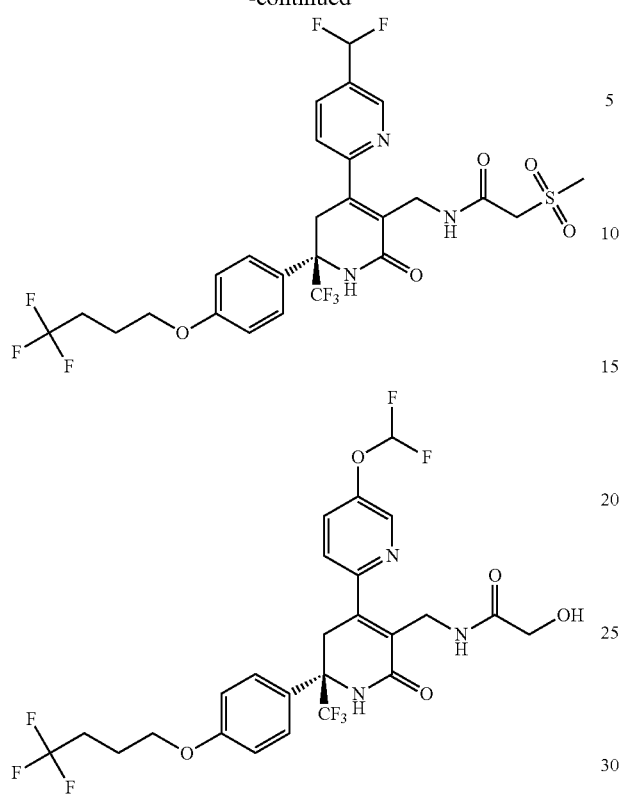
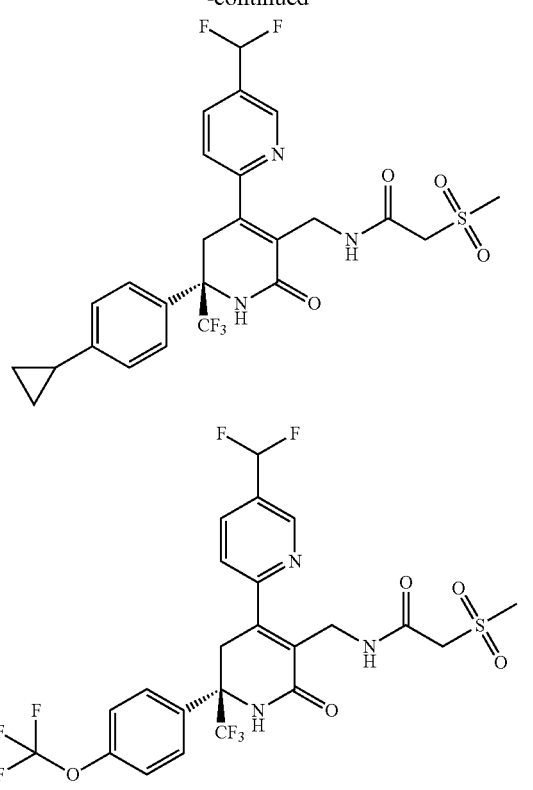
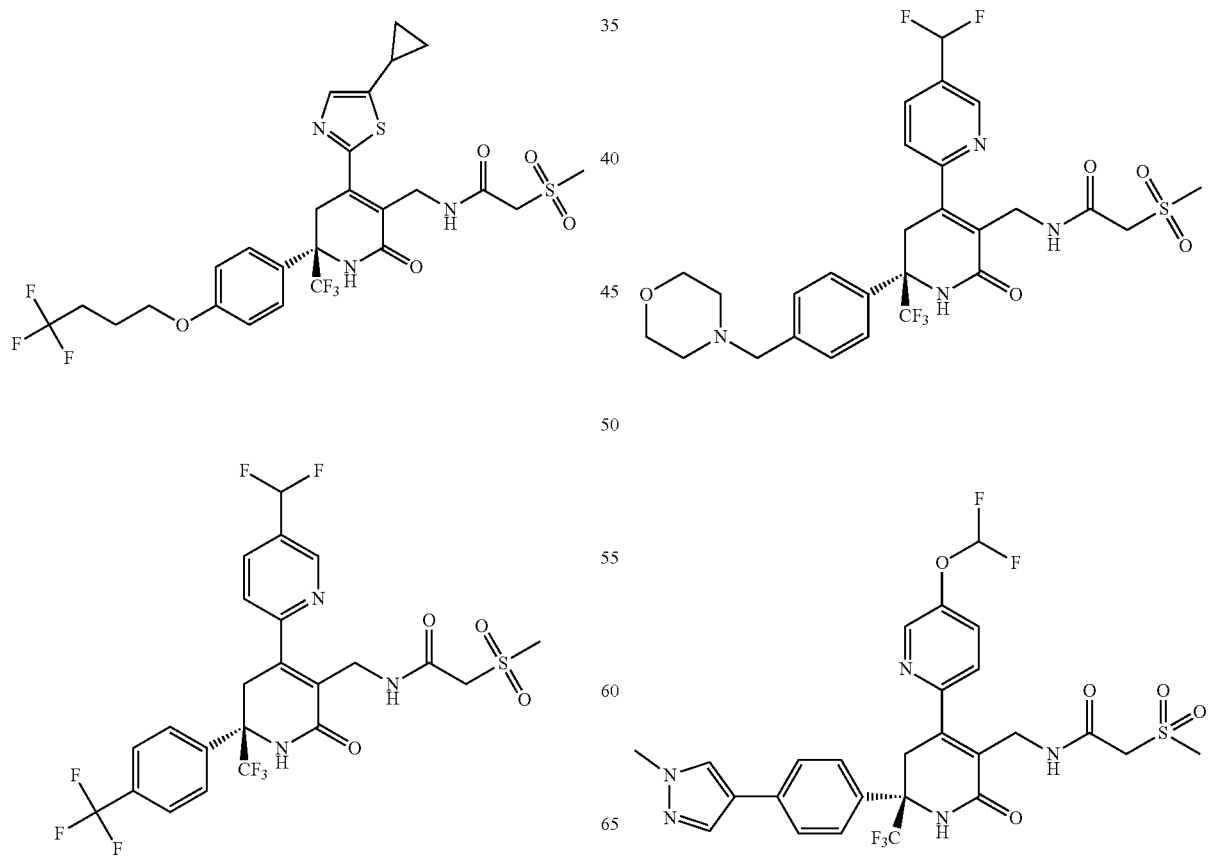

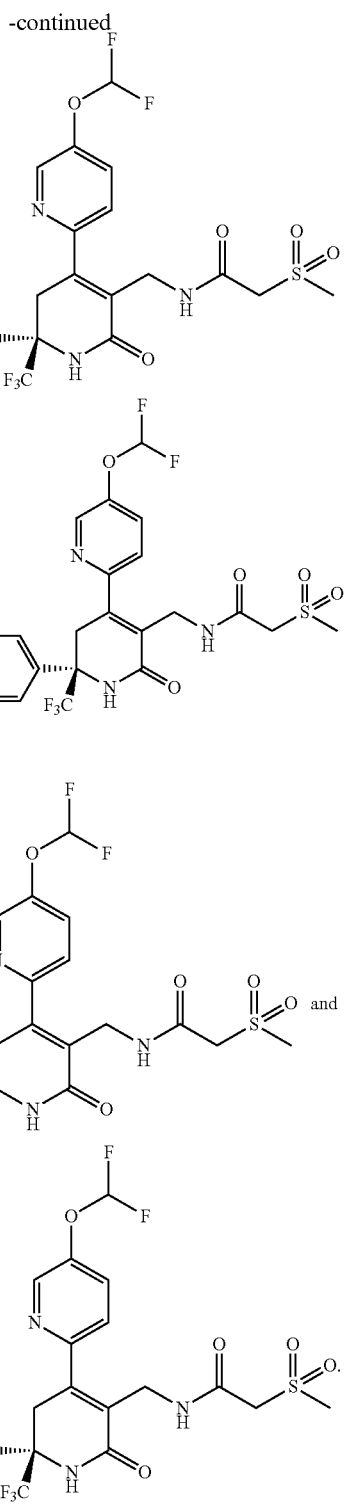

10. A pharmaceutical composition comprising the compound or its pharmaceutically acceptable salt according to claim 1 and a pharmaceutical additive.

11. A method for treating an MGAT2-associated disease selected from the group consisting of obesity, metabolic syndrome, hyperlipidemia, hypertriglyceridemia, hyper-VLDL-triglyceridemia, hyperfattyacidemia, diabetes mellitus and arteriosclerosis, comprising administering an effective amount of the compound or its pharmaceutically acceptable salt according to claim 1 to a subject in need thereof.

12. The compound or its pharmaceutically acceptable salt according to claim 1, wherein $R^{7a}$ and $R^{7b}$ are each hydrogen, p is 1, and Z is C(=O) or $SO_2$.

13. The compound or its pharmaceutically acceptable salt according to claim 1, wherein X is C(=O),
Z is C(=O) or $SO_2$,
L is a single bond, —O— or —$NR^{N}$-,
R is a group represented by the following formula:

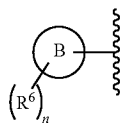

A is aromatic carbocycle or aromatic heterocycle,
B is aromatic carbocycle or aromatic heterocycle,
$R^2$ is hydrogen,
$R^3$ is substituted or unsubstituted alkyl,
$R^{4a}$ and $R^{4b}$ are each independently hydrogen,
$R^5$ is each independently halogen, substituted or unsubstituted alkyl, substituted or unsubstituted alkenyl, substituted or unsubstituted alkyloxy, substituted or unsubstituted alkylcarbonyl, or substituted or unsubstituted non-aromatic carbocyclyl,
$R^6$ is each independently halogen, substituted or unsubstituted alkyl, substituted or unsubstituted alkenyl, substituted or unsubstituted alkyloxy, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
$R^{7a}$ and $R^{7b}$ are each hydrogen,
$R^8$ is hydrogen,
$R^9$ is hydrogen, substituted or unsubstituted amino, substituted or unsubstituted alkyl, substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl,
m is 0 or 1,
n is 1 or 2, and
p is 1.

14. The compound or its pharmaceutically acceptable salt according to claim 13, wherein $R^9$ is methyl, propyl, tert-butyl, pentyl, trifluoroethyl, amino, methylsulfonylmethyl, phenyl, cyclopropyl, cyclobutyl, cyclohexyl, tetrahydrofuryl, or isoxazolyl.

* * * * *